United States Patent
Uesugi et al.

(10) Patent No.: US 7,449,480 B2
(45) Date of Patent: *Nov. 11, 2008

(54) SMALL MOLECULE INHIBITORS OF HER2 EXPRESSION

(75) Inventors: Motonari Uesugi, Houston, TX (US); Shinichi Asada, Otsu (JP)

(73) Assignee: Baylor College of Medicine, Houston, TX (US)

( * ) Notice: Subject to any disclaimer, the term of this patent is extended or adjusted under 35 U.S.C. 154(b) by 576 days.

This patent is subject to a terminal disclaimer.

(21) Appl. No.: 10/770,303

(22) Filed: Feb. 2, 2004

(65) Prior Publication Data

US 2005/0283007 A1    Dec. 22, 2005

Related U.S. Application Data

(63) Continuation-in-part of application No. 10/405,387, filed on Apr. 2, 2003, now Pat. No. 7,019,017.

(60) Provisional application No. 60/380,481, filed on May 14, 2002.

(51) Int. Cl.
*A61K 31/445* (2006.01)
*C07D 401/04* (2006.01)

(52) U.S. Cl. ........................... 514/316; 546/187

(58) Field of Classification Search ............ 514/316; 546/187
See application file for complete search history.

(56) References Cited

U.S. PATENT DOCUMENTS

| | | | |
|---|---|---|---|
| 5,019,660 A | 5/1991 | Chapman et al. | |
| 5,053,434 A | 10/1991 | Chapman | |
| 5,786,379 A | 7/1998 | Bernardon | |
| 5,854,245 A | 12/1998 | Duggan et al. | |
| 5,877,342 A | 3/1999 | Bernardon et al. | |
| 6,127,415 A | 10/2000 | Pfahl et al. | |
| 6,462,064 B1 | 10/2002 | Pfahl et al. | |
| 7,019,017 B2 * | 3/2006 | Uesugi et al. | 514/316 |

FOREIGN PATENT DOCUMENTS

WO    WO-01/95856    12/2001

OTHER PUBLICATIONS

Asada, et al; Database CAPLUS on STN (Columbus, OH, USA) No. 138:363718, 'A gene-expression inhibitor that targets an alph-helix-mediated protein interaction', abstract; J. Am. Chem. Society, vol. 125, pp. 4992-4993 (2003).

Greene TW "Protective groups in organic synthesis" Wiley & Sons, pp. 218, 222, 284 (1982).
R. Redline et al., "Placental Lesions Associated with Cerebral Palsy and Neurologic Impairment Following Term Birth," Archivers of Pathology and LAboratory Medicine vol. 124, Dec. 2000, pp. 1785-1791.
H. Roh et al.; HER2/neuy antisense targeting of human breat carcinoma; Oncogene 19, 2000; 6138-6143.
S. Asada et al., "External Control of Her2 Expression and Cancer Cell Growth by Targeting a Ras-linked Coactivator," PNAS vol. 99 No. 20, Oct. 1, 2002, pp. 12747-12752.
H. Roh, "Down-Regulation of HER2/neu Expression Induces Apoptosis in Human Cancer Cells That Overexpress HER2/neu," Cancer Research 60, Feb. 1, 2000, pp. 560-565.
S. Chiang et al, "Targeting the Ets Binding Site of the HER2/neu Promoter with Pyrrole-Imidazole Polyamides," The Journal of Biological Chemistry vol. 275, No. 32, Issue of Aug. 11, 2000, pp. 24246-24254.
S. Asada et al., "A Gene-Expression Inhibitor that Tergets an a-Helix-Mediated Protein Interaction," Journal American Chemical Society vol. 125, No. 17, 2003, pp. 4992-4993.
H. Shimogawa et al., "A Wrench-Shaped Synthetic Molecule that Modulates a Transcription Factor—Coactivator Interaction", J. Am. Chem. Soc. 2004, 126, 3461-3471.
Supplementary European Search Report issued Feb. 28, 2008 during the prosecution of European Application No. 03 73 6448.

* cited by examiner

*Primary Examiner*—Celia Chang
(74) *Attorney, Agent, or Firm*—Fulbright & Jaworski, LLP

(57) ABSTRACT

Peptide mimetic small molecule inhibitors of Sur-2 are provided having the general formula:

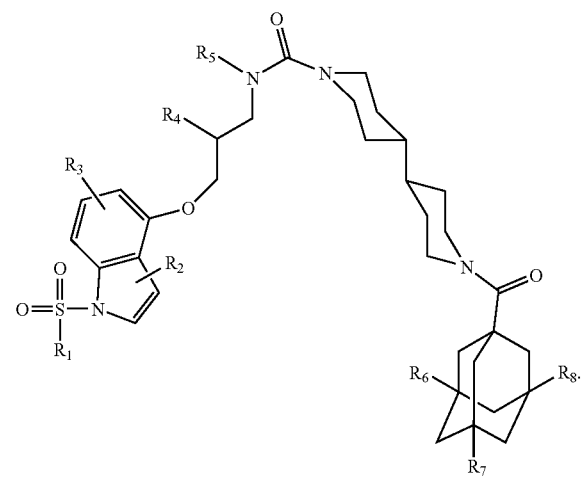

2 Claims, 37 Drawing Sheets

|  |  | DRIP130 binding |
|---|---|---|
|  | GST |  |
| TSSSSDELSW I IELLEK | wild-type | ▬ |
| TSSSSDELAW I IELLEK | S137→A | ▬ |
| TSSSSDELSA I IELLEK | W138→A |  |
| TSSSSDELSW A IELLEK | I139→A |  |
| TSSSSDELSW I AELLEK | I140→A |  |
| TSSSSDELSW I IALLEK | E141→A | ▬ |
| TSSSSDELSW I IEALEK | L142→A |  |
| TSSSSDELSW I IELAEK | L143→A |  |
| TSSSSDELSW I IELLAK | E144→A | ▬ |
| TSSSSDELSF I IELLEK | W138→F |  |
| TSSSSDELSL I IELLEK | W138→L |  |

FIG. 8B

Adamanolol

IC50 = 7 μM $C_{36}H_{52}N_4O_4$
Exact Mass: 604.40

$C_{33}H_{46}N_4O_4$
Mol. Wt.: 562.74

IC50 = >100 μM $C_{37}H_{54}N_4O_4$
Mol. Wt.: 618.85

IC50 = 7 μM $C_{38}H_{53}N_3O_4$
Mol. Wt.: 615.85

IC50 = 14 μM

IC50 = 20 μM

C₃₈H₄₆N₄O₄
Mol. Wt.: 622.80

IC50 = 14 μM

C₃₇H₅₄N₄O₄
Exact Mass: 618.41

IC50 = >100 μM

C₃₈H₅₄N₄O₅
Exact Mass: 646.41

IC50 = >100 μM

C₄₈H₇₃N₇O₈
Exact Mass: 875.55

C₄₃H₅₈N₄O₆S
Mol. Wt.: 759.01

IC50 = 3 μM

C₄₅H₅₇N₅O₆S
Mol. Wt.: 796.03

IC50 = 7 μM

C₄₆H₅₈N₄O₆S
Mol. Wt.: 795.04

IC50 = 7 μM

C₄₀H₅₄N₄O₆S₂
Mol. Wt.: 751.01

IC50 = 7 μM

IC50 = 3 µM

IC50 = 7 µM

IC50 = 14 µM

A

B

A

Compound 7b (wrenchnolol)

B

C

A

Compound 9

B

9          DAPI

C

Compound 15

Compound 14

SMALL MOLECULE INHIBITORS OF HER2 EXPRESSION

CROSS-REFERENCE TO RELATED APPLICATIONS

This application claims priority to U.S. Provisional Application No. 60/380,481, which was filed May 14, 2002, and U.S. application Ser. No. 10/405,387, which was filed Apr. 2, 2003, which are hereby incorporated by reference in its entirety.

STATEMENT REGARDING SPONSORED RESEARCH OR DEVELOPMENT

This research was supported by grant number Q-1490 from The Welch Foundation (Houston, Tex.).

TECHNICAL FIELD

The field of the invention relates to inhibitors of Her2 expression. The field of the invention also relates to peptide mimetic inhibitors of Sur-2, a Ras-linked subunit of the human mediator complex, and methods of their use the treatment of breast cancer in mammals.

BACKGROUND OF THE INVENTION

The proto-oncogene HER2/neu (C-erbB-2) encodes a transmembrane tyrosine kinase growth factor receptor. The name for the HER2 protein is derived from "Human Epidermal growth factor Receptor," as it features substantial homology with the epidermal growth factor receptor (EGFR). Overexpression of this transmembrane receptor has been found in ~30% of breast cancers (Slamon et al., 1987), amounting to as many as 60-thousand cases a year in the United States. To date, a wide variety of clinical studies, including more than 15,000 patients, have evaluated the relationship between HER2/neu abnormalities and breast cancer outcome, including more than 47 publications concerning the association of gene and/or protein abnormalities with prognosis (Ross et al., 1999). These studies clearly indicate that HER2 protein overexpression is associated with an adverse outcome in breast cancer.

Overexpression of the oncogene Her2 (neu/ErbB2) has been found in ~30% of breast tumors (Slamon et al., 1987; Ross et al., 1999). It is unclear why overexpression of this transmembrane receptor occurs in breast cancers, but patients who have Her2 excesses typically have more aggressive disease with enhanced metastasis and increased resistance to chemotherapy. Monoclonal antibodies against the Her2 protein have been successful in treating these Her2-positive patients. A humanized antibody called Herceptin® has demonstrated tumor inhibitory and chemosensitizing effects in clinical studies and is the only drug that FDA has approved for treatment of Her2-overexpressing breast tumors (Drebin et al.,1986; Drebin et al., 1985). The clinical success of the Her2-antibody therapy was an excellent example of the translation of basic cancer biology into clinical cancer treatment. However, the antibody therapy alone may not be ideal for therapeutic intervention of Her2-overexpressing breast cancers. In theory, downregulation of Her2 may be accomplished efficiently by inhibiting the expression of the Her2 gene rather than targeting elevated levels of the Her2 proteins that are already overexpressed. By analogy with treatments for AIDS, cocktails of drugs—each with a different mechanisms of action—might also be more effective at achieving complete remission of breast tumors. Thus, discovering a means to provide external control over Her2 expression, particularly through small organic molecules, remains appealing.

The overexpression of Her2 can be accomplished through a combination of two different mechanisms: gene duplication and increased transcription. In both cases, excess Her2 mRNA is produced, and this process can be controlled at the level of gene transcription. In search of transcription factors that activate the Her2 gene in breast cancers, Chang et al. and others have identified the Ets factor ESX (epithelial-restricted with serine box) (Chang et al., 1997). ESX is overexpressed in Her2-overexpressing breast cancer cells, and it binds and strongly transactivates the promoter of the Her2 gene. Deletion of the ESX-binding element from the Her2 promoter completely abolishes its activation, suggesting the importance of ESX in activating the Her2 gene in cells (Scott et al., 1994). The expression of ESX is epithelial specific and high in mammalian gland, trachea, prostate, and stomach (Andreoli et al., 1997). ESX may be a unique transcription factor that controls expression of Her2 in these tissues.

Current drug therapy addresses only about 500 molecular targets. Cell membrane receptors and enzymes account for ~80% of all current drug targets, and there are few drug targets in the nucleus except nuclear receptors (and DNA in the case of cancer chemotherapy) (Drews et al., 2000). Discovering new molecular targets in the nucleus would extend the scope of drug targets and might provide alternative therapeutic strategies to treat major human diseases. For instance, recent discovery of histone deacetylases as a potential target for cancer therapy had tremendous impacts on the drug discovery research (Kwon et al., 1998; Hassing et al., 1997; Taunton et al., 1996; Lin et al., 1998). The potentiality of transcriptional co-activators as a drug target has never been explored due to the lack of expected therapeutic phenotypes. A subset of co-activators, although not all, may serve as a target for pharmaceutical intervention.

Complete analysis of the human genome is anticipated to produce an unprecedented number of potential drug targets. Among these genomic pseudo-targets, the "relatively easy" targets such as GPCRs or enzymes will certainly be an immediate focus in pharmaceutical industries. However, more challenging genomic targets including protein-protein interactions need to be assessed for a leap of pharmaceutical development in the future.

Protein-protein interactions are harder to target by small organic molecules than enzymes or nuclear hormone receptors. Protein-protein binding typically occurs over a relatively large surface area, and the binding surfaces between two proteins tend to be flat and often lack in pockets that might provide binding sites suited for small organic molecules. Nevertheless, protein-protein interfaces vary widely in nature from one to another, and some are likely to present better druggability than others. A good example is the interaction between the somatostatin receptor and β-turn peptide ligands.

Recent studies suggest that the protein-protein interactions that are mediated by short α-helical segments of proteins are similarly tractable to inhibition by small nonpeptidic molecules. Helical peptide segments of proteins are responsible for a number of biologically important protein associations in the fields of signal transduction and gene transcription. The interaction between the two cancer-linked nuclear proteins, ESX (an epithelial-specific transcription factor) and Sur-2/DRIP130 (a Ras-linked subunit of the human mediator complex) is required for the overexpression of the Her2 oncogene in malignant breast cancer cells and thus serves as a potential therapeutic target for Her2-positive breast cancers amounting to 60,000 cases per year in the United States. The interaction is mediated by one face of an eight-amino acid-helical region in the transcriptional activation domain of ESX (SEQ ID NO: 1 Ser-Trp-Ile-Ile-Glu-Leu-Leu-Glu), and the tryptophan residue in the hydrophobic face of the helix makes a unique contribution to the specificity of the interaction. The relatively small size of the interface and the importance of the tryptophan residue suggested the existence of small-molecule inhibitors in a chemical library enriched in the structural families of indole, benzimidazole, and benzodiazepin-indole-mimicking π-electron-rich pharmacores found in bioavailable drugs.

BRIEF SUMMARY OF THE INVENTION

An object of the present invention is to provide small molecule Her2 expression inhibitors. In an embodiment of the invention, the Her2 expression inhibitors are peptide mimetics. In another embodiment of the invention, the Her2 expression inhibitors are α-helix mimetics of ESX. In an embodiment of the invention, the Her2 expression inhibitors are α-helix mimetics of SEQ ID NO:1. An embodiment of the invention is a compound of the formula:

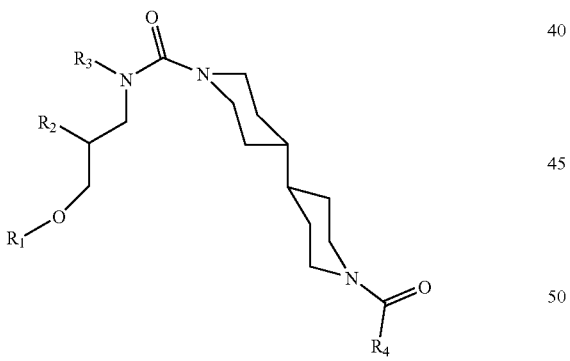

wherein $R_1$ is an indole, indole derivative, alkyl, trihaloalkyl, cycloalkyl, alkenyl, alkynyl, aryl, heteroaryl, heteroalicyclic, hydroxy, alkoxy, aryloxy, mercapto, alkylthio, arylthio, sulfinyl, sulfonyl, carbonyl, cyano, nitro, halo, or amino; wherein $R_2$ is a hydrogen, hydroxy, nitrate, halo, loweralkyl, or carbonyl; wherein $R_3$ is a halo, loweralkyl, carbonyl, aryl, aralkyl, or heterocycle; and wherein $R_4$ is an adamantane, adamantane derivative, alkyl, trihaloalkyl, cycloalkyl, alkenyl, alkynyl, aryl, heteroaryl, heteroalicyclic, hydroxy, alkoxy, aryloxy, mercapto, alkylthio, arylthio, sulfinyl, sulfonyl, S-sulfonamido, N-sulfonamido, trihalomethane-sulfonamido, halo, carbonyl, cyano, nitro, halo, or amino; and and wherein when $R_1$ is an indole, $R_2$ is a hydroxyl, and $R_3$ is an isopropyl, $R_4$ is not an adamantane; and pharmaceutically acceptable salts thereof In a specific embodiment, $R_4$ is a biphenyl. In another specific embodiment, $R_2$ is a hydroxyl group, and both racemates are contemplated. In another specific embodiment, $R_1$ is an indole, and the nitrogen on the indole has a tosyl substituent group.

A specific embodiment of the invention is a compound of the formula:

wherein $R_1$ and $R_2$ are a hydrogen, halo, alkyl, cycloalkyl, alkenyl, alkynyl, aryl, heteroaryl, heteroalicyclic, hydroxy, alkoxy, aryloxy, carbonyl, acetyl, carboxy, sulfonyl or trihalomethane-sulfonyl; and wherein $R_1$ and $R_2$ may be the same or different and are not both hydrogen; and pharmaceutically acceptable salts thereof.

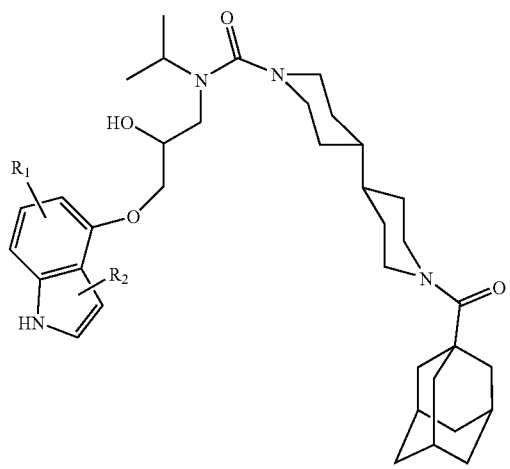

Another specific embodiment of the invention is a compound of the formula:

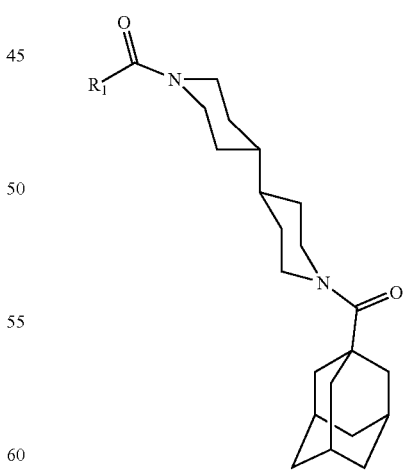

wherein the $R_1$ is selected from the group of β blockers consisting of propanolol, indenolol, carpindolol, bupranolol, and mepindolol; and pharmaceutically acceptable salts thereof. In a further specific embodiment of the invention, $R_1$ is propanolol.

Another specific embodiment of the invention is a compound of the formula:

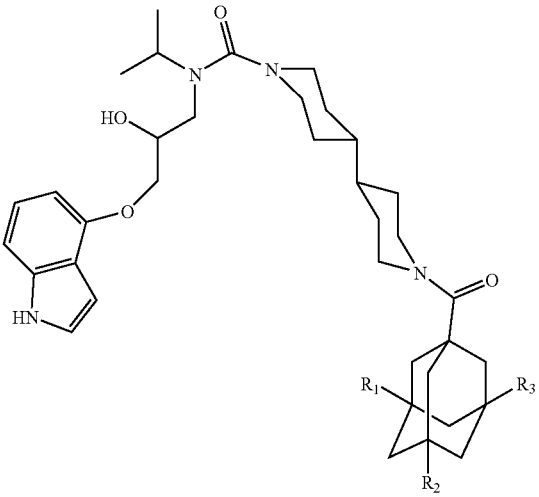

wherein $R_1$, $R_2$, and $R_3$ are a hydrogen, alkyl, cycloalkyl, alkenyl, alkynyl, aryl, heteroaryl, heteroalicyclic, hydroxy, alkoxy, aryloxy, carbonyl, halo, acetyl, carboxy, sulfonyl or trihalomethane-sulfonyl; and wherein $R_1$, $R_2$, and $R_3$ may be the same or at least one is different and are not all hydrogen; and pharmaceutically acceptable salts thereof.

A further embodiment of the invention is a compound of the formula:

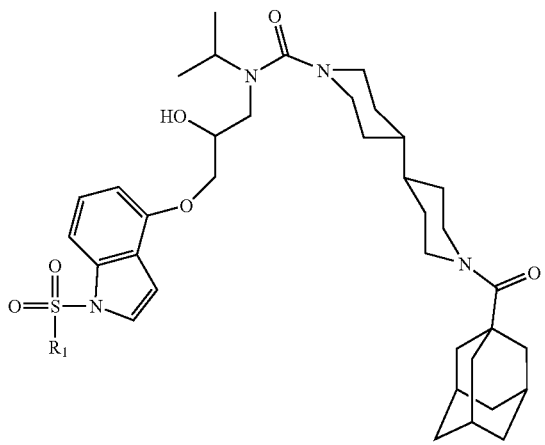

wherein $R_1$ is a hydrogen, alkyl, cycloalkyl, alkenyl, alkynyl, aryl, heteroaryl, heteroalicyclic, hydroxy, alkoxy, aryloxy, halo, carbonyl, acetyl, carboxy, sulfonyl or trihalomethane-sulfonyl. In further specific embodiments of the invention, $R_1$ is a methyl group, a benzene group, a phenyl, a toluene, a biphenyl, or a naphthalate.

A compound of the formula:

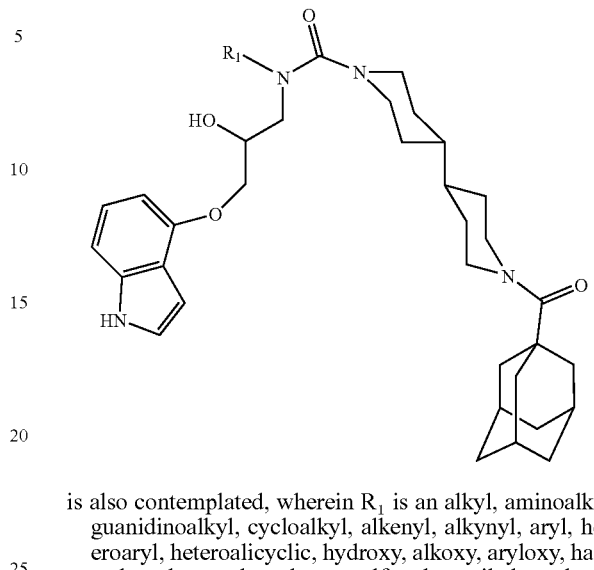

is also contemplated, wherein $R_1$ is an alkyl, aminoalkyl, guanidinoalkyl, cycloalkyl, alkenyl, alkynyl, aryl, heteroaryl, heteroalicyclic, hydroxy, alkoxy, aryloxy, halo, carbonyl, acetyl, carboxy, sulfonyl or trihalomethane-sulfonyl; and $R_1$ is not an isopropyl; and pharmaceutically acceptable salts thereof. In further specific embodiments of the invention, $R_1$ is hydrocarbon chain with 2, 3, 4, or 5 carbons. In further specific embodiments, the hydrocarbon chain may terminate in a hydroxyl group or an amine group.

An embodiment of the invention is a method of treating breast cancer in a mammal wherein a clinically effective amount of a small molecule inhibitor of Her2 expression is administered to said mammal. A specific embodiment of the invention is a method of treating breast cancer in a mammal, wherein a clinically effective amount of adamanolol, a functionalized adamanolol derivative, or a pharmaceutically acceptable salt thereof is administered to said mammal.

An embodiment of the invention is a compound of the formula:

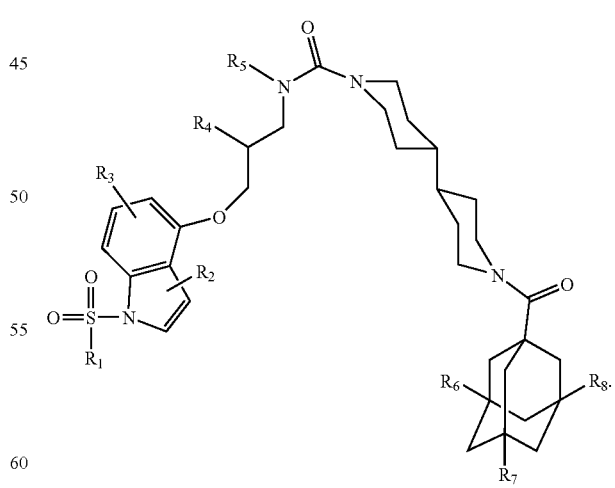

wherein $R_1$, $R_2$, $R_3$, $R_4$, $R_5$, $R_6$, $R_7$, and $R_8$ are a hydrogen, hydroxy, alkyl, trihaloalkyl, cycloalkyl, alkenyl, alkynyl, aryl, heteroaryl, heteroalicyclic, hydroxy, alkoxy, aryloxy, mercapto, alkylthio, arylthio, sulfinyl, sulfonyl, carbonyl, cyano, nitro, halo, or amino; and wherein $R_1$, $R_2$, $R_3$, $R_4$, $R_5$, $R_6$, $R_7$, and $R_8$ may be the same or different; and pharmaceutically acceptable salts thereof.

An embodiment of the invention is a compound of the formula:

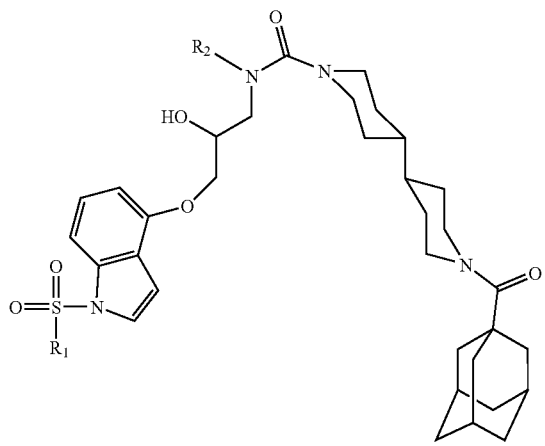

wherein $R_1$ is a hydrogen, halo, alkyl, cycloalkyl, alkenyl, alkynyl, aryl, heteroaryl, heteroalicyclic, hydroxy, alkoxy, aryloxy, carbonyl, acetyl, carboxy, sulfonyl or trihalomethane-sulfonyl; $R_2$ is a halo, loweralkyl, carbonyl, aryl, aralkyl, or heterocycle; wherein $R_1$ and $R_2$ may be the same or different; and pharmaceutically acceptable salts thereof.

An embodiment of the invention is a compound of the formula:

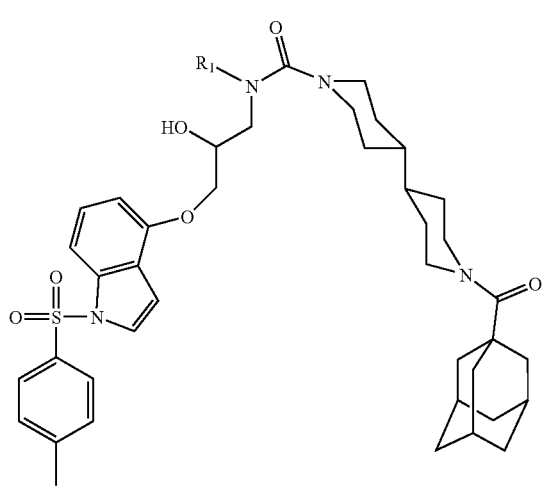

wherein $R_1$ is a halo, loweralkyl, carbonyl, aryl, aralkyl, or heterocycle; and pharmaceutically acceptable salts thereof.

An embodiment of the invention is a compound of the formula:

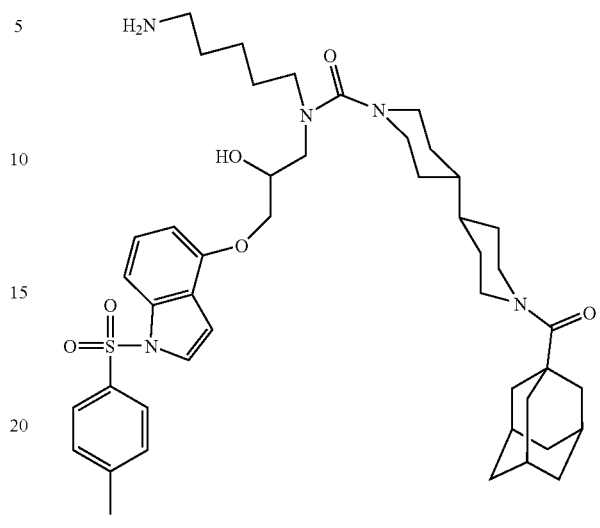

An embodiment of the invention is a compound of the formula:

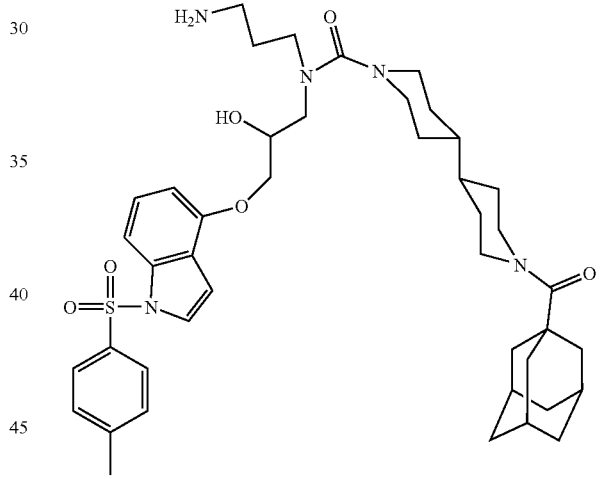

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIG. 2A shows an SDS-PAGE gel of the purified Sur-2. FIG. 2B shows that in vitro translated Sur-2 binds the ESX activation domain, but not its activation-deficient mutant. FIG. 2C shows Sur-2 binds specifically to the ESX activation domain;

FIG. 3 demonstrates the identification of a small Sur-2 domain that binds the ESX activation domain.

FIG. 5A depicts results of incubating four breast cancer cell lines with TAT-$ESX_{129-145}$. FIG. 5B shows the nuclear condensation induced by TAT-$ESX_{129-145}$ FIG. 5C indicates Her2 overexpression in the three breast cancer lines tested. FIG. 5D indicates that MCF-7 Her18, a Her2 overexpressing cell line, was resistant to $ESX_{129-145}$;

FIG. 7 shows NMR data for $ESX_{129-145}$.

FIG. 8 show the eight amino-acid segment of ESX that interacts with Sur-2. FIG. 8B is a summary of mutational studies. Point mutants of $ESX_{129-145}$ were tested for their ability to bind Sur-2. The indole structure of Trp138 was substituted with Ala, Phe, or Leu, which abolished the interaction with Sur-2.

FIG. 9A shows that adamanolol selectively inhibits the ESX activation domain. FIG. 9B shows that adamanolol selectively impairs the cell growth and viability of Her2-expressing breast cancer cells. FIG. 9C is a western blot showing the inhibition of Her2 by adamanolol. FIG. 9D shows that adamanolol inhibits the ESX-Sur-2 interaction in vitro.

FIG. 20A illustrates the wrench-like structure of wrenchnolol (compound 7b). FIG. 20B shows that wrenchnolol selectively impairs the ability of the ESX activation domain to activate the secreted alkaline phosphatase reporter gene in HEK293 cells, whereas 4d has little effects on the transcriptional activation. FIG. 20C shows inhibition of Her2 protein expression by wrenchnolol;

FIG. 21A to FIG. 21C show NMR analysis of compound 7a. FIG. 21A shows an expanded region of a NOESY spectrum of compound 7a. FIG. 21B shows the chemical structure of compound 7a with a summary of key NOE connectivities. FIG. 21C shows a tertiary geometry model of compound 7a;

FIG. 22A shows the expanded 1D $^1$H NMR spectra of wrenchnolol in the presence or absence of GST-$Sur_{352-625}$. FIG. 22B shows a summary of the differential signal intensities;

FIG. 23A shows Western blot detection of Sur-2 protein. FIG. 23B shows silver staining of the bound proteins. The 130 KDa band indicated by an arrow matched the western-blotted band shown in FIG. 23A;

FIG. 24A shows an evaluation of cell permeability of wrenchnolol. FIG. 24B shows co-staining of the cells with nucleus-specific DAPI dye. FIG. 24C shows the estimation of $K_d$ of the wrenchnolol-Sur-2 interaction.

DETAILED DESCRIPTION OF THE INVENTION

Figure 1:
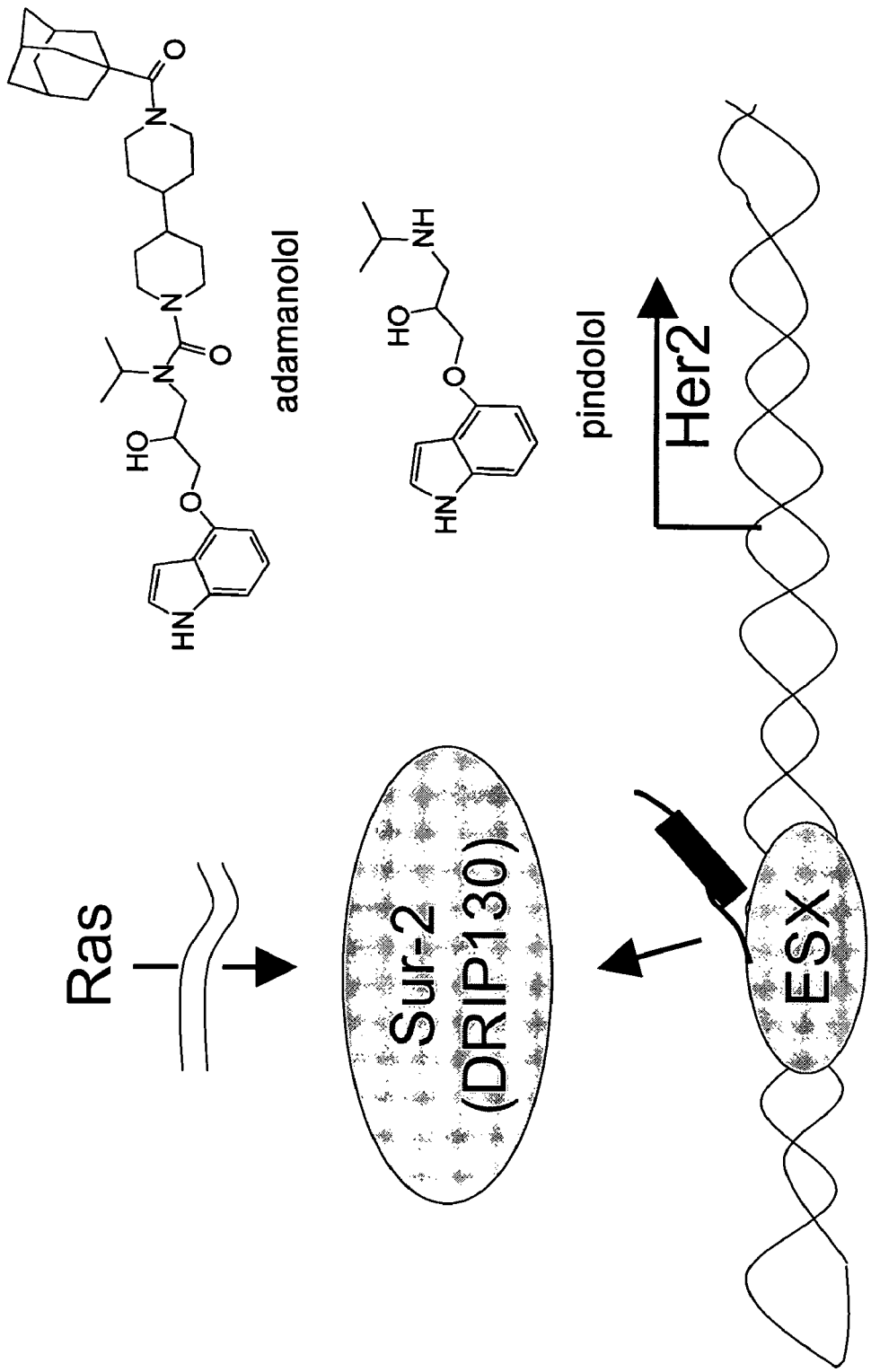
FIG. 1 demonstrates the interaction between Sur-2 and ESX and its role in regulating Her-2 expression.

It is readily apparent to one skilled in the art that various embodiments and modifications can be made to the invention disclosed in this Application without departing from the scope and spirit of the invention.

As used herein, the use of the word "a" or "an" when used in conjunction with the term "comprising" in the sentences and/or the specification may mean "one," but it is also consistent with the meaning of "one or more," "at least one," and "one or more than one." As used herein "another" may mean at least a second or more. Still further, the terms "having", "including", "containing" and "comprising" are interchangeable and one of skill in the art is cognizant that these terms are open ended terms.

As used herein, "DRIP-130" is interchangeable with "Sur-2". "Sur-2" is a Ras-linked subunit of the human mediator complex and comprises SEQ ID NO: 2.

As used herein "inhibition of Her2 expression" refers to inhibition of the interaction of Sur-2 with ESX, which regulates Her2 expression. A consequence of Sur-2 inhibition is the decreased transcription of Her2. Thus, Sur2 inhibition results in inhibition of Her2 expression.

As used herein, a "mammal" is an appropriate subject for the method of the present invention. A mammal may be any member of the higher vertebrate class Mammalia, including humans; characterized by live birth, body hair, and mammary glands in the female that secrete milk for feeding the young. Additionally, mammals are characterized by their ability to maintain a constant body temperature despite changing climatic conditions. Examples of mammals are humans, cats, dogs, cows, mice, rats, and chimpanzees. Mammals may be referred to as "patients".

"Peptide" refers to a polymer in which the monomers are amino acids and are joined together through amide bonds, alternatively referred to as a polypeptide. When the amino acids are α-amino acids, either the L-optical isomer or the D-optical isomer can be used. Additionally, unnatural amino acids, for example, beta-alanine, phenylglycine and homoarginine are also included. The amino acids may be either the D- or L-isomer. The L-isomers are generally preferred. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

As used herein, a "peptide mimetic" is a compound that biologically mimics determinants on hormones, cytokines, enzyme substrates, viruses or other bio-molecules, and may antagonize, stimulate, or otherwise modulate the physiological activity of the natural ligands. Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule. Molecules are designed to recognize amino acid residues in alpha-helix or beta-turn conformations on the surface of a protein. Such molecules may be used in disrupting certain protein-protein interactions involved in disease. In a the present invention, novel compounds are described that inhibit Sur-2. These compounds are alpha-helix mimetics of Sur-2. In a specific embodiment, the inhibitors mimic an eight amino acid (SEQ ID NO: 1) alpha-helical domain of ESX that interacts with Sur-2. One with skill in the art realizes that other alpha-helical domains of ESX may be appropriate targets for small molecule peptide mimetics.

"Protein", as used herein, means any protein, including, but not limited to peptides, polypeptides, enzymes, glycoproteins, hormones, receptors, antigens, antibodies, growth factors, etc., without limitation. Presently preferred proteins include those comprised of at least 25 amino acid residues, more preferably at least 35 amino acid residues and still more preferably at least 50 amino acid residues.

Any compounds of this invention containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations. Some of the compounds of the invention can exist in more than one tautomeric form. The invention includes all such tautomers. The compounds of the invention are only those which are contemplated to be chemically stable as will be appreciated by those skilled in the art. For example, a compound which would have a dangling valency, or a carbanion are not compounds contemplated by the invention. Any of the aromatic ring systems, carbocyclic or heterocyclic, shall be understood to include the non-aromatic ring systems which may be mono- or polyunsaturated, and the positional isomers or analogs thereof. Any of the compounds described herein possessing "nitrogen" and "sulfur" shall include any oxidized form of nitrogen and sulfur and the quaternized form of any basic nitrogen. Unless otherwise defined herein, all nomenclature is as standard in the art.

1. Chemical Definitions and Derivatives

A. Adamanolol

"Adamanolol" as used herein is defined as a compound consisting of the formula:

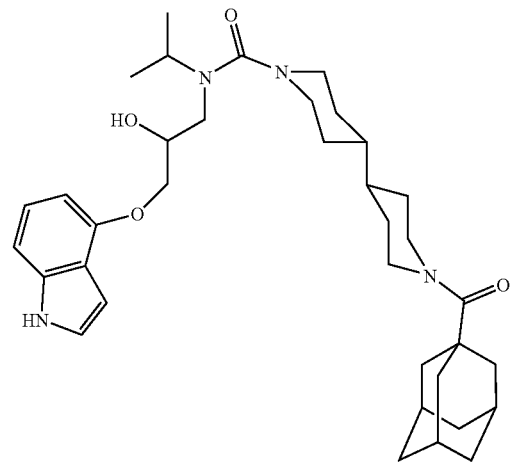

The chemical name for adamanolol is 1'-(adamantane-1-carbonyl)-[4,4']bipiperidinyl-1-carboxylic acid [2-hydroxy-3-3-(1H-indol-4-yloxy)-propyl]-isopropyl-amide.

"Functionalized adamanolol derivatives" as used herein describe small molecule chemical compound derivatives of adamanolol which retain the Sur-2 inhibition activity of the adamanolol compound, and are generally of the formula:

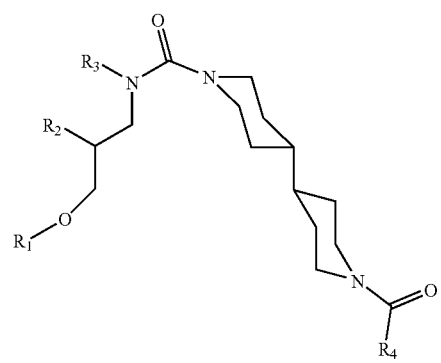

wherein $R_1$ is an indole, indole derivative, alkyl, trihaloalkyl, cycloalkyl, alkenyl, alkynyl, aryl, heteroaryl, heteroalicyclic, hydroxy, alkoxy, aryloxy, mercapto, alkylthio, arylthio, sulfinyl, sulfonyl, carbonyl, cyano, nitro, halo, or amino;

wherein $R_2$ is a hydrogen, hydroxy, nitrate, halo, lower-alkyl, or carbonyl;

wherein R₃ is a halo, loweralkyl, carbonyl, aryl, aralkyl, or heterocycle;

and wherein R₄ is adamantane, adamantane derivative, alkyl, trihaloalkyl, cycloalkyl, alkenyl, alkynyl, aryl, heteroaryl, heteroalicyclic, hydroxy, alkoxy, aryloxy, mercapto, alkylthio, arylthio, sulfinyl, sulfonyl, S-sulfonamido, N-sulfonamido, trihalomethane-sulfonamido, halo, carbonyl, cyano, nitro, halo, or amino.

One with skill in the art realizes that the magnitude of Her2 expression inhibition may vary among functionalized derivatives. In certain embodiments of the invention, the Her2 expression inhibition of the functionalized adamanolol derivatives is less than that of adamanolol, and in other embodiments of the invention the Her2 expression inhibition of the functionalized adamanolol derivatives is greater than that of adamanolol.

B. Indoles

Indole is a colorless crystalline solid. The heat of combustion at constant volume is 4,268 MJ/mol (1020 kcal/mol). The molecule is planar and has only moderate polarity. Indole has good solubility in a wide range of solvents including petroleum ether, benzene, chloroform, and hot water. Indole forms salts with high concentrations of both strong bases and strong acids. With strong bases, the anion is stabilized by delocalization of the electron over the aromatic system and indole, with a pK for deprotonation of 16.97, is a stronger acid than simple amines. Conversely, because the lone pair of electrons on the nitrogen atom is an integral part of the aromatic system, indole is a much weaker base when combined with strong acids than the alkylamines or pyridine and gives a pK value of −3.5 for protonation. The protonation occurs at the N1 or C3 positions and gives the indolium ion or indoleninium ion.

Spectroscopic evidence indicates that in strong sulfuric or perchloric acid, protonation occurs at the C3 position. The formation of dimers and trimers complicates the situation and, except for 2-substituted indoles (which, for steric reasons, do not dimerize), an equilibrium exists between the indole, the dimer, the trimer, and their salts. The term "indole derivative" or "substituted indole" as used herein refers to compounds of the general formula:

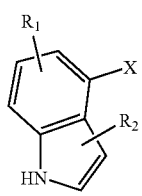

wherein R₁ and R₂ may be a hydrogen, halo, alkyl, cycloalkyl, alkenyl, alkynyl, aryl, heteroaryl, heteroalicyclic, hydroxy, alkoxy, aryloxy, carbonyl, acetyl, carboxy, sulfonyl or trihalomethane-sulfonyl, and may be the same or different. In other embodiments of the invention. It is contemplated the ring nitrogen may be substituted, and the substituent group may be a hydrogen, halo, alkyl, cycloalkyl, alkenyl, alkynyl, aryl, heteroaryl, heteroalicyclic, hydroxy, alkoxy, aryloxy, carbonyl, acetyl, carboxy, sulfonyl or trihalomethane-sulfonyl, and where R₁ and R₂ are not both hydrogen. The term "indole" or "unsubstituted indole" refers the compound of the above formula when R₁ and R₂ are both hydrogen.

X represents the site of attachment of the indole to the adamanolol or functionalized adamanolol derivative.

C. Beta-Blockers

The beta-blockers comprise a group of drugs that are indicated for use to treat cardiovascular disorders. Nonselective beta-blockers, including propranolol, oxprenolol, pindolol, nadolol, timolol and labetalol, antagonize both β1- and β2-adrenergic receptors. A common feature in the chemical structure of beta-blockers is that there is at least one aromatic ring structure that is attached to a side alkyl chain possessing a secondary hydroxyl and amine functional group. Each of the available beta-blockers has one or more chiral centers in its structure, and in all cases, at least one of the chiral carbon atoms residing in the alkyl side chain is directly attached to a hydroxyl group. Each of the beta-blockers with one chiral center (e.g., propranolol, metoprolol, atenolol, esmolol, pindolol, and acebutolol), except for timolol, is sold as a racemate.

One with skill in the art realizes that although the functionalized adamanolol derivatives have, in certain embodiments, beta blocker side group substituents, these small molecule derivatives are functionally distinct from beta blockers, and exhibit different pharmacologic activity.

D. Adamantane and Derivatives.

One with skill in the art realizes that adamantane is tricyclo (3,3,1,1³,⁷) decane, also described by CAS No.(281-23-2) and EINECS No. (206-001-4). The ten carbon atoms which define the framework structure are arranged in an essentially strainless manner thereby giving a very stable backbone for the addition of a variety of moieties. Four of these carbon atoms, the bridgehead carbons, are tetrahedrally disposed about the center of the molecule. The other six (methylene carbons) are octahedrally disposed. Because of the particular reactivity of adamantane, functional groups have been readily introduced at the bridgehead 1-, 3-, 5-, 7-positions of adamantane. In the present invention, the adamantane group is linked to adamanolol at the 1-position. U.S. Pat. No. 5,019,660 to Chapman and Whitehurst and U.S. Pat. No. 5,053,434 to Chapman teach diamondoid compounds which bond through the methylene positions of various diamondoid compounds. For a survey of the chemistry of diamondoid molecules, see Adamantane, The Chemistry of Diamond Molecules, Raymond C. Fort, Marcel Dekker, New York, 1976. For synthesis methods for adamantanes, see Paul Schleyer, Cage Hydrocarbons, George A. Olah, ed., Wiley, NEW YORK, 1990.

In specific embodiments, the compound of the formula:

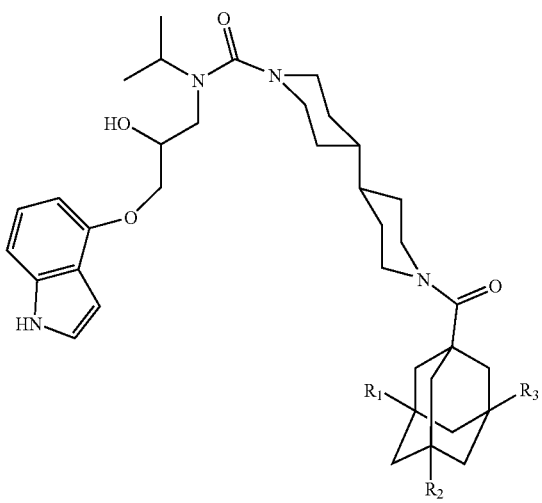

is contemplated.

wherein the adamantane group may be a substituted adamantane derivative such as 1-adamantanol, 1-adamantane carboxylic acid, 1-adamantyl methyl ketone, adamantanone, adamantanol, or 1-bromoadamantane. $R_1$, $R_2$, and $R_3$ may be a hydrogen, alkyl, cycloalkyl, alkenyl, alkynyl, aryl, heteroaryl, heteroalicyclic, hydroxy, alkoxy, aryloxy, carbonyl, halo, acetyl, carboxy, sulfonyl or trihalomethane-sulfonyl, and where $R_1$, $R_2$, and $R_3$ may be the same or at least one is different, i.e. all may be different or one may be different. If $R_1$, $R_2$, and $R_3$ are all hydrogen, the group is an "adamantane" or "unsubstituted adamantane". When $R_1$, $R_2$, and $R_3$ are not all hydrogen, the group is an "adamantane derivative" or "substituted adamantane".

E. Additional Side Group Substituents

It is contemplated that the functionalized adamanolol derivatives have substituent groups. In specific embodiments, the definitions of those groups are as below.

The term "alkyl" as used herein refers to a straight, branched, or cyclic hydrocarbon chain fragment or radical containing between about one and about twenty carbon atoms, more preferably between about one and about ten carbon atoms (e.g., methyl, ethyl, n-propyl, iso-propyl, cyclopropyl, n-butyl, iso-butyl, tert-butyl, cyclobutyl, adamantyl, noradamantyl and the like). Straight, branched, or cyclic hydrocarbon chains having eight or fewer carbon atoms will also be referred to herein as "loweralkyl". The hydrocarbon chains may further include one or more degrees of unsaturation, i.e., one or more double or triple bonds (e.g., vinyl, propargyl, allyl, 2-buten-1-yl, 2-cyclopenten-1-yl, 1,3-cyclohexadien-1-yl, 3-cyclohexen-1-yl and the like). Alkyl groups containing double bonds such as just described will also be referred to herein as "alkenes". Similarly, alkyl groups having triple bonds will also be referred to herein as "alkynes". However, as used in context with respect to cyclic alkyl groups, the combinations of double and/or triple bonds do not include those bonding arrangements that render the cyclic hydrocarbon chain aromatic.

The term "oxo" means a doubly bonded oxygen.

In addition, the term "alkyl" as used herein further includes one or more substitutions at one or more carbon atoms of the hydrocarbon fragment or radical. Such substitutions include, but are not limited to: aryl; heterocycle; halogen (to form, e.g., trifluoromethyl, —$CF_3$); nitro (—$NO_2$); cyano (—CN); hydroxyl (also referred to herein as "hydroxy"), alkoxyl (also referred to herein as alkoxy) or aryloxyl (also referred to herein as "aryloxy", —OR); thio or mercapto, alkyl, or arylthio (—SR); amino, alkylamino, arylamino, dialkyl- or diarylamino, or arylalkylamino (—NRR'); aminocarbonyl, alkylaminocarbonyl, arylaminocarbonyl, dialkylaminocarbonyl, diarylaminocarbonyl or arylalkylaminocarbonyl (—C(O)NRR'); carboxyl, or alkyl-oraryloxycarbonyl (—C(O)OR); carboxaldehyde, or aryl- or alkylcarbonyl (—C(O)R); iminyl, aryl- or alkyliminyl; sulfo (—$SO_2$OR); alkyl- or arylsulfonyl (—$SO_2$R); carbamido; orthiocarbamido; where R and R' independently are hydrogen, aryl or alkyl as defined herein. Substituents including heterocyclic groups (i.e., heterocycle, heteroaryl, and heteroaralkyl) are defined by analogy to the above-described terms. For example, the term "heterocycleoxy" refers to the group —OR, where R is heterocycle as defined below. Examples of some alkyl amine substituents contemplated in the present invention are primary alkyl amines such as methyl amine, ethyl amine, propyl amine, butyl amine, pentyl amine, and hexyl amine.

The term "methylene" refers to the group —$CH_2$—.

The term "methine" refers to a methylene group for which one hydrogen atom has been replaced by a substituent as described above. The term "methine" can also refer to a methylene group for which one hydrogen atom is replaced by bond to form a hybridized carbon center.

The term "halo" or "halogen" as used herein refers to the substituents fluoro, bromo, chloro, and iodo.

The term "carbonyl" as used herein refers to the functional group —C(O)—. However, it will be appreciated that this group may be replaced with well-known groups that have similar electronic and/or steric character, such as thiocarbonyl (—C(S)—); sulfinyl (—S(O)—); sulfonyl (—$SO_2$—) phosphonyl (—$PO_2$—), and methine. Other carbonyl equivalents will be familiar to those having skill in the medicinal and organic chemical arts.

The term "aryl" as used herein refers to cyclic aromatic hydrocarbon chains having twenty or fewer carbon atoms, e.g., phenyl, naphthyl, biphenyl and anthryl. One or more carbon atoms of the aryl group may also be substituted with, e.g.: alkyl; aryl; heterocycle; halogen; nitro; cyano; hydroxyl, alkoxyl or aryloxyl; thio or mercapto, alkyl-, or arylthio; amino, alkylamino, arylamino, dialkyl-, diaryl-, or arylalkylamino; aminocarbonyl, alkylaminocarbonyl, arylaminocarbonyl, dialkylaminocarbonyl, diarylaminocarbonyl or arylalkylaminocarbonyl; carboxyl, or alkyl- or aryloxycarbonyl; carboxaldehyde, or aryl- or alkylcarbonyl; iminyl, or aryl- or alkyliminyl; sulfo; alkyl- or arylsulfonyl; hydroximinyl, or aryl- or alkoximinyl; carbamido; or thiocarbamido. In addition, two or more alkyl or heteroalkyl substituents of an aryl group may be combined to form fused aryl-alkyl or aryl-heteroalkyl ring systems (e.g., tetrahydronaphthyl). Substituents including heterocyclic groups (e.g., heterocycleoxy, heteroaryloxy, and heteroaralkylthio) are defined by analogy to the above-described terms.

The term "aralkyl" as used herein refers to an aryl group that is joined to a parent structure by an alkyl group as described above, e.g., benzyl, .alpha.-methylbenzyl, phenethyl, and the like.

The term "heterocycle" as used herein refers to a cyclic alkyl group or aryl group as defined above in which one or more carbon atoms have been replaced by a non-carbon atom, especially nitrogen, oxygen, or sulfur. Non-aromatic heterocycles will also be referred to herein as "cyclic heteroalkyl". Aromatic heterocycles are also referred to herein as "heteroaryl". For example, such groups include furyl, tetrahydrofuryl, pyrrolyl, pyrrolidinyl, thienyl, tetrahydrothienyl, oxazolyl, isoxazolyl, triazolyl, thiazolyl, isothiazolyl, pyrazolyl, pyrazolidinyl, oxadiazolyl, thiadiazolyl, imidazolyl, imidazolinyl, pyridyl, pyridazinyl, triazinyl, piperidinyl, morpholinyl, thiomorpholinyl, pyrazinyl, piperazinyl, pyrimidinyl, naphthyridinyl, benzofuranyl, benzothienyl, indolyl, indolinyl, indolizinyl, indazolyl, quinolizinyl, quinolinyl, isoquinolinyl, cinnolinyl, phthalazinyl, quinazolinyl, quinoxalinyl, pteridinyl, quinuclidinyl, carbazolyl, acridinyl, phenazinyl, phenothiazinyl, phenoxazinyl, purinyl, benzimidazolyl, benzthiazolyl, and benzoxazolyl.

The above heterocyclic groups may further include one or more substituents at one or more carbon and/or non-carbon atoms of the heteroaryl group, e.g.: alkyl; aryl; heterocycle; halogen; nitro; cyano; hydroxyl, alkoxyl or aryloxyl; thio or mercapto, alkyl- or arylthio; amino, alkyl-, aryl-, dialkyl-diaryl-, or arylalkylamino; aminocarbonyl, alkylaminocarbonyl, arylaminocarbonyl, dialkylaminocarbonyl, diarylaminocarbonyl or arylalkylaminocarbonyl; carboxyl, or alkyl- or aryloxycarbonyl; carboxaldehyde, or aryl- or alkylcarbonyl; iminyl, or aryl- or alkyliminyl; sulfo; alkyl- or arylsulfonyl; hydroximinyl, or aryl- or alkoximinyl; carbamido; or thiocarbamido. In addition, two or more alkyl substituents may be combined to form fused heterocycle-alkyl or heterocycle-aryl ring systems. Substituents including heterocyclic groups (e.g., heterocycleoxy, heteroaryloxy, and heteroaralkylthio) are defined by analogy to the above-described terms.

The term "heterocyclealkyl" refers to a heterocycle group that is joined to a parent structure by one or more alkyl groups as described above, e.g., 2-piperidylmethyl, and the like. The term "heteroaralkyl" as used herein refers to a heteroaryl group that is joined to a parent structure by one or more alkyl groups as described above, e.g., 2-thienylmethyl, and the like.

The term "tosyl" or "Ts" refers to p-toluenesulfonate, shown below. It is the conjugate base of the strong acid, p-toluenesulfonic acid. Sulfonate esters are compounds having the sulfonate group, —O—S(=O)(=O), wherein the single bonded oxygen is bonded directly to carbon, which carbon may be single bonded to any atom but may be multiple bonded only to carbon. The term "mesyl" or "Ms" refers to a mesyl group, which is a sulfonate ester having the formula $CH_3SO_2$—.

2. Salts and Esters for Pharmaceutical Use

Non-toxic esters and salts which are generally prepared by reacting the free base with a suitable organic or inorganic acid are suitable for pharmaceutical use. Representative salts and esters include the following: Acetate, Lactobionate, Benzenesulfonate, Laurate, Benzoate, Malate, Bicarbonate Maleate, Bisulfate Mandelate, Bitartrate, Mesylate, Borate, Methylbromide, Bromide, Methylnitrate, Calcium Edetate, Methylsulfate, Camsylate, Mucate, Carbonate, Napsylate, Chloride, Nitrate, Clavulanate, N-methylglucamine, Citrate, ammonium salt, Dihydrochloride, Oleate, Edetate, Oxalate, Edisylate, Pamoate (Embonate), Estolate, Palmitate, Esylate, Pantothenate, Fumarate, Phosphate/diphosphate, Gluceptate, Polygalacturonate, Gluconate, Salicylate, Glutamate, Stearate, Glycollylarsanilate, Sulfate, Hexylresorcinate, Subacetate, Hydrabamine, Succinate, Hydrobromide, Tannate, Hydrochloride, Tartrate, Hydroxynaphthoate, Teoclate, Iodide, Tosylate, Isothionate, Triethiodide, Lactate, Trifluoroacetate, and Valerate.

3. Pharmaceutical Preparations

Pharmaceutical compositions of the present invention comprise an effective amount of at least one Sur-2 inhibitors or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one Sur-2 inhibitors or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The Sur-2 inhibitors (Her2 expression inhibitors) may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostatically, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g. aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The Sur-2 inhibitors may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistarnines.

In certain embodiments the Sur-2 inhibitor is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

4. Breast Cancer Treatment

In the present invention, small molecule inhibitors of Sur-2 are provided which target Her2-expressing breast cancer cells. "Breast cancer" means any of various carcinomas of the breast or mammary tissue. In certain embodiments, it is contemplated that Sur-2 inhibitors will comprise a component of a chemotherapy and radiation treatment regimen in the treatment of breast cancer. Management of the breast cancer currently relies on a combination of early diagnosis through routine breast screening procedures and aggressive treatment. Such treatment may include surgery, radiotherapy, chemotherapy, hormone therapy or combinations of these therapies. Examples of drug treatments currently available for breast cancer include tamoxifen, adriamycin, letrozole, and patritaxel.

In other embodiments, it is contemplated that small molecule inhibitors of Sur-2 may be useful in a prophylactic context.

Overexpression of Her2 has also been found in a portion of ovarian cancers, gastric cancers, endometrial cancers, salivary cancers, pancreatic cancers, prostate cancers, colorectal cancers, and non-small-cell lung cancers. The other cancers associated with overexpression of Her2 are potentially treatable with Sur-2 inhibitors.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

EXAMPLES

The below are nonlimiting examples of the present invention.

Example 1

Materials

HeLa S3 and MCF7 cells were purchased from American Type Culture Collection. K-BR3, MDA-MB453 and MDA-MB468, were kindly supplied by Dr. Mien-Chie Hung (M. D. Anderson Cancer Center, Houston, Tex.). MCF7, MCF7-HER18, SK-BR-3, MDA-MB-453, and MDA-MB-468 cells were grown in DMEM/F-12 medium with 10% FBS. Z. Songyang (Baylor College of Medicine) kindly supplied 293Tag cells. The cDNA plasmid construct of Sur-2 (pcDNA3-FLAG-Sur-2) was a kind gift from L. P. Freedman (Memorial Sloan-Kettering Cancer Center). Peptides were synthesized by the fluorenylmethoxycarbonyl chemistry by using Rink amide methylbenzhydrylamine resins, purified by HPLC, and characterized by electrospray ionization mass spectroscopy and/or NMR.

Example 2

Isolation of Sur-2 and Interaction with ESX

HeLa cell nuclear extracts were prepared as known in the art (Dignam, 1983). GST fusion proteins of the ESX activation domain or its activation-deficient mutant were obtained as described (Choi et al., 2000). The glutathione beads binding GST fusion protein or GST only were incubated with HeLa cell nuclear extracts and then extensively washed by buffer containing 20 mMTrisHCl (pH 7.5), 150 mM NaCl, and 0.1% Nonidet P-40. The bound proteins were separated by SDS/PAGE and stained with Coomassie brilliant blue R-250. The protein bands stained with Coomassie brilliant blue R-250 were excised from the gel and microsequenced by mass spectrometry as described. $S^{35}$-labeled DRIP130 proteins were prepared by TNT T7 Quick Coupled Transcription/translation system (Promega Corporation, Madison, Wis.). The glutathione beads binding to GST fusion protein or GST only were incubated with the in vitro translated proteins in 500 μl of binding buffer containing 100 mM NaCl, 0.4% Nonidet P-40, 10% glycerol, 20 mM TriszHCl (pH 7.5), 10 mM MgCl2, and 2 mM DTT for 1 h at 4° C. After extensive washing with the same buffer, the bound proteins were analyzed by SDS-PAGE.

Figure 2:
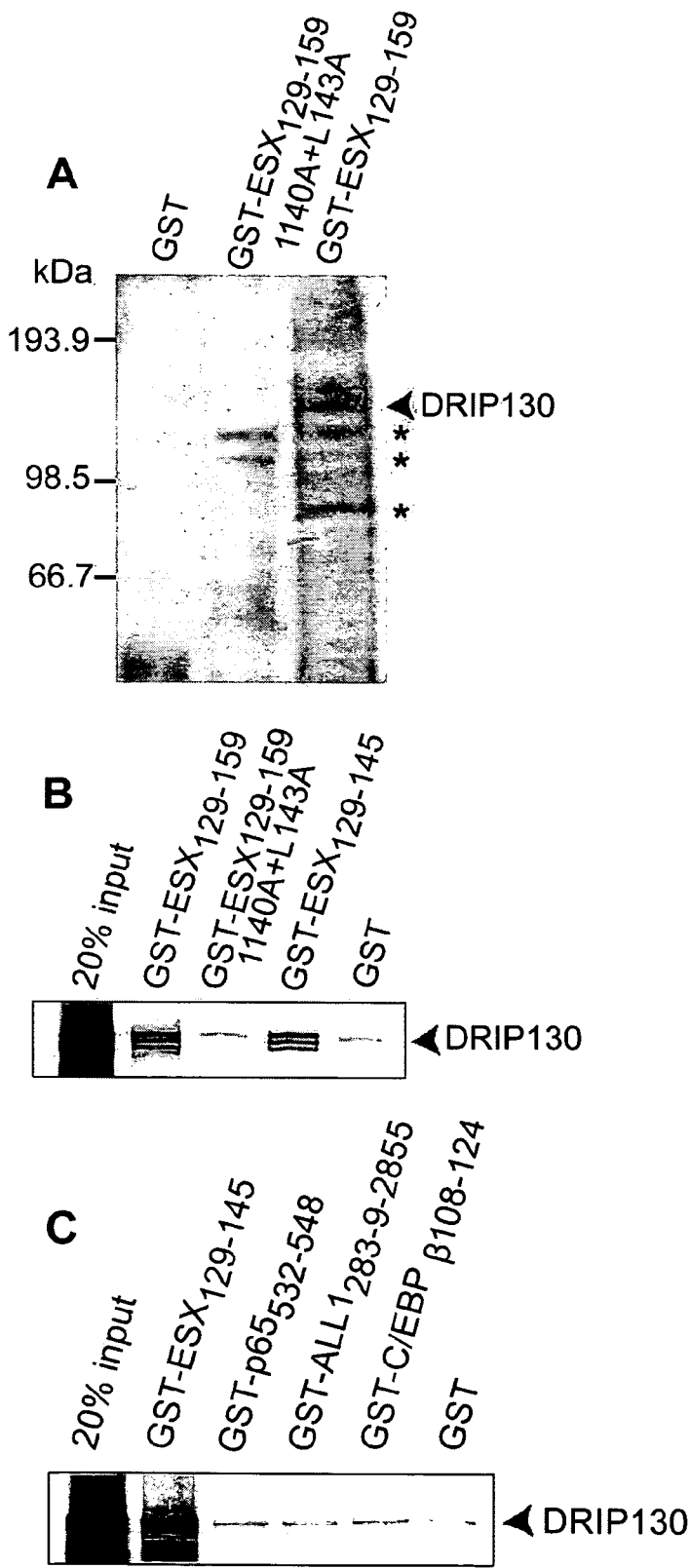
FIG. 2 shows the purification of Sur-2.

Human proteins that bound to the activation domain of ESX from HeLa nuclear extracts (FIG. 2A) were isolated. SDS-PAGE analyses of the isolated proteins showed that a 130-kDa protein bound tightly to the ESX activation domain but not to its activation-deficient mutant protein. Microsequencing data of a tryptic peptide matched to Sur-2 (DRIP130/CRSP130/Sur-2), a metazoan-specific component of the human mediator complexes known as DRIP (vitamin D receptor coactivator complex), CRSP (coactivator complex for Sp1), and ARC (activator-recruited cofactor) complexes. Other proteins that bound to the ESX activation domain (FIG. 2A) were abundant house-keeping proteins such as ATP-citrate lyase and 6-phosphofructokinase, and had affinity, although weaker, even to the activation-deficient mutant as revealed by silver staining of gels. In vitro translated Sur-2 bound to the ESX activation domain but not its activation-deficient mutant protein (FIG. 2B). The 17-aa segment of the ESX activation domain ($ESX_{129-145}$) was sufficient for mediating the interaction with Sur-2. Sur-2 seemed to recognize this short segment of ESX in a specific manner because Sur-2 had no detectable affinity to analogous to the 17-aa peptides from the activation domains of NF-kB p65, ALL1, and C/EBPβ(FIG. 2C). Sur-2 is a nuclear protein that binds specifically to the activation domain of ESX.

Example 3

Ectopic Expression of a Small Sur-2 Domain Impairs ESX

Figure 3A:
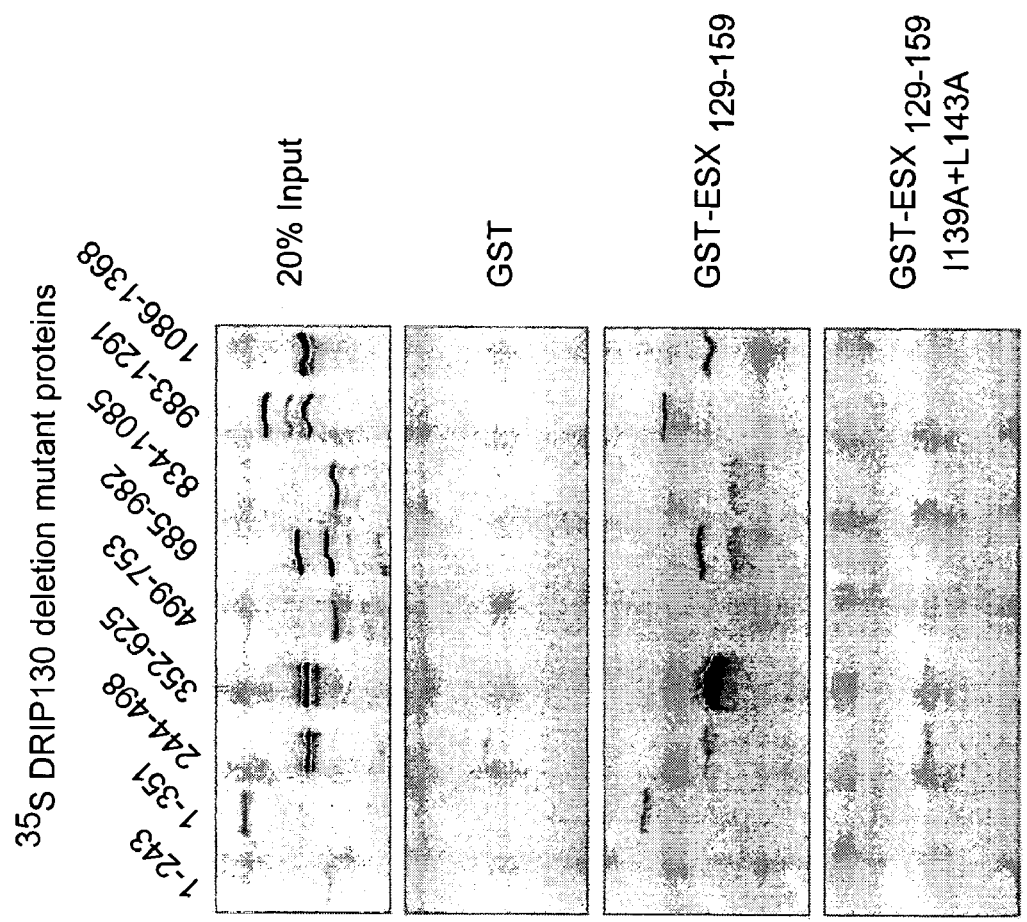
FIG. 3A demonstrates that a deletion mutant of Sur-2 maintained the ability to bind the ESX activation domain.
Figure 3B:
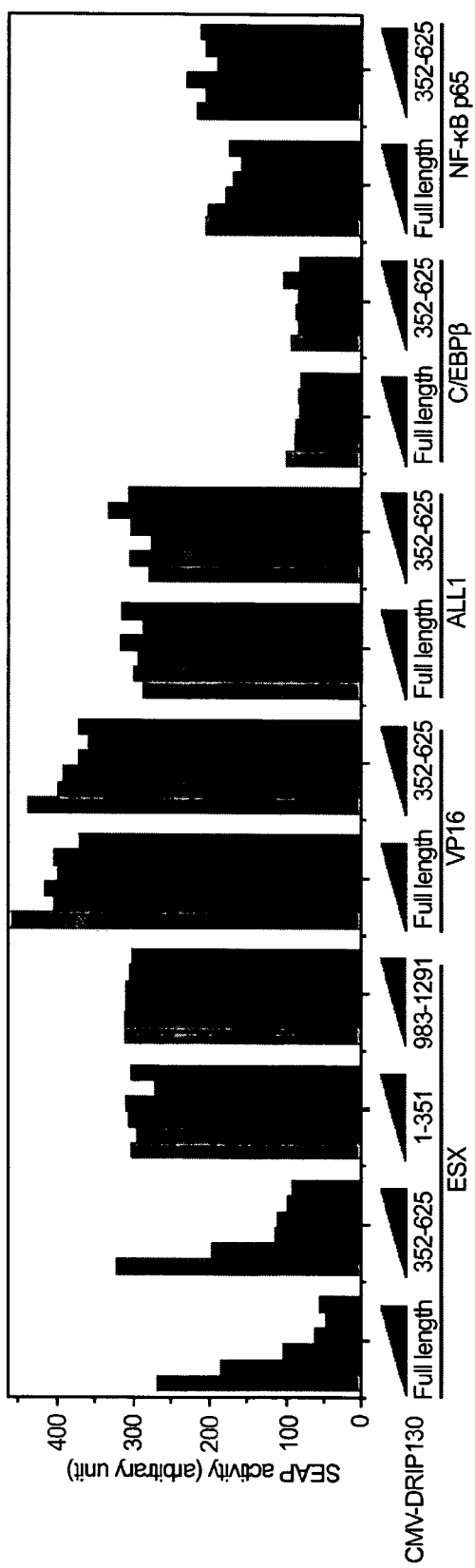
FIG. 3B shows that a series of Sur-2 protein fragments were assayed for the ability to bind the GST fusion of the ESX activation domain (GST-$ESX_{129-159}$). The amino acids 352-625 are sufficient for the interaction with the ESX activation domain.
Figure 3C:
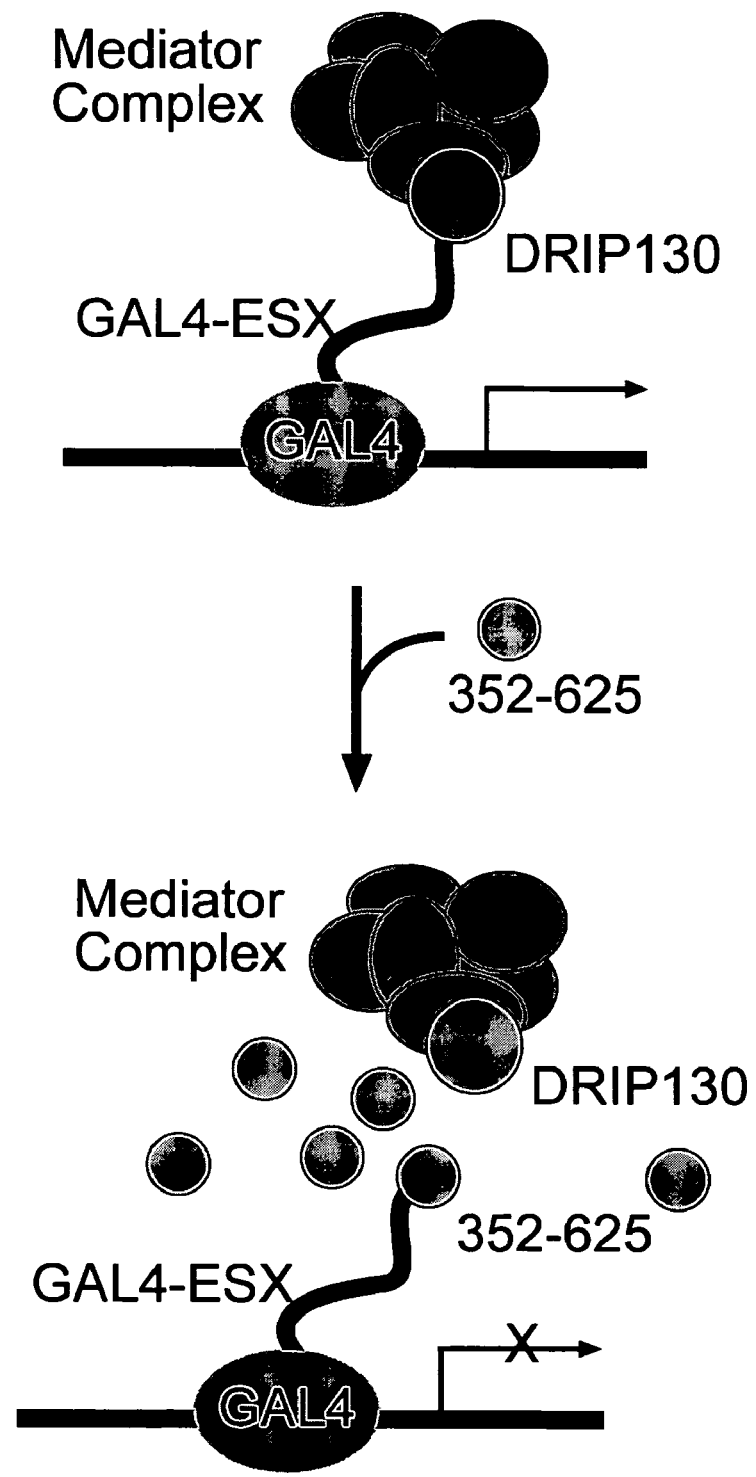
FIG. 3C illustrates a model in which overexpression of the small Sur-2 domain specifically inhibits transcriptional activation by the ESX activation domain.

To map the minimal domain of Sur-2 that binds the ESX activation domain, a series of 35S-labeled deletion mutant proteins of Sur-2 were incubated with the GST fusion of the ESX activation domain, and the bound proteins were analyzed by SDS/PAGE. The Sur-2 fragment of amino acids 352-625 bound most selectively to the ESX activation domain, and its affinity was as high as that of full-length Sur-2 (FIG. 3A). The domain important for the interaction thus lies in the segment that encompasses residues 352-625. Ectopic expression of this 274-aa fragment or full-length Sur-2 impaired the ability of the ESX activation domain to activate transcription in HEK293T cells, presumably by squelching the ESX activation domain from binding to endogenous Sur-2-containing mediator complexes (FIG. 3B). In contrast, overexpression of other Sur-2 fragments that had little affinity to the ESX activation domain, $Sur-2_{1-351}$ and $Sur-2_{983-1291}$, had no detectable impacts on the ability of the ESX activation domain to activate transcription. The inhibitory effect is specific to the ESX activation domain because the forced expression of Sur-2 or its fragment had little effect on the activity of the activation domains of NF-kB p65, ALL1, or C/EBPβ. Sur-2 acts, by means of the Sur-2/CRSP/ARC complex, as an ESX-selective coactivator.

Example 4

Sur-2-Binding Peptide Reduces Her2 Expression in Breast Cancer Cells

Figure 4:
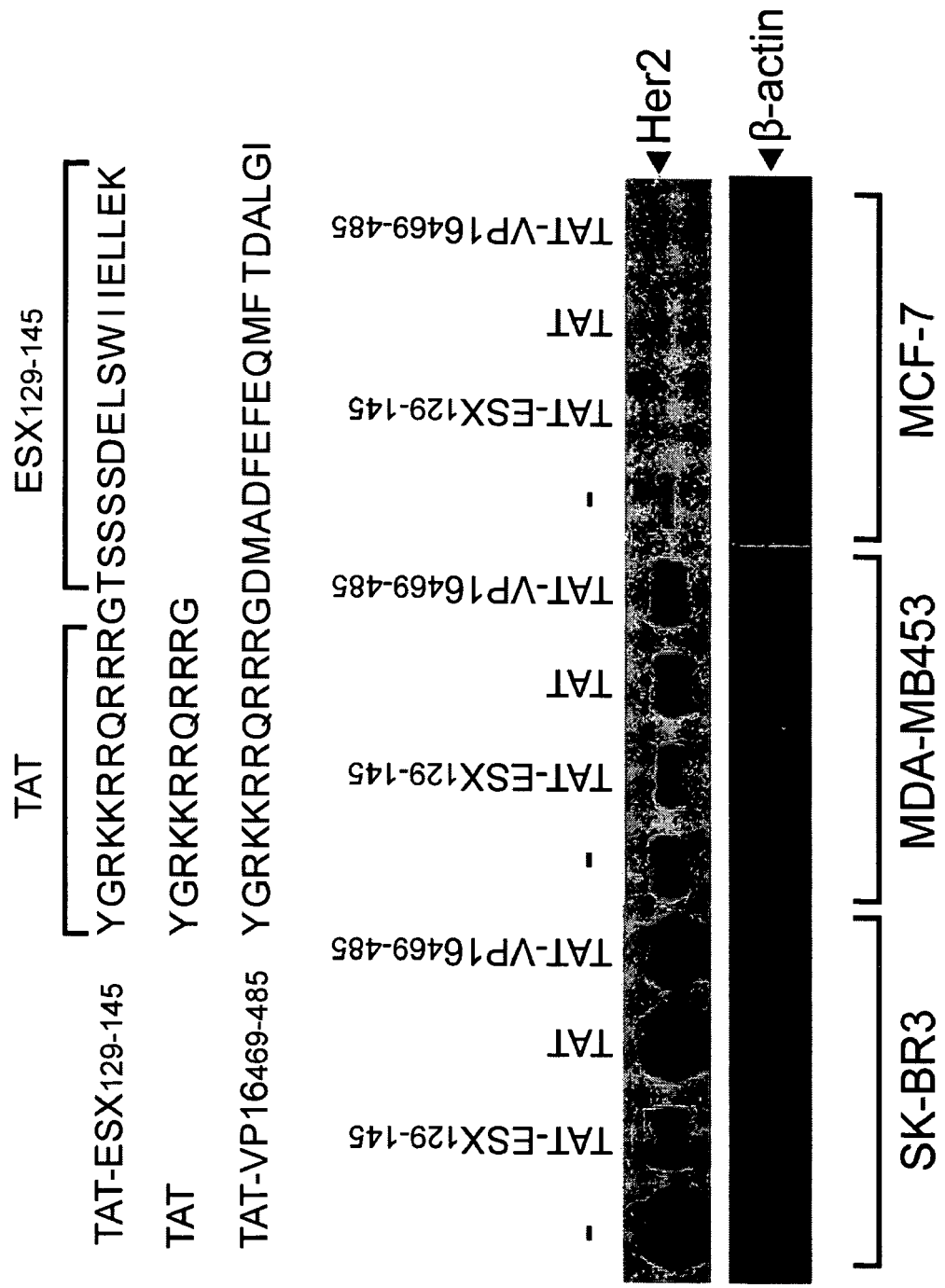
FIG. 4 indicates the effects of TAT-$ESX_{129-145}$ on the protein levels of Her2 in Her2-expressing breast cancer lines. TAT-$ESX_{129-145}$ significantly reduced the amount of Her2 expression in all three breast cancer lines tested.

Sur-2 is a human homolog of *Clostridium elegans* Sur-2, a protein of unknown function whose mutations suppress the phenotype of an activated ras mutation (Singh et al., 1995), and it has been linked to the transcription-activating function of the adenovirus E1A protein and the Elk-1 transcription factor. The functional association of Sur-2 both with the Ras-mediated tumor growth and the Her2 overexpression indicates that the Sur-2-ESX interaction is a target for breast cancer therapy. To test this, we designed a cell-permeable peptide that binds Sur-2 (referred to as TAT-ESX$_{129\text{-}145}$). The design takes advantage of the binding affinity of ESX$_{129\text{-}145}$ and the cell internalization property of the 11-aa peptide derived from the HIV TAT protein. We first examined whether TAT ESX$_{129\text{-}145}$ reduces endogenous expression of the Her2 gene in three Her2-overexpressing breast cancer cell lines, SK-BR-3, MDA-MB-453, and MCF7 (FIG. 4). Cells were incubated in the presence or absence of TAT-ESX$_{129\text{-}145}$, and the protein levels of Her2 were examined by Western blot analyses of normalized amounts of cell lysates. Repeated experiments showed that TAT-ESX$_{129\text{-}145}$ reduced the protein levels of Her2 in all three Her2-overexpressing cell lines we tested, whereas the TAT sequence alone or TAT-VP 16$_{469\text{-}485}$ had no detectable effects. The expression levels of actin were unchanged by TAT-ESX$_{129\text{-}145}$, indicating its selective inhibition of Her2 expression.

Figure 5:
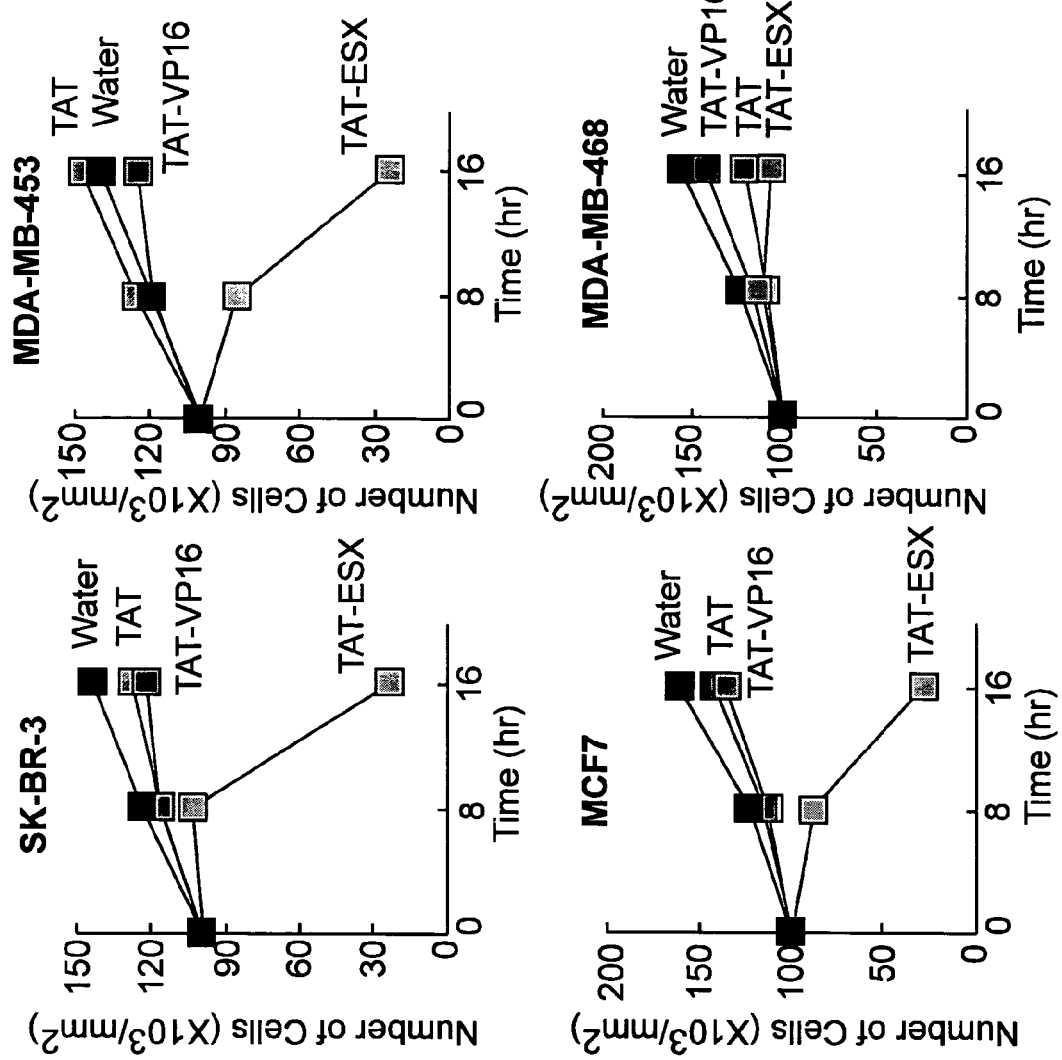
FIG. 5 shows the effects of TAT-$ESX_{129-145}$ on the growth of breast cancer cells.
Figure 5:
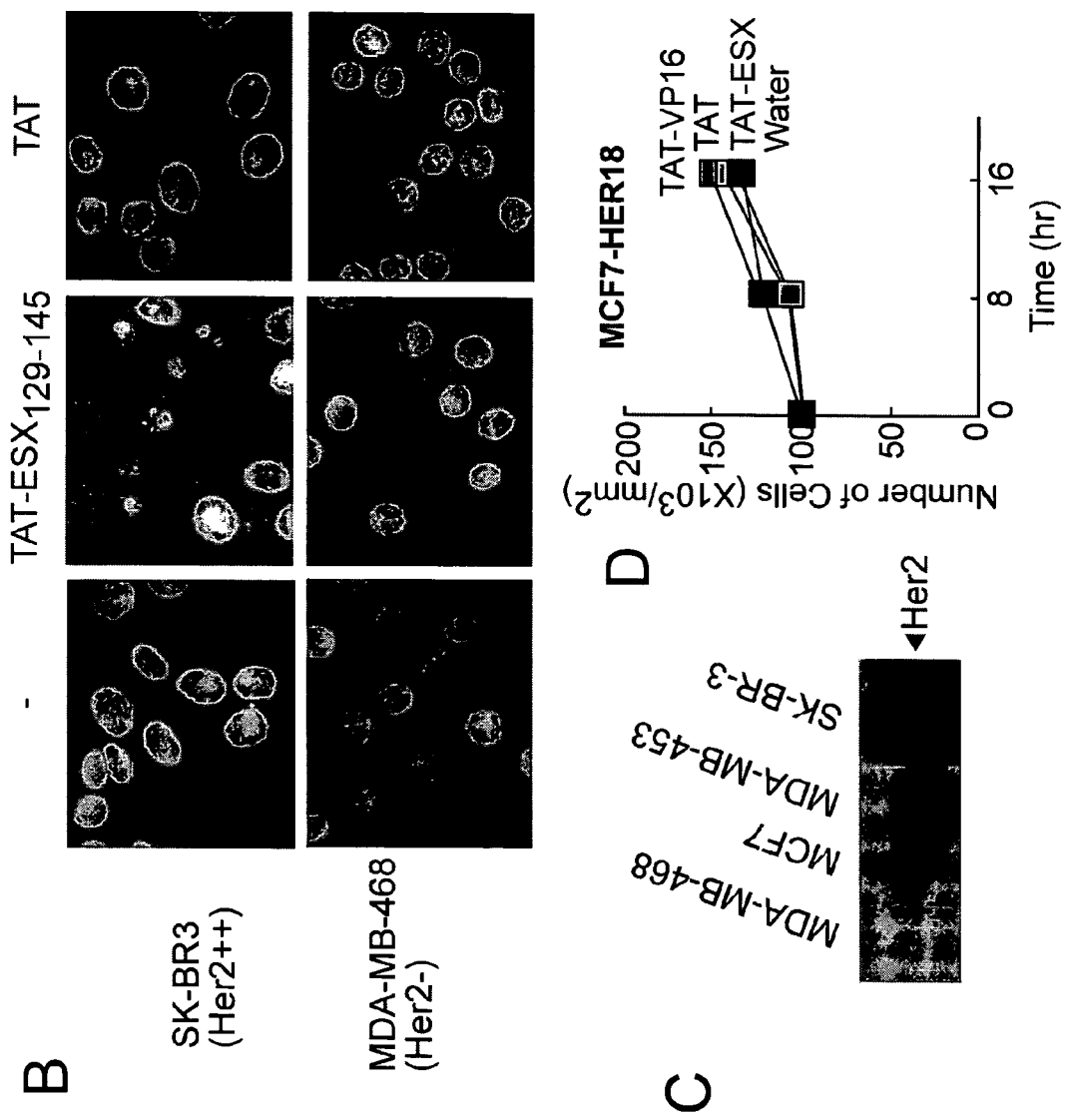

The growth of SK-BR-3, MDA-MB-453, and MCF7 cells was completely blocked in the presence of TAT-ESX$_{129\text{-}145}$, whereas TAT alone and TAT-VP16$_{469\text{-}485}$ had little effects on densation (FIG. 5A). In contrast to the Her2-overexpressing cells, MDA-MB-468, a breast cancer cell line with no detectable levels of Her2, was resistant to TAT-ESX$_{129\text{-}145}$ (FIGS. 5A and 5B). The limited response of MDA-MB-468 to TAT-ESX$_{129\text{-}145}$ demonstrates the specificity of TAT-ESX$_{129\text{-}145}$ in down-regulating the proliferation and viability of Her2-expressing breast cancer cells. The effects of TAT-ESX$_{129\text{-}145}$ on an MCF7 cell line stably transfected with the Her2 gene were examined. The ectopic expression of Her2 on a heterologous promoter effectively rescued MCF7 cells from the TATESX$_{129\text{-}145}$-mediated cell death. These results collectively indicate that disruption of the interaction between ESX and DRIP 130 decreases Her2 expression and causes cell death in Her2-expressing cancer cells.

Example 5

Characterization of the Interaction of ESX with Sur-2

Figure 7A:
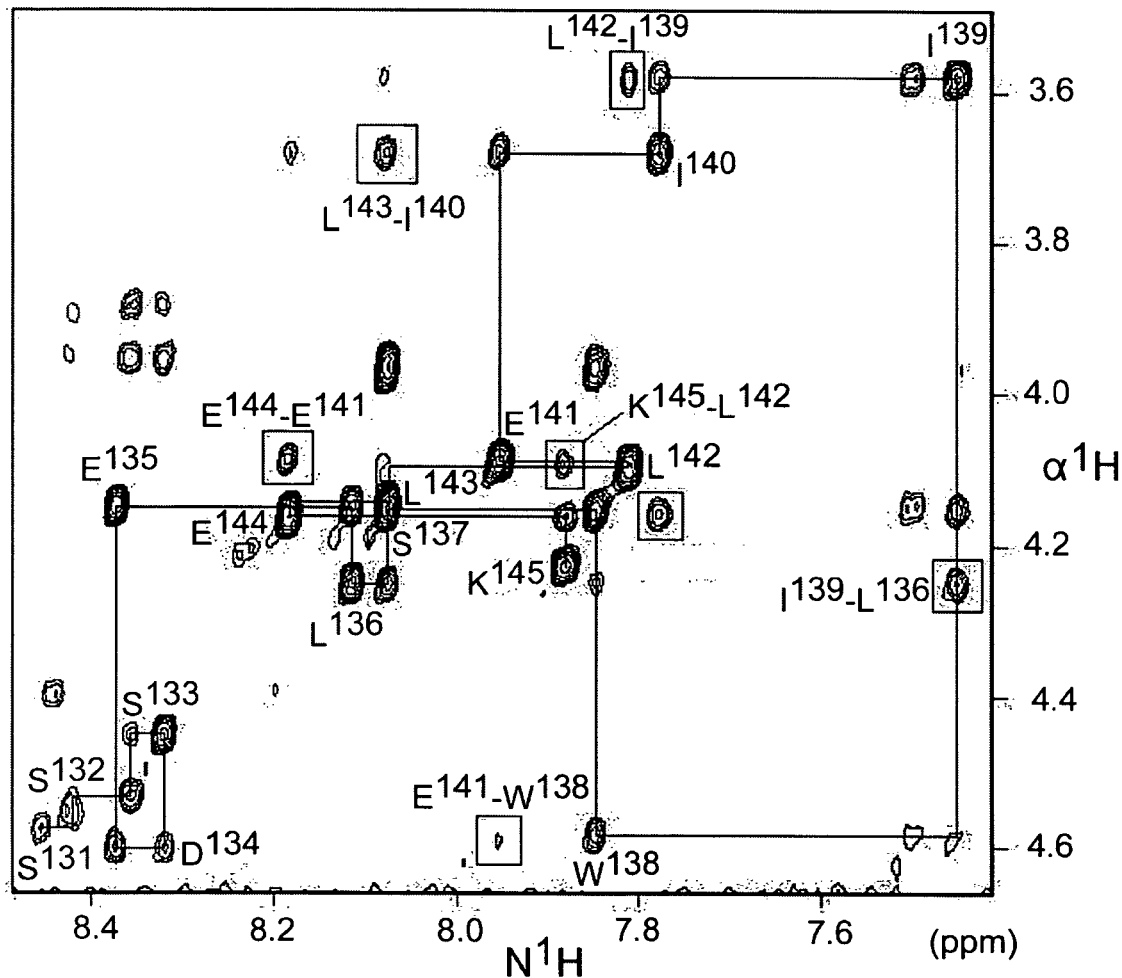
FIG. 7A shows the expansion of the NH-αH region of a NOESY spectrum of $ESX_{129-145}$.
Figure 7B:
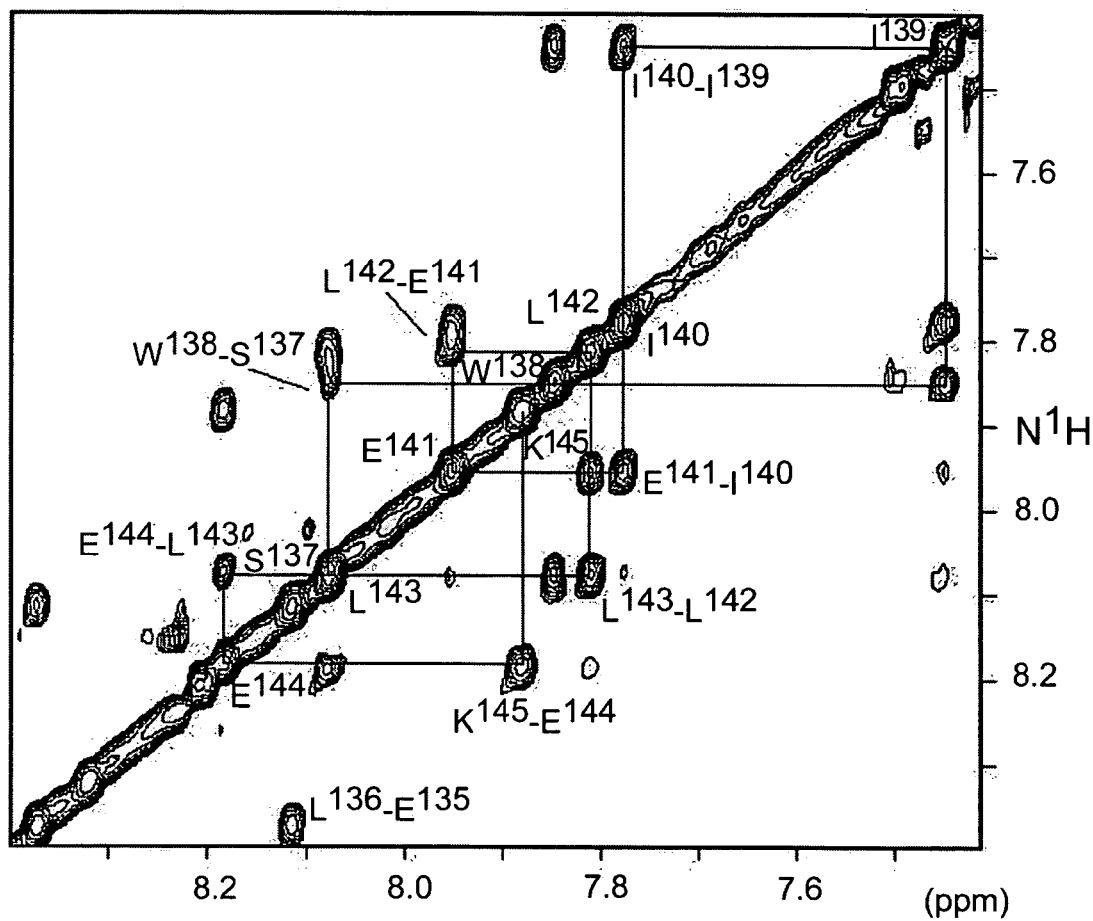
FIG. 7B shows the expansion of the NH—NH region of a NOESY spectrum of $ESX_{129-145}$.
Figure 7C:
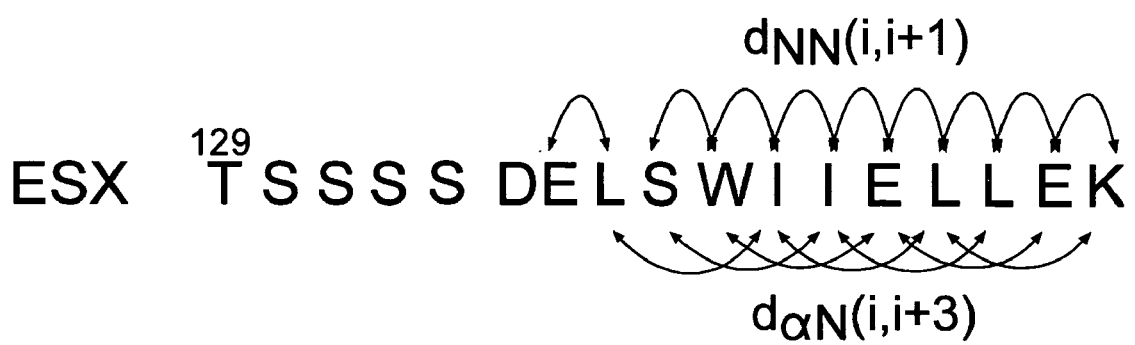
FIG. 7C shows the summary of inter-residue NOE data as characteristic of an α-helical structure.
Figure 8A:
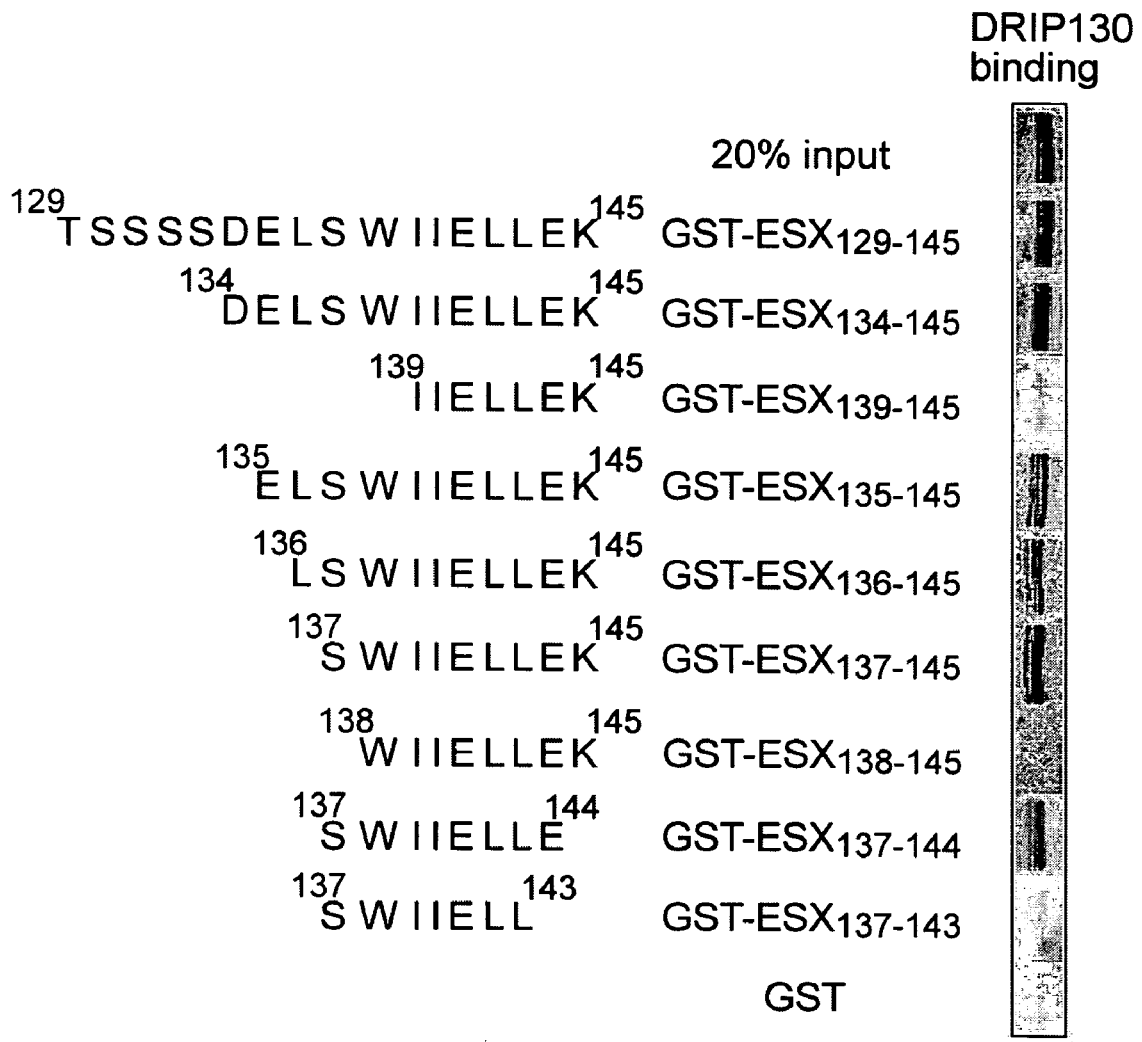
FIG. 8A identifies the minimal ESX peptide that binds Sur-2 in vitro.
Figure 8C:
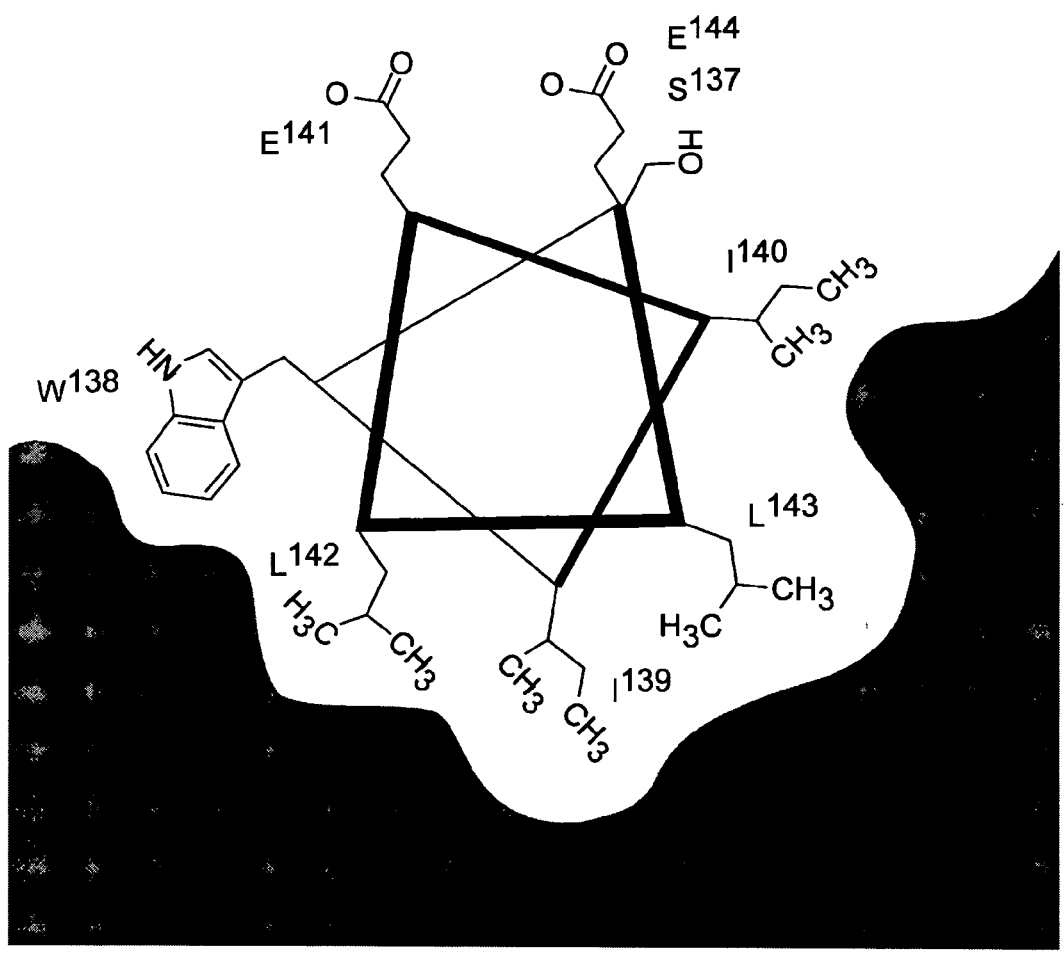
FIG. 8C shows the projection of the minimal binding peptide, $ESX_{137-144}$, onto a helical wheel.

ESX$_{129\text{-}145}$ exhibited a substantial number of interresidue nuclear Overhauser effects (NOEs) including those between successive amide protons in the main chain and those arising from d$_{aN}$(i, i 1 3) (FIGS. 7A and 7B). The pattern of the NOE connectivities is characteristic of the pattern observed for α-helical secondary structures, especially in the region from Ser-137 to Lys-145 (FIG. 7A). Thus, the residues from Ser-137 to Lys-145 have strong helical propensity. Deletion and point mutant proteins of ESX$_{129\text{-}145}$ were constructed and examined for their ability to bind Sur-2 in vitro (FIG. 8A). The results of the deletion mutants indicate that the residues from Ser-137 to Glu-144 are necessary for the interaction with Sur-2; this 8-aa segment corresponds almost precisely to the region that was detected to be helical by NMR. Substitutions of bulky hydrophobic residues in the short peptide abolished the interaction with Sur-2, whereas mutations of the hydrophilic residues had no detectable effects (FIG. 8B). The projection of residues Ser-137 to Glu-144 onto a helical wheel reveals that these hydrophobic residues all lie along one face of the short helix, perhaps making direct contact with the chemically complementary surface in Sur-2 (FIG. 8C).

Example 6

Identification of Adamanolol Sur-2 Inhibition Activity

Adamanolol was identified from a chemical library of 2,422 druglike compounds purchased from Tripos Inc. (St. Louis, Mo.) that contain either indole, benzimidazole, or benzodiazepin in their structures. These library members were carefully selected from the entire compound collection of Tripos, Inc. In addition to the presence of indole-like structures, they have molecular weights suited for inhibitors of protein-protein interactions but carry less than six nitrogen atoms, and their clogP values are between −1 and 6.

Figure 9:
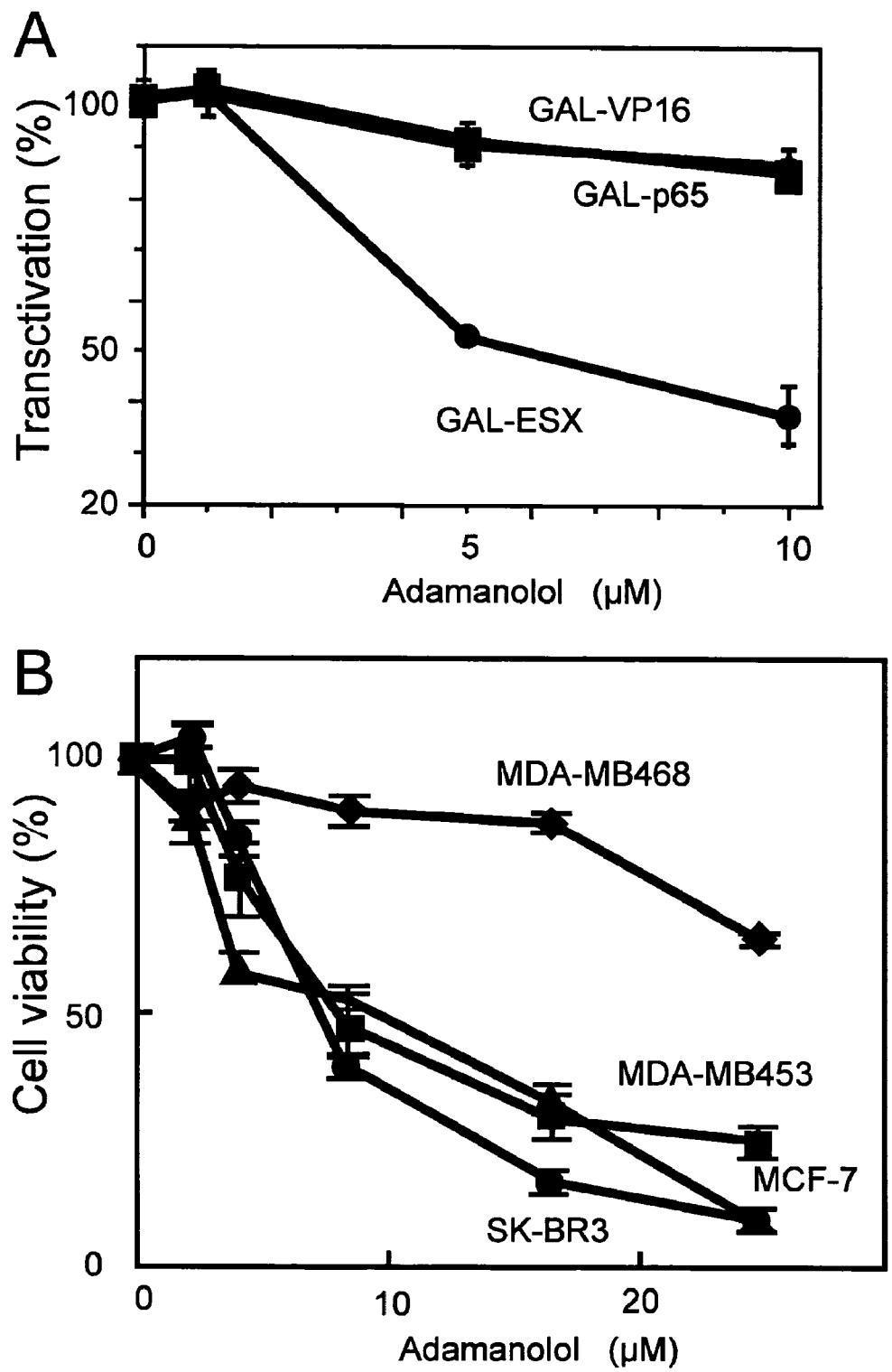
FIG. 9 shows the activity of adamanolol (7QH2).
Figure 9:
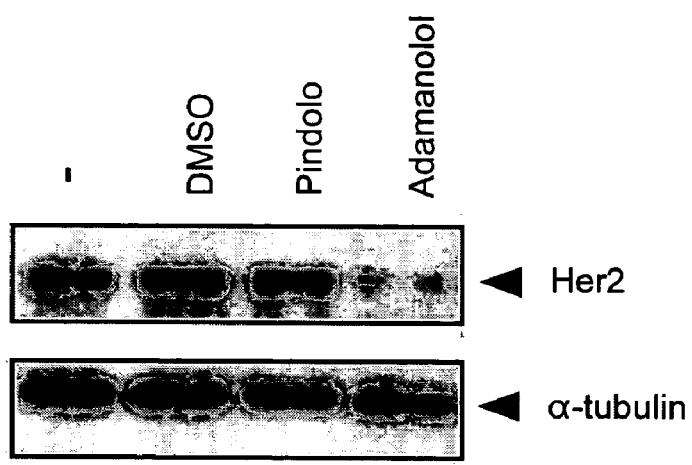
Figure 9:
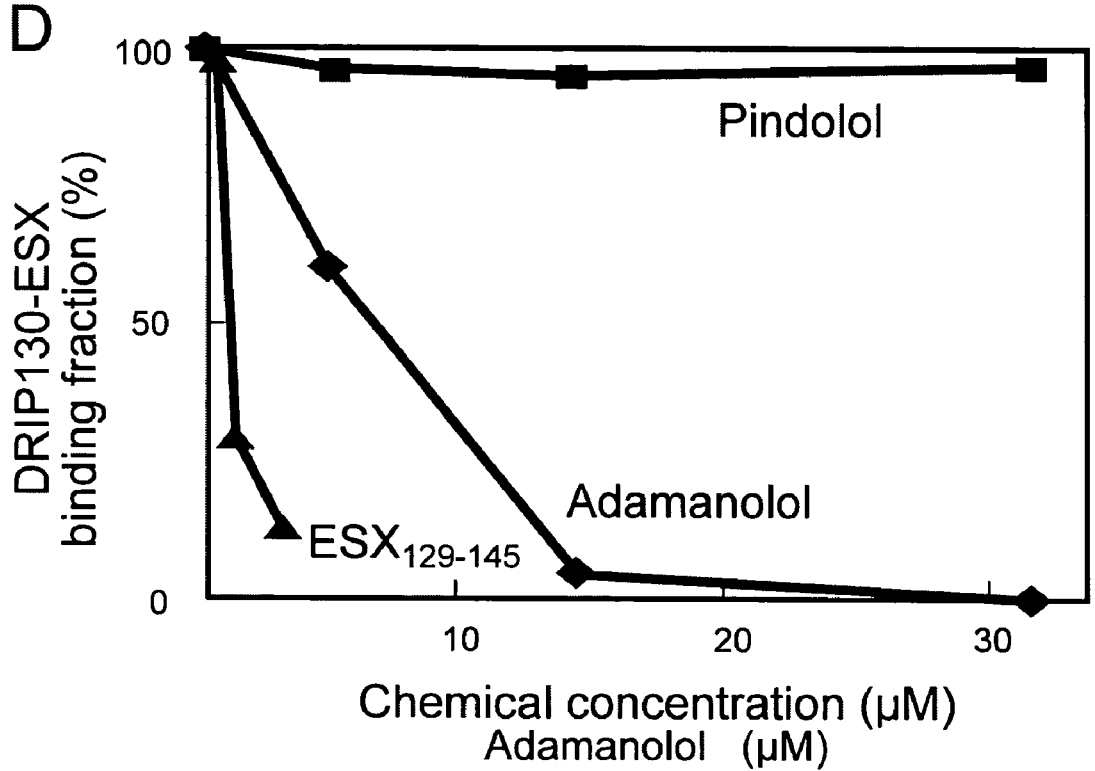
Figure 10:
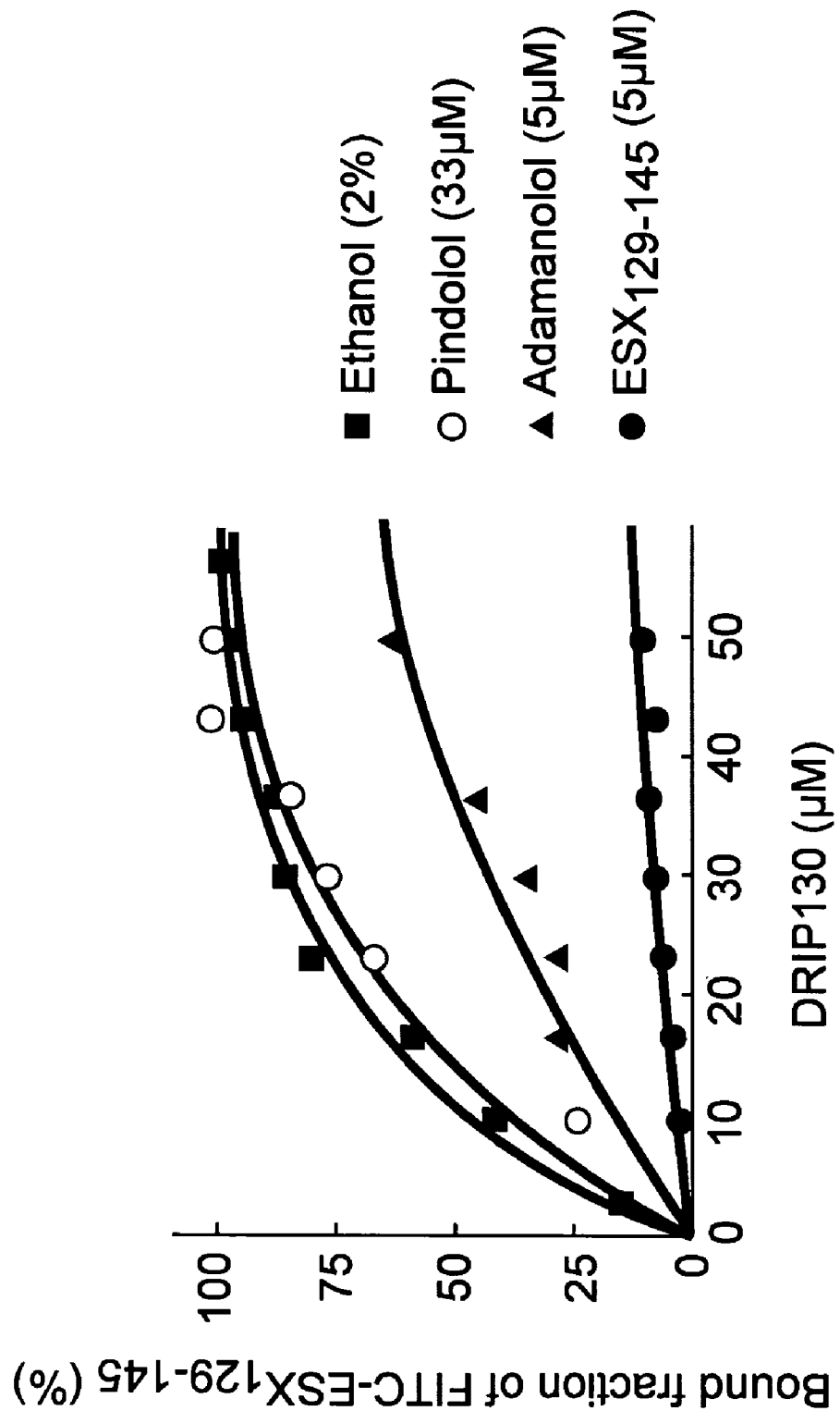
FIG. 10 shows the estimation of the dissociation constant of the Sur-2 and ESX interaction.

The 2,422 compounds were individually assayed at multiple concentrations for their ability to impair the viability of Her2-overexpressing SK-BR3 cells and Her2-negative MDAMB468 cells. The compounds that selectively impaired the viability and cell growth of SK-BR3 cells were selected and then assayed by transcription reporter gene assay. The compounds that inhibited the ability of the ESX activation domain, but not the VP16 activation domain, to activate the reporter gene expression were selected. Among the selected compounds was adamanolol. (FIG. 9B). The drug-like pindolol derivative impaired the ability of the ESX activation domain to stimulate transcription in cells, whereas it had little effects on that of the VP16 activation domain, a prototypical activator (FIG. 9A). Adamanolol impaired the viability of Her2-positive breast cancer cell lines (SK-BR3, MDA-MB453, and MCF-7), but had much milder effects on MDA-MB468 with no detectable levels of Her2 (FIG. 9B). Western blot analyses of drug-treated cells showed that the expression of Her2 protein, but not that of α-tubulin, was significantly reduced by adamanolol in the Her2-positive SK-BR3 cells.

Example 7

Transcription Reporter Gene Assay

Mammalian expression vectors each encoding the activation domain of ESX, VP16, or NFκBp65 fused with the GAL4 DNA-binding domain were used. Each expression construct was co-transfected to HEK293Tag human kidney cells together with a reporter plasmid in which the production of secreted alkaline phosphatase (SEAP) is under control of an IL-2 promoter carrying five GAL4 binding sites. After a 24 hour incubation in the presence or absence of adamanolol, an aliquot of the culture was assayed for SEAP activity. The total amounts of transfected DNA were normalized.

Example 8

Cell Viability Assay

The breast cancer cells were plated on 96-well plates at the density of 5×10$_3$ cells/well and maintained for 24 hrs. Adamanolol was added to the medium at varied concentrations and incubated for another 24 hrs. Premix WST-1 solution (Takara) was added to each well and incubated for 2 hrs. Cell viability was estimated by measuring absorbance at 450 nm with a SPECTRAmax microplate reader.

Example 9

Effects of Adamanolol on the Expression Levels of Her2 in SK-BR3 Cells

Her2-overexpressing SK-BR3 cells were treated by 7.3 μM of adamanolol for 24 hrs, and whole cell lysates were analyzed by western blots. The primary antibody used for the western analysis were a monoclonal antibody against Her2 (c-neu-Ab-3; Oncogene Science) and a monoclonal antibody against (-tubulin (T5168; Sigma). The blotted membranes were then incubated with horseradish peroxidase-conjugated sheep anti-mouse immunoglobulin and visualized with ECL chemiluminescence detection reagents (Amersham Bioscience).

Example 10

Fluorescence Perturbation Study

To monitor the ESX-DRIP130 interaction, we labeled $ESX_{129-145}$ with fluorescein isothiocyanate (FITC; Pierce) at the $Lys_{144}$ position and measured its fluorescence spectra upon adding the glutatathione-S'-transferase (GST) fusion of $DRIP130_{352-625}$. $ESX_{129-145}$ was synthesized by standard Fmoc chemistry (the $NH_2$ terminus was capped by an acetyl group during the synthesis) and purified by HPLC. The peptide was then coupled with FITC at the $Lys_{144}$ position in a conjugation buffer (100 mM carbonate-bicarbonate buffer, pH 9) in dark and purified by NAP-5 desalting column (Amersham). The labeled peptide was quantified by UV and visible absorbance.

GST-Sur-$2_{352-625}$ was expressed and purified. Varied concentrations of the fusion protein were added to FITC-$ESX_{129-145}$ (10 nM) in phosphate buffered saline containing 2% (v/v) ethanol, and the fluorescence spectra of FITC-$ESX_{129-145}$ were measured by an ABI LS-50B Fluorescence Spectrometer (Ex: 490 nm). The dissociation constant of the interaction was estimated to be 12 µM through the emission perturbation at 522 nm.

To examine the effects of adamanolol on the interaction in vitro, the ethanol component of the binding buffer was replaced with an ethanolic solution of adamanolol. The fractions of FITC-$ESX_{129-145}$ (10 nM) bound to 50 µM of GST-Sur-$2_{352-625}$ were estimated by measuring fluorescence emission at 522 nm. ESX129-145 and pindolol were used as positive and negative controls, respectively.

Example 11

NMR Studies of Adamanolol

Figure 6:
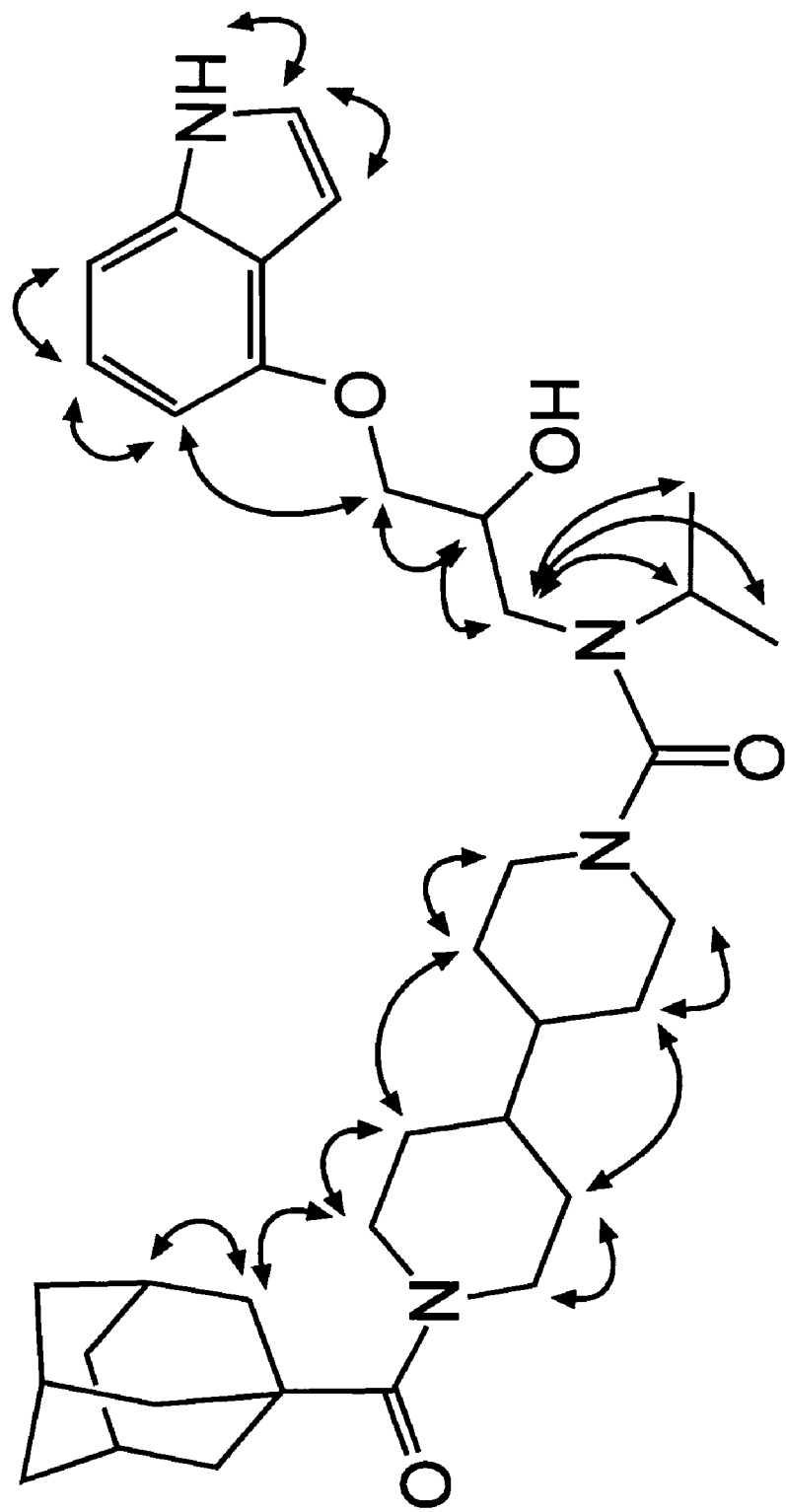
FIG. 6 shows NMR data for adamanolol.

Adamanolol (0.5 mg) was dissolved in 99.8% chloroform-d containing 0.05% (v/v) TMS, and NMR data of the sample were collected by a Bruker AMX600 spectrometer. The assignment of the proton signals was obtained by using a combination of TOCSY, DQF-COSY, and NOESY data sets. In the NOESY spectra, 512 free induction decays were recorded at 298 K with mixing times of 300 and 500 ms. The data were analyzed by the Felix98.0 software (Biosym Technologies) with appropriate apodization and zero-filling to yield real 2D 2K X 2K matrices after reduction. NMR analyses of adamanolol showed signal broadening of the protons around the urea linker at a room temperature and the absence of NOEs between the isopropyl protons and the piperidine even with a 500 msec NOESY mixing time.[7] A reasonable explanation for these NMR characters is a rigid conformation around the urea linker with the preference for the Z conformer imposed by the bulky isopropyl group. See FIG. 6.

Example 12

Figure 13:
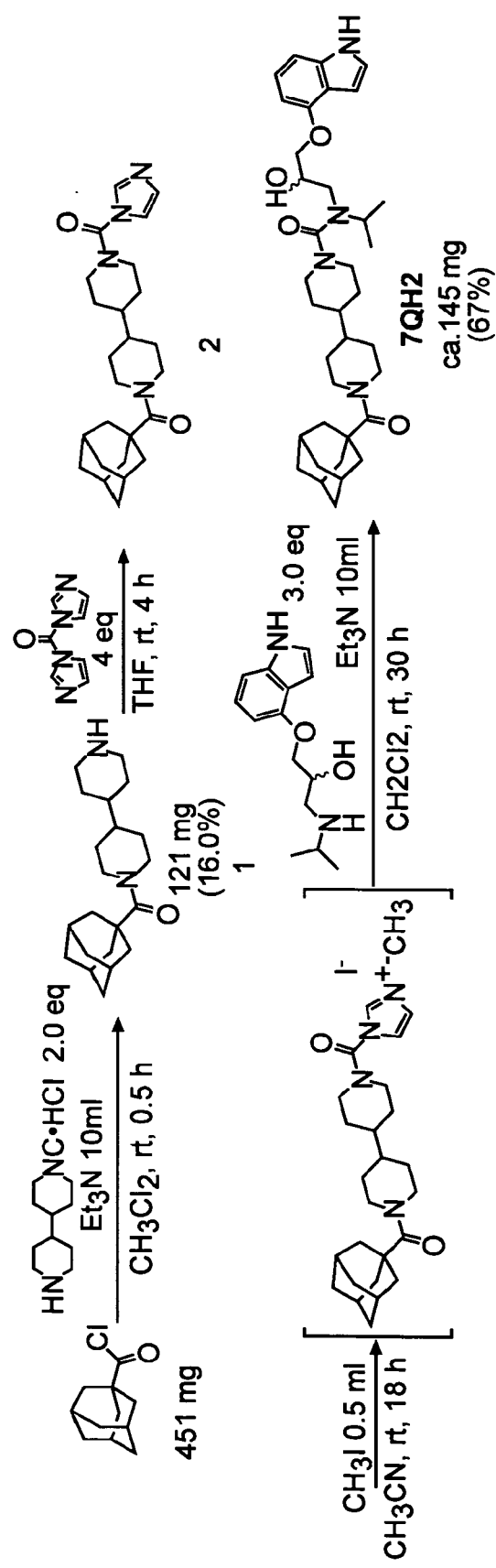
FIG. 13 shows the synthetic protocol for adamanolol and N-tosyl adamanolol.
Figure 14:
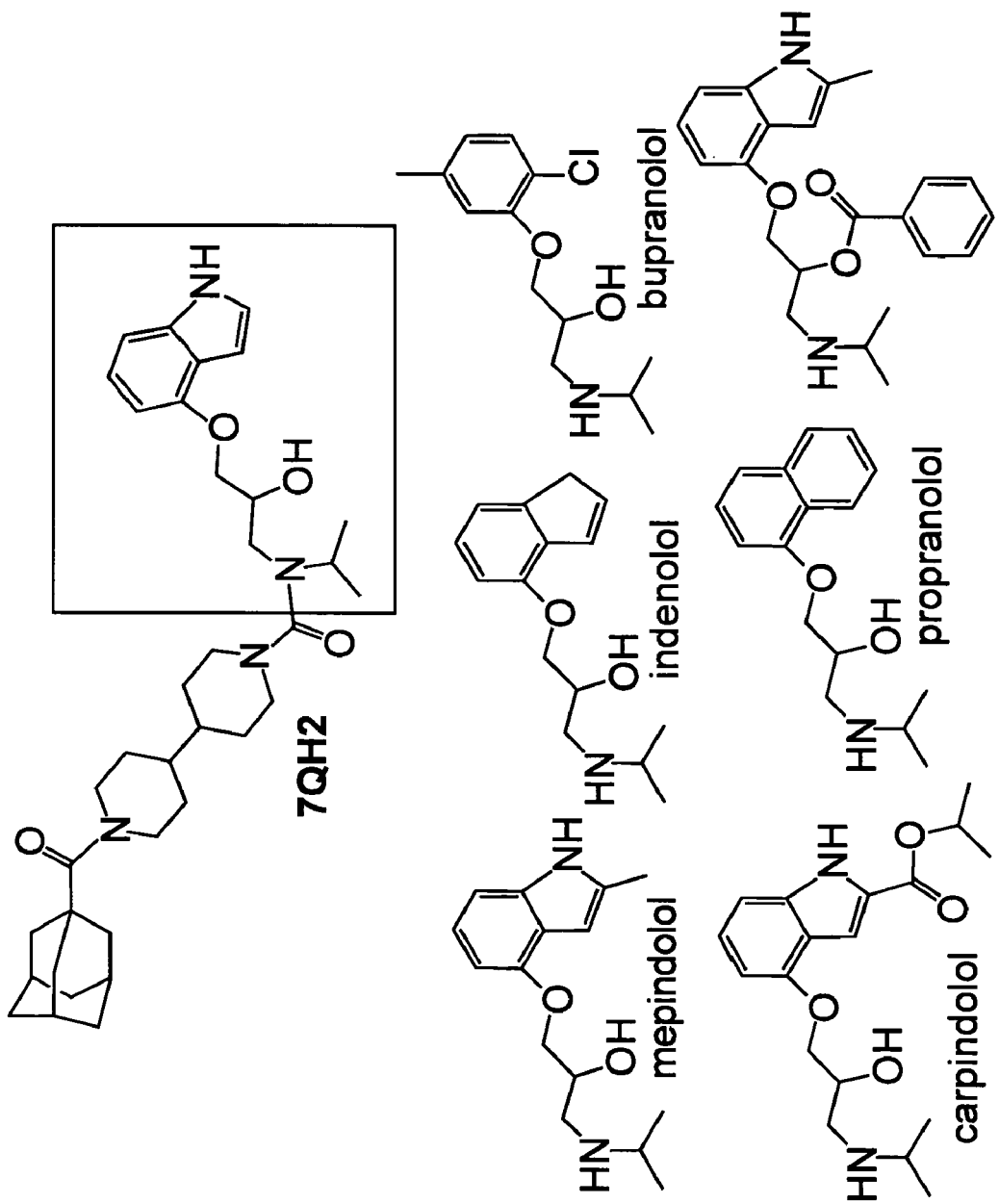
FIG. 14 shows chemical structures of representative pindolol analogs.
Figure 15:
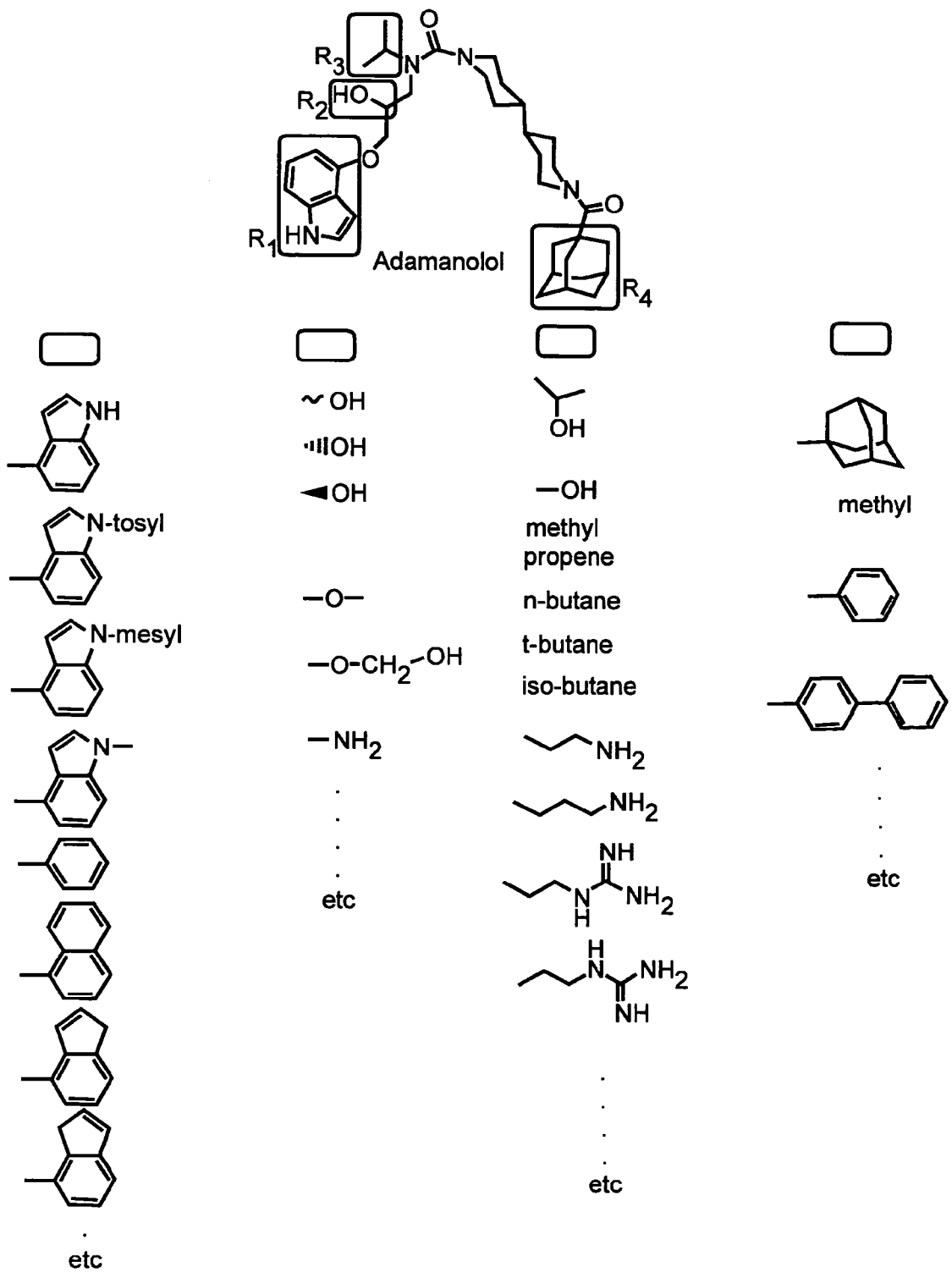
FIG. 15 is a representation of side groups substituents in adamanolol.
Figure 16A:
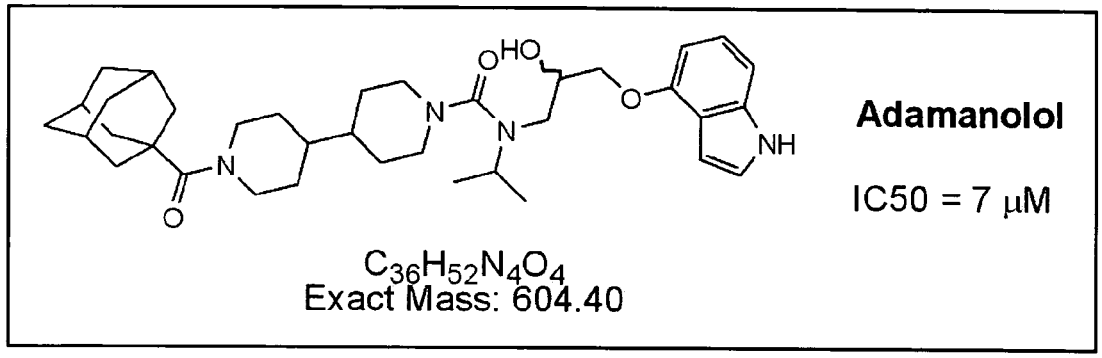
FIG. 16 indicates synthesized functionalized adamanolol derivatives, and their activity (expressed as the $IC_{50}$) after in vitro testing in Her2-expressing breast cancer cell lines. Five compounds are as active as adamanolol, while 2 are more active, and three are about half as active.
Figure 16A:
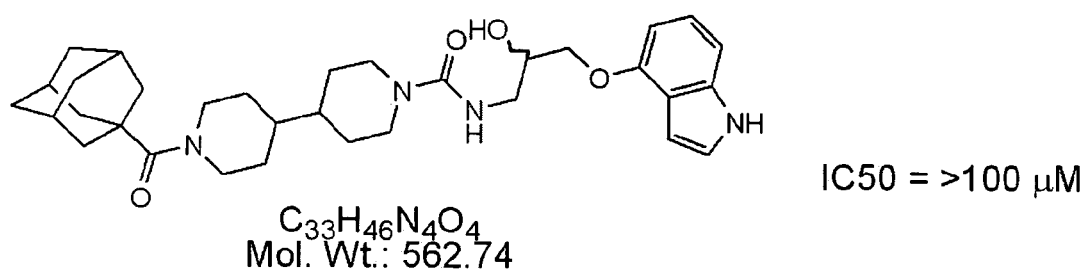
Figure 16A:
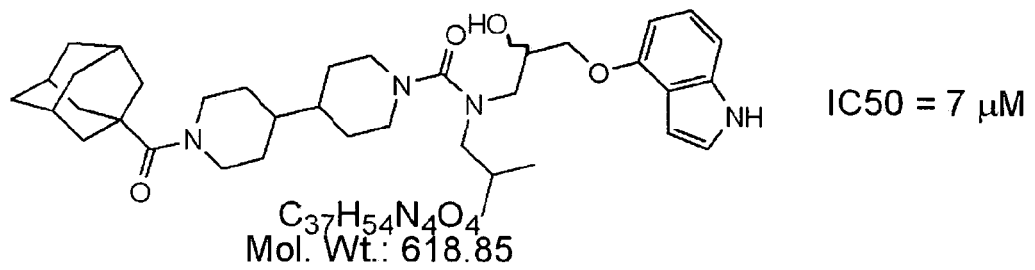
Figure 16A:
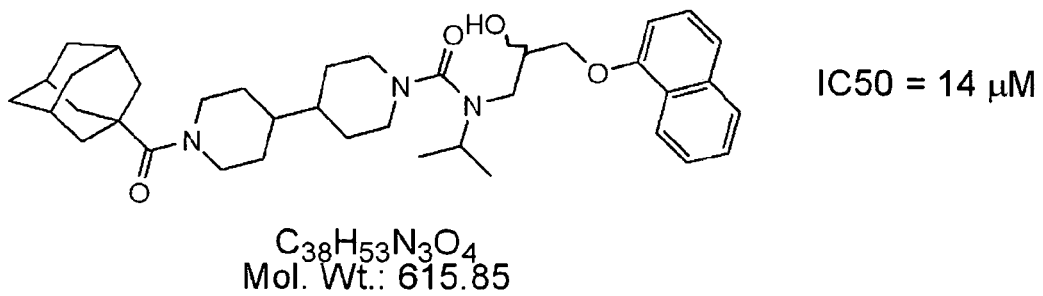
Figure 16B:
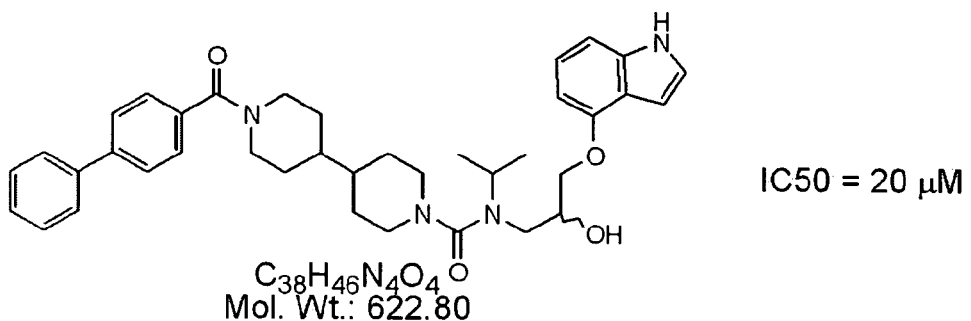
Figure 16B:
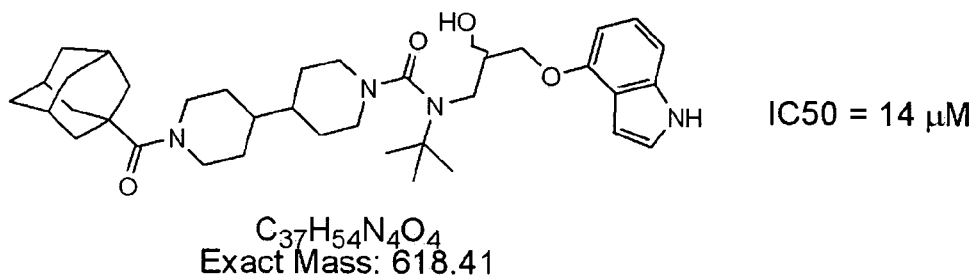
Figure 16B:
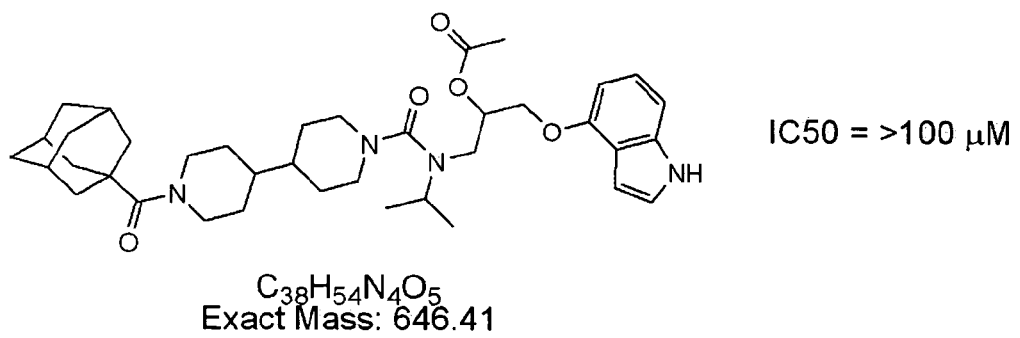
Figure 16B:
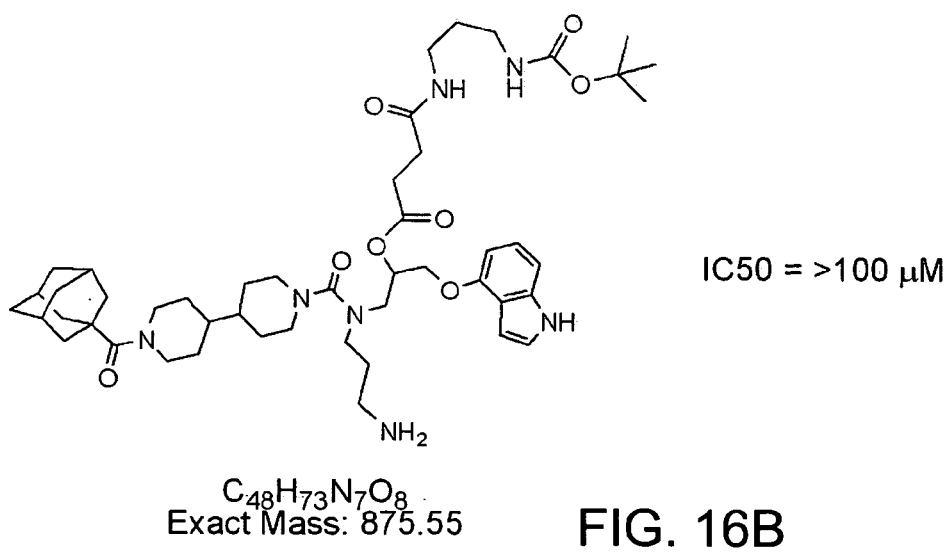
Figure 16C:
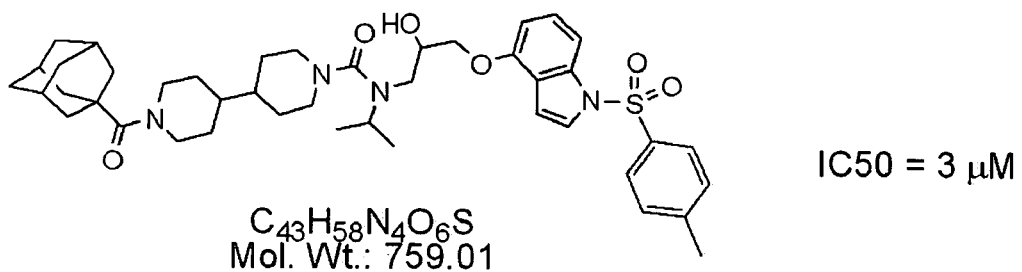
Figure 16C:
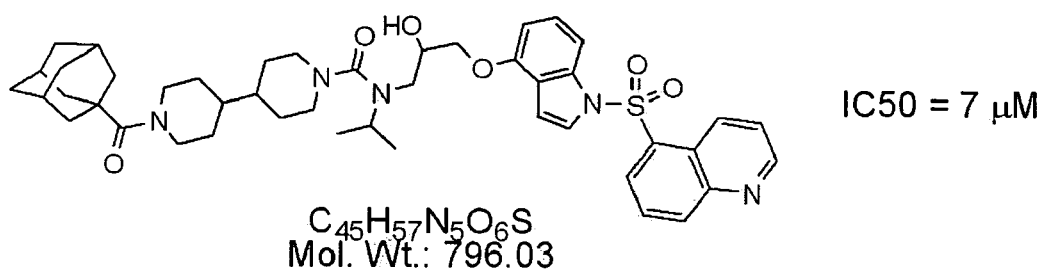
Figure 16C:
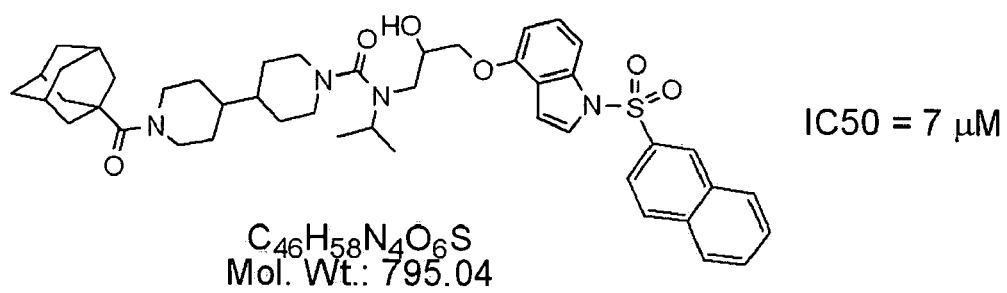
Figure 16C:
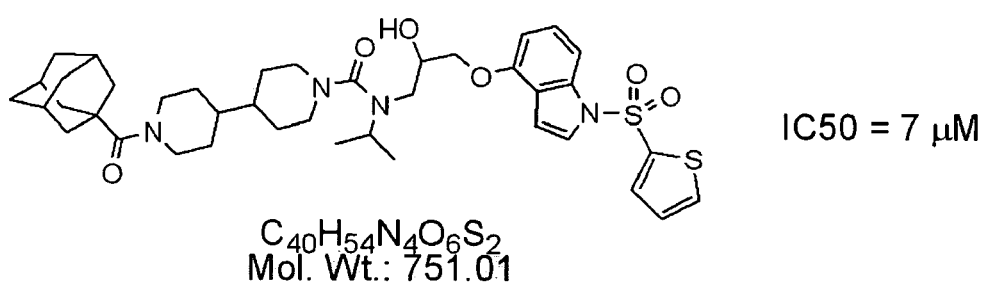
Figure 16D:
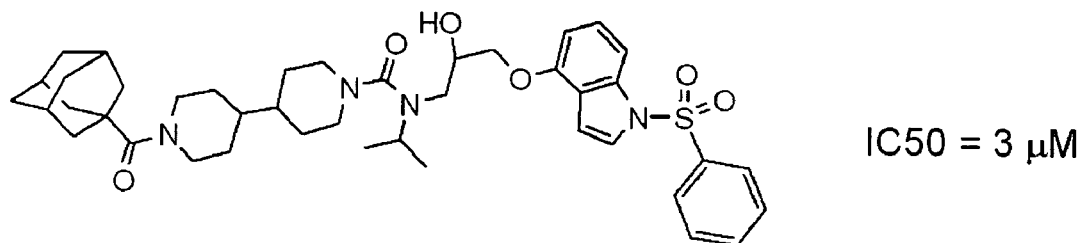
Figure 16D:
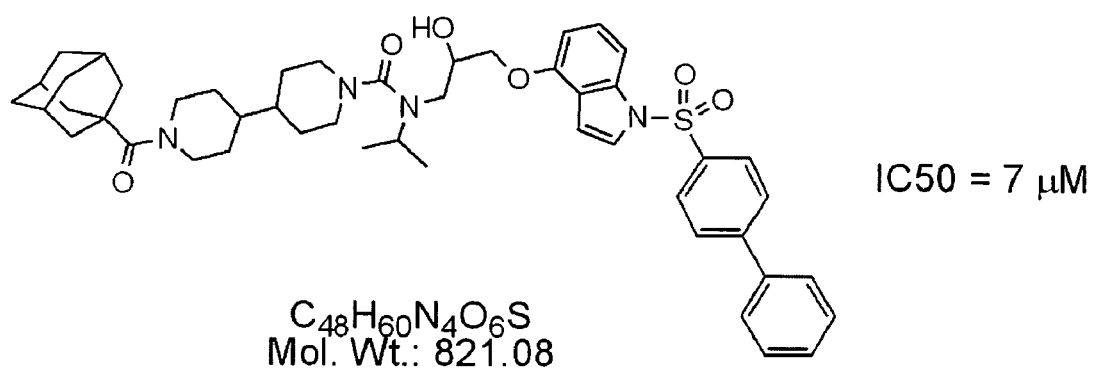
Figure 16D:
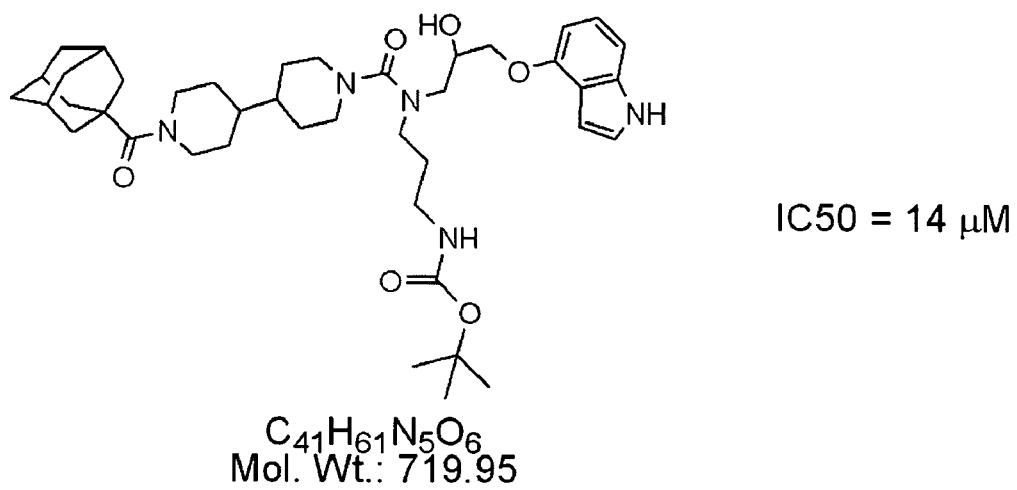

Synthetic Scheme for the Preparation of Adamanolol and Functionalized Adamanolol Derivatives The solvents used in reactions were dried prior to use. All other reagents were used as received without purification. All moisture-sensitive reactions were performed in flame-dried and/or oven-dried glassware under a positive pressure of nitrogen unless otherwise noted. Thin-layer chromatography was carried out with glass TLC plates precoated with silica gel 60 F254. Flash column chromatography was accomplished with silica gel BW820MH. Proton nuclear magnetic resonance spectra were recorded in deuterated solvents at 270 or 600 MHz. To a solution of 4-hydroxy indole (FIG. 13, compound 1) (0.50 g, 3.8 mmol) in dimethylsulfoxide (10 mL) at 45° C. was added potassium hydroxide (0.4 g, 7.6 mmol) followed by epichlorohydrin (1.4 g, 15.2 mmol). The reaction mixture was stirred at 45° C. for 4 h. The reaction was quenched with a saturated solution of $NH_4Cl$, extracted with diethyl ether (3×50 mL). The combined organics were dried with $MgSO_4$, and concentrated. The product was purified by elution from silica gel column with benzene/acetone mixtures to give the glycidyl 4-indolyl ether (FIG. 13, compound 2) (0.75 g, 3.8 mmol, 99%) as a clear oil. To a solution of glycidyl 4-indolyl ether (FIG. 13, compound 2) (215 mg, 1.14 mmol) in methanol (2 mL) was added isobutyl amine (160 mg, 2.28 mmol). The solution was heated to 100° C. and stirred for 32 h. The product was purified by elution from silica gel column with benzene/acetone mixtures to give the corresponding amine (FIG. 13, compound 3) (120 mg, 0.46 mmol, 40%) as a clear oil. To a solution of 4,4'-bipiperidine (420 mg, 5.0 mmol) and triethylamine (2 mL) in 150 mL of $CHCl_3$ was added a solution of 1-adamantanecarbonyl chloride (FIG. 13, compound 4) (500 mg, 2.5 mmol) in 50 mL of $CHCl_3$. The resulting mixture was refluxed for 0.5 h, diluted with brine, and dried over $MgSO_4$. The solution was then concentrated in vacuum and purified by elution from silica gel column with $CHCl_3$/methanol mixtures to give the corresponding amide (5) (750 mg, 2.3 mmol, 90%) as a clear oil. See FIG. 13.

Example 13

Synthesis of Adamanolol and its Isobutyl Derivative

Figure 11:
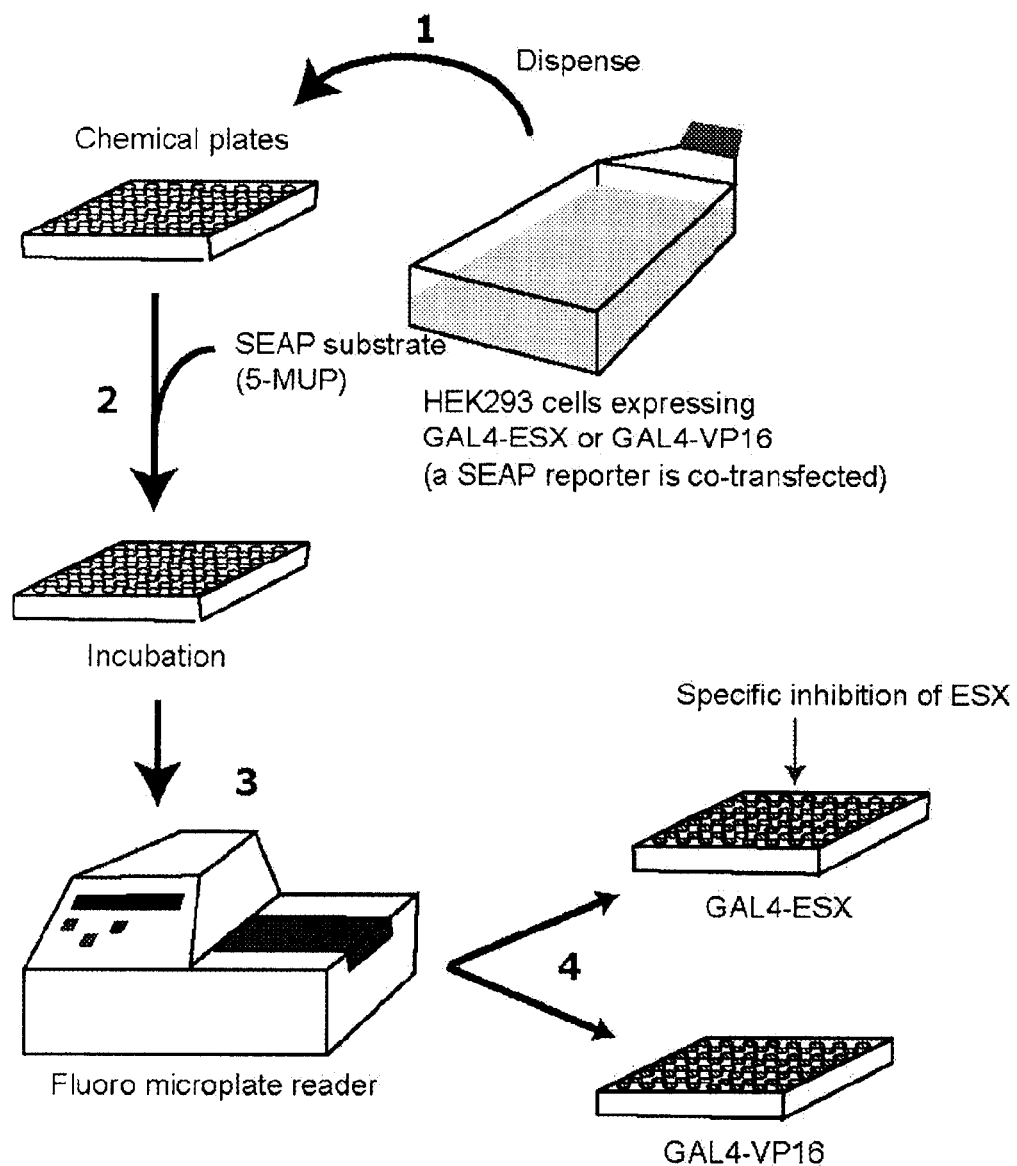
FIG. 11 shows a screening technique to identify compounds assayed for the ability to inhibit the activity of GAL4-ESX.
Figure 12:
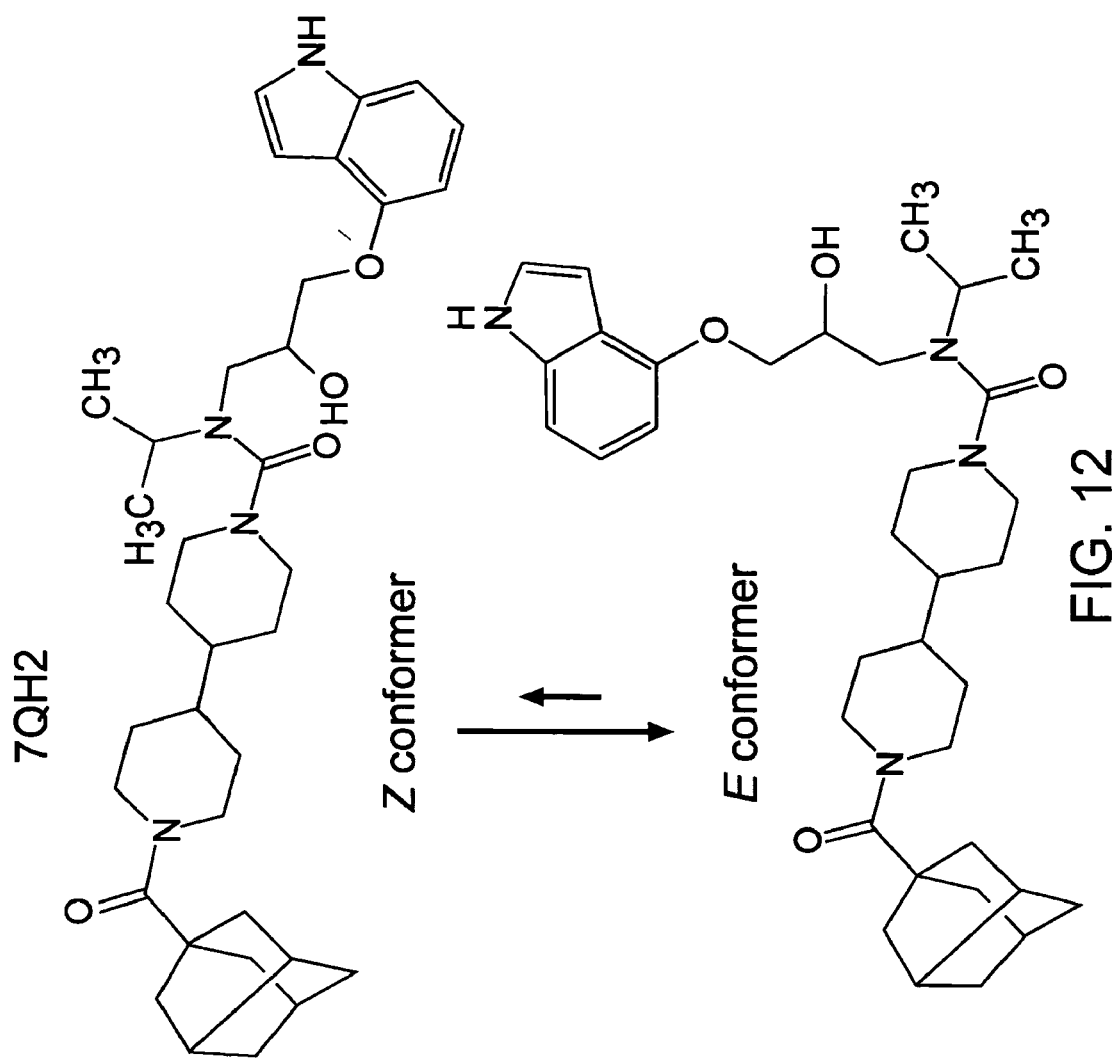
FIG. 12 shows stereoisomers of adamanolol. Adamanolol has two conformers (E and Z) due to the limited rotation of the urea group.

To a solution of amide (120 mg, 0.36 mmol) in 10 mL of THF was added a solution of 1,1'-carbonyldiimidazole (236 mg, 1.44 mmol) in THF (5 mL). The resulting mixture was refluxed for 4 h. To the reaction mixture was added diethyl ether (20 mL) and washed with brine (3×20 mL). The organic layer was dried with $MgSO_4$ and concentrated. The carbamoyl imidazole did not require further purification for use in the subsequent steps. Stirring of carbamoyl imidazole with MeI (0.5 mL) in MeCN (2 mL) for 18 h at room temperature. Evaporation of the solvent and excess MeI in vacuum gave the corresponding imidazolium salt quantitatively and again required no additional purification for its conversion to adamanolol. To a solution of imidazolium salt in 2 mL of $CH_2Cl_2$ was added a solution of pindolol (268 mg, 1.08 mmol) or N-[3-(4-indolyloxy)-2-hydroxypropyl]-isobutyl amine (283 mg, 1.08 mmol) in $CH_2Cl_2$ (1 mL) and $Et_3N$ (0.5 mL). The resulting mixture was stirred at room temperature for 30 h. Evaporation of the solvent and purified by elution from silica gel column with $CHCl_3$/methanol mixtures to gave adamanolol (145 mg, 0.24 mmol, 67%) or its isobutyl derivative (42 mg, 0.07 mmol, 19%) as a clear oil. Adamanolol: $^1H$ NMR ($CDCl_3$, 270 MHz) $\delta_H$ 7.10 (br, 1H), 7.08-7.04 (m, 2H), 6.58 (d, 1H), 6.51 (d, 1H), 5.33 (br, 1H), 4.52 (br, 2H), 4.39 (m, 1H), 4.37(br, 1H), 4.15 (br, 2H), 3.69 (d, 1H), 3.43 (m, 1H), 3.30 (br, 1H), 2.65 (br, 4H), 2.02 (s, 3H), 1.98 (s, 6H), 1.71 (s, 6H), 1.34 (dd, 6H), 1.45-0.86 (m, 10H); MS (FAB) ($M+H^+$) 605. See FIG. 11.

Example 14

Preparation of N-tosyl Adamanolol

To a solution of adamanolol, (30.1 mg, 0.05 mmol) in 1 mL of THF was cooled to 0° C., followed by the addition of 60% sodium hydride in mineral oil (12 mg, 0.50 mmol) and tosyl chloride (10.4 mg, 0.05 mmol). After being stirred at this temperature for 0.5 h, the reaction mixture was allowed to warm to room temperature and stirred for 2 h. The reaction was quenched with brine, extracted with $CH_2Cl_2$ (3×20 mL). The combined organics were dried with $MgSO_4$ and concentrated. The product was purified by elution from silica gel column with $CHCl_3$/methanol mixtures to give the N-tosyl adamanolol (21.5 mg, 0.03 mmol, 57%) as a clear oil. See FIG. 11.

Example 15

Animal Studies

Figure 17:
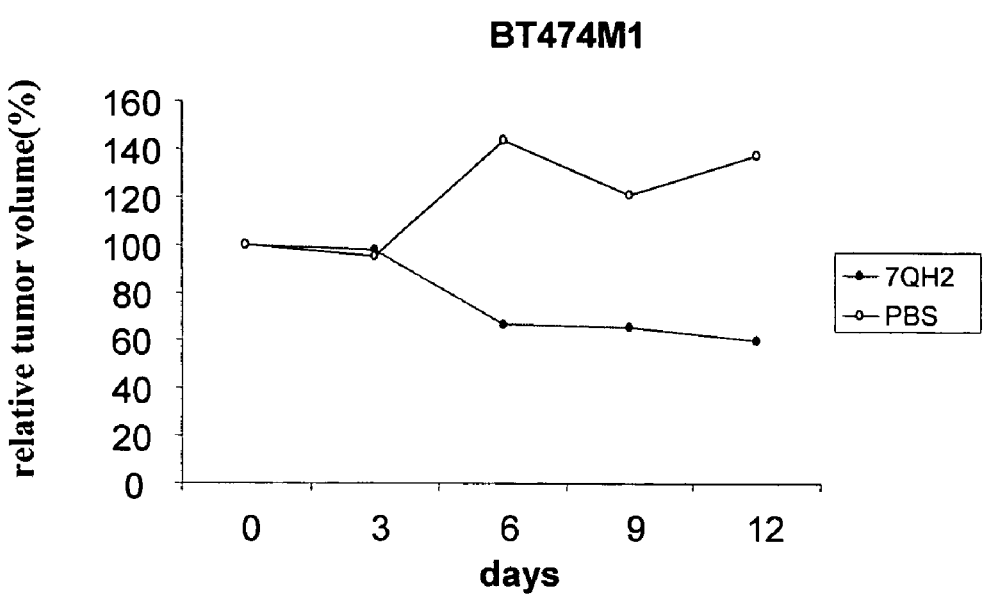
FIG. 17 shows the results of in vivo studies of the effect of adamanolol (7QH2) on tumor size in mice.
Figure 17:
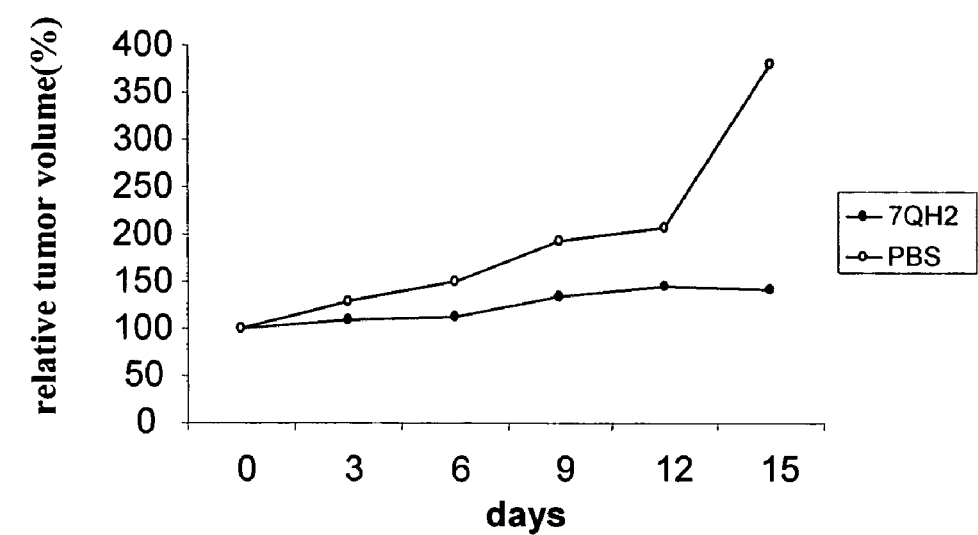

Breast cancer cell lines derived from BT474 after one round (BT474M1) or two rounds (BT474M2) of tumorigenic selection were used. $5 \times 10^6$ cells were injected with Matrigel into mammary fat pads of nude mice. Two tumors were inoculated for each animal and each treatment group contained 5 animals. Five weeks after inoculation when the tumors were well established (about 100 $mm^3$ in average) the treatment started (day 0 in the figure). Each mouse received adamanolol (7QH2) at a daily dose of 20 mg/kg through intraperitoneal injection for 5 consecutive days in each week for two weeks. Tumor volumes were measured every three days. The percentile of the tumor volume related to the initial volume at day 0 was plotted for each time point. Results are shown in FIG. 17. Adamanolol is a potent tumor growth inhibitor of HER-2/neu-overexpressing cancer cells in vivo. These results show a significant growth suppression of BT474 cells by the treatment.

Example 16

Figure 18:
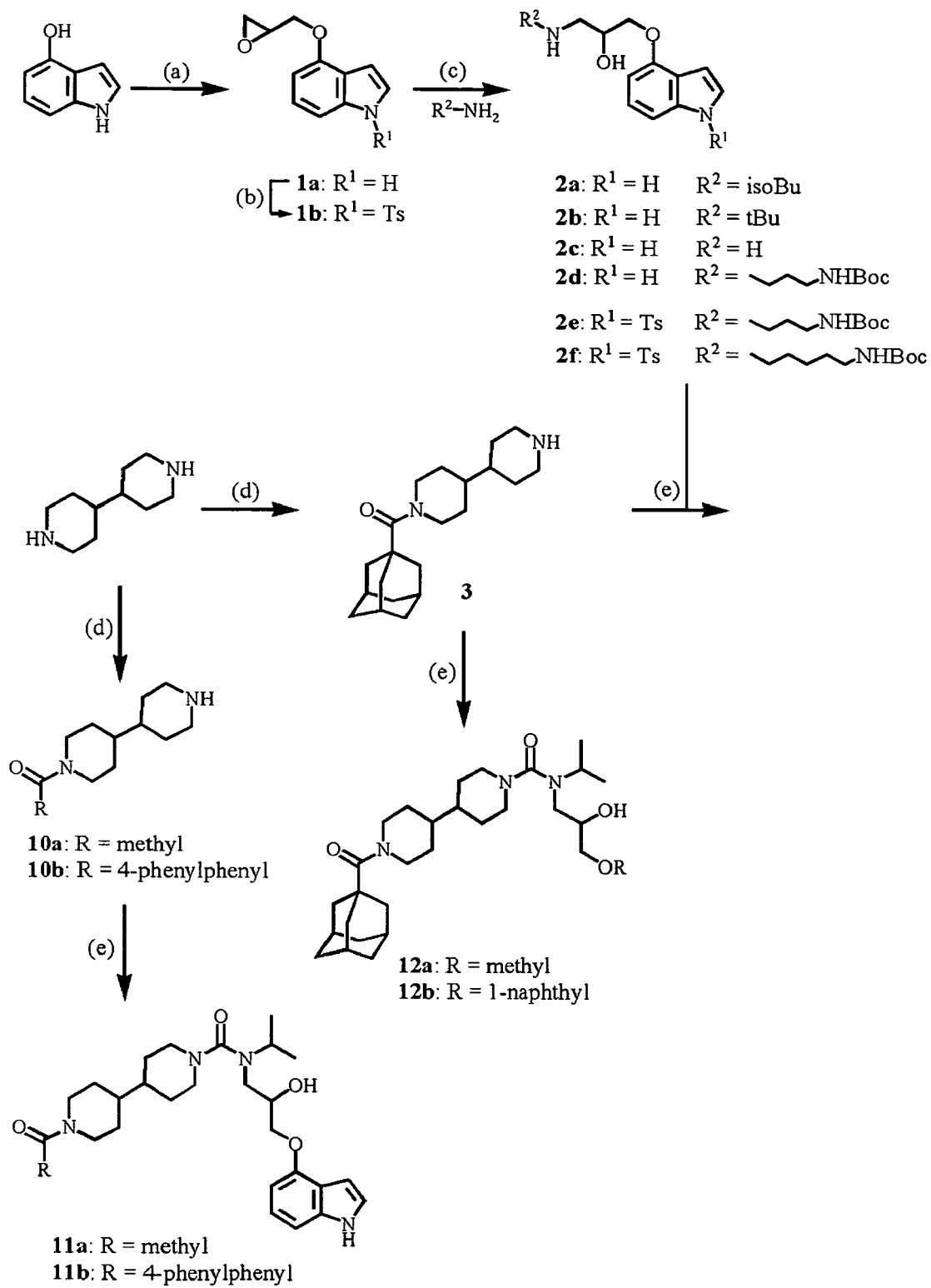
FIG. 18 shows the synthetic scheme for several adamanolol derivatives.
Figure 18:
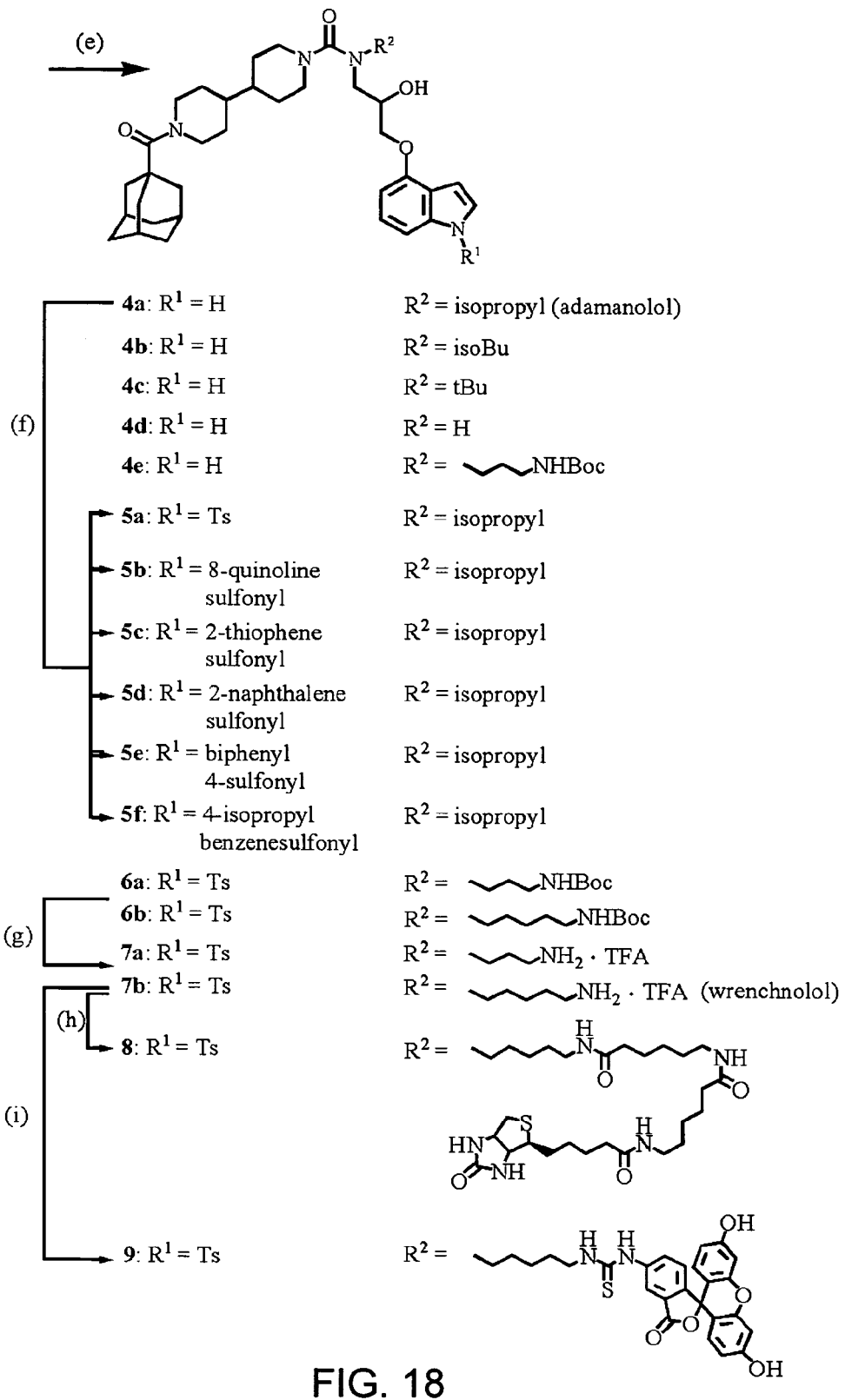

Synthesis of Adamanolol Derivatives in FIG. 18

The synthesis of adamanolol and its derivatives is summarized in FIG. 18. Coupling of 4-hydroxyindole and epichlorohydrin afforded glycidyl 4-indolyl ether (FIG. 18 compound 1a) quantitatively. The ether (FIG. 18 compound 1a) was reacted with isobutylamine, tert-butylamine, ammonia, or mono-N-Boc-1,3-propanediamine to give the corresponding amines 2a-d. Pindolol, amine compounds 2a-d, propranolol, N-(3-methoxy-2-hydroxypropyl)isopropylamine, or N-[3-(1-naphthyloxy)-2-hydroxypropyl]isopropylamine were then coupled with amide (FIG. 18 compound 3) through the conversion of compound 3 to an imidazolide and its N-activation by methyl iodide. The coupling resulted in the formation of a urea linkage to afford adamanolol and its analogs, compounds 4a-e and 12a-b. The sulfonyl analogs of adamanolol (FIG. 18 compounds 5a-f) were prepared by reacting adamanolol with the corresponding sulfonyl chlorides.

The amide FIG. 18 compound 3 was obtained by coupling adamantanecarbonyl chloride with 4,4'-bipiperidine. Reaction of acetic anhydride or 4-biphenylcarbonyl chloride instead of adamantanecarbonyl chloride yielded amides as shown in FIG. 18, compound 10a and compound 10b, which were converted to compound 11a and compound 11b, respectively.

Example 17

General Synthetic Methods

Compounds as described in FIG. 18 were synthesized and analyzed as described below in Example 18 to Example 28. Compounds 11c,d and compound 13 were purchased from Tripos and Sigma, respectively. The solvents used for chemical synthesis were dried prior to use. All other chemicals were used as received without purification. All moisture-sensitive reactions were performed in flame-dried and/or oven-dried glassware under a positive pressure of nitrogen unless otherwise noted. Thin-layer chromatography was carried out with glass TLC plates precoated with Merck silica gel 60 F254. Column chromatography was accomplished with Fuji Silysia Chemical silica gel BW820MH. Proton nuclear magnetic resonance spectra were recorded in deuterated solvents at 270 or 600 MHz. High-resolution mass spectra were obtained by Q-star spectrometer (Applied Biosystems) on an ESI mode.

Example 18

Glycidyl 4-indolyl ether (Compound 1a)

To a solution of 4-hydroxyindole (0.50 g, 3.8 mmol) in dimethylsulfoxide (10 mL) at 45° C. were added potassium hydroxide (0.43 g, 7.6 mmol) and then epichlorohydrin (1.4 g, 15.2 mmol). After being stirred at 45° C. for 4 h, the reaction mixture was diluted with a saturated solution of $NH_4Cl$ and extracted with diethyl ether (3×50 mL). The combined organic layers were dried with $Na_2SO_4$, and concentrated. The residue was purified by column chromatography on silica gel with benzene/acetone mixtures to give the glycidyl 4-indolyl ether (compound 1a) (0.75 g, quant) as a colorless oil. See FIG. 18.

IR (thin film) data was as follows: 3402, 2923, 1497, 1362, 1244 $cm_{-1}$; $^1H$ NMR data was as follows: ($CDCl_3$, 270 MHz) $\delta_H$ 8.17 (br. s, 1H), 7.14-7.03 (m, 3H), 6.70 (t, J=2.0 Hz, 1H), 6.62 (dd, J=1.1, 7.0 Hz, 1H), 4.35 (dd, J=3.5, 11.1 Hz, 1H), 4.16 (dd, J=5.4, 11.1 Hz, 1H), 3.46 (m, 1H), 2.94 (dd, J=4.1, 4.9, 1H), 2.82 (dd, J=2.7, 4.9, 1H); HRMS (ESI) Exact mass calculated for $C_{11}H_{11}NO_2$+H requires m/z 190.0868. Found m/z 190.0842.

Example 19

Preparation of Glycidyl N-tosyl-4-indolyl ether (Compound 1b)

A solution of glycidyl 4-indolyl ether (compound 1a) (1.0 g, 5.3 mmol) in THF (5 mL) was cooled to 0° C., and sodium hydride in mineral oil (60%, 0.42 g, 10.6 mmol) and tosyl chloride (1.2 g, 6.3 mmol) were added. After being stirred at this temperature for 1 h, the reaction mixture was allowed to warm to room temperature and stirred for 2 hours. The reaction mixture was diluted with water and extracted with $CHCl_3$ (3.50 mL). The combined organic layers were dried with $Na_2SO_4$ and concentrated. The residue was purified by column chromatography on silica gel with benzene/acetone mixtures to give the glycidyl N-tosyl-4-indolyl ether (compound 1b) (1.5 g, 82%) as a white solid. See FIG. 18.

IR (thin film) data was as follows: 2930, 1362, 1189, 1137, $cm_{-1}$; $^1H$ NMR data was as follows: ($CDCl_3$, 270 MHz) $\delta_H$ 7.75 (d, J=8.4 Hz, 2H), 7.61 (d, J=8.4 Hz, 1H), 7.46 (d, J=3.8 Hz, 1H), 7.21 (d, J=8.4 Hz, 2H), 7.23 (t, J=8.4 Hz, 1H), 6.80 (d, J=3.8 Hz, 1H), 6.63 (d, J=8.4 Hz, 1H), 4.32 (dd, J=3.2, 11.1 Hz, 1H), 4.03 (dd, J=5.7, 11.1 Hz, 1H), 3.38 (m, 1H), 2.91 (t, J=4.9 Hz, 1H), 2.77 (dd, J=2.7, 4.9 Hz, 1H), 2.34 (s, 3H); HRMS (ESI) Exact mass calcd for $C_{18}H_{17}NO_4S$+H requires m/z 344.0957. Found m/z 344.0944.

Example 20

N-[3-(4-indolyloxy)-2-hydroxypropyl]-isobutylamine (Compound 2a)

To a solution of glycidyl 4-indolyl ether (compound 1a) (215 mg, 1.1 mmol) in methanol (2 mL) was added isobutylamine (160 mg, 2.2 mmol). The solution was heated to 100° C. and stirred for 32 h. The product was purified by column chromatography on silica gel with $CHCl_3$/methanol mixtures to give the corresponding amine (2a) (120 mg, 42%) as a colorless oil. See FIG. 18.

IR (thin film) data was as follows: 3404, 2954, 1508, 1363 $cm_{-1}$; $^1H$ NMR data was as follows: ($CDCl_3$, 270 MHz) $\delta_H$ 8.24 (br. s, 1H), 7.12-7.02 (m, 3H), 6.65 (t, J=2.4 Hz, 1H), 6.51 (dd, J=1.0, 7.3 Hz, 1H), 4.30 (m, 1H), 4.21-4.09 (m, 2H), 3.43 (br. s, 2H) 3.05 (dd, J=3.8, 12.4 Hz, 1H), 2.96 (dd, J=7.8, 12.4 Hz, 1H), 2.61 (dd, J=2.7, 11.9 Hz, 1H), 2.57 (dd, J=2.7, 11.9 Hz, 1H), 1.90 (m, 1H), 0.97 (d, J=6.8 Hz, 3H), 0.96 (d, J=6.8 Hz, 3H); HRMS (ESI) Exact mass calcd for $C_{15}H_{22}N_2O_2$+H requires m/z 263.1760. Found m/z 263.1778.

Example 21

N-[3-(N-tosyl-4-indolyloxy)-2-hydroxypropyl]-N'-Boc-1,5-pentanediamine (FIG. 16 Compound 2f)

The reaction of glycidyl N-tosyl-4-indolyl ether (1b) (1.7 g, 5.0 mmol) and mono-N-Boc-1,5-pentanediamine (2.0 g, 10 mmol) as described for 2a gave the title compound (2f) (1.7 g, 63%) as a colorless oil. See FIG. 18.

IR (thin film) data was as follows: 3426, 2932, 1684, 1508, 1364, 1160 $cm_{-1}$; $^1H$ NMR data was as follows: ($CDCl_3$, 270 MHz) $\delta_H$ 7.74 (d, J=8.4 Hz, 2H), 7.60 (d, J=8.4 Hz, 1H), 7.46 (d, J=3.8 Hz, 1H), 7.20 (d, J=8.4 Hz, 2H), 7.19 (t, J=8.4 Hz, 1H), 6.76 (d, J=3.8 Hz, 1H), 6.64 (d, J=8.4 Hz, 1H), 4.54 (s, 1H), 4.07 (m, 3H), 3.10 (br. m, 2H), 2.89 (dd, J=3.5, 12.4 Hz, 1H), 2.78 (dd, J=7.0, 12.4 Hz, 1H), 2.65 (dt, J=2.4, 4.3 Hz, 2H), 2.63 (s, 3H), 2.08 (br. s, 3H), 1.60-1.28 (m, 6H), 1.44 (s, 9H); HRMS (ESI) Exact mass calcd for $C_{28}H_{39}N_3O_6S$+H requires m/z 546.2638. Found m/z 546.2640.

Example 22

Preparation of Amide Compound 3

To a solution of 4,4'-bipiperidine (0.84 g, 5.0 mmol) and triethylamine (2 mL) in $CHCl_3$ (150 mL) was added a solution of 1-adamantanecarbonyl chloride (0.50 g, 2.5 mmol) in $CHCl_3$ (50 mL). The resulting mixture was refluxed for 0.5 h, diluted with water, and extracted with $CHCl_3$ (3.100 mL). The combined extracts were dried over $Na_2SO_4$ and then concentrated in vacuum. The residue was purified by column chromatography on silica gel with methanol/aqueous ammonia mixtures to give amide 3 (750 mg, 90%) as a colorless oil. See FIG. 18.

IR (thin film) data was as follows: 3421, 2902, 1617 $cm_{-1}$; $^1H$ NMR data was as follows: ($CDCl_3$, 270 MHz) $\delta_H$ 4.46 (br. d, J=13.0 Hz, 2H), 3.02 (br. d, J=11.6 Hz, 2H), 2.91 (br. s, 1H), 2.59 (br. t, J=11.9 Hz, 2H), 2.47 (br. t, J=111.9 Hz, 2H), 1.95 (br. s, 3H), 1.90 (br. s, 6H), 1.63 (br. s, 10H), 1.19-1.02 (br. m, 6H); HRMS (ESI) Exact mass calcd for $C_{21}H_{34}N_2O$+H requires m/z 331.2749. Found m/z 331.2753.

Example 23

Preparation of Adamanolol (4a)

To a solution of amide 3 (120 mg, 0.36 mmol) in THF (10 mL) was added 1,1'-carbonyldiimidazole (240 mg, 1.46 mmol). After being refluxed for 4 h, the mixture was diluted with $CHCl_3$ (20 mL) and washed with water (3.20 mL). The organic layer was dried with $Na_2SO_4$ and concentrated to give carbamoyl imidazole, which was used without further purification. A solution of carbamoyl imidazole and MeI (0.5 mL) in MeCN (2 mL) was stirred for 18 h at room temperature. Evaporation of the solvent and excess MeI in vacuum gave the corresponding imidazolium salt. To a solution of imidazolium salt in $CH_2Cl_2$ (2 mL) were added pindolol (268 mg, 1.08 mmol) and $Et_3N$ (0.5 mL). After being stirred at room temperature for 30 h, the mixture was concentrated and purified by column chromatography on silica gel with $CHCl_3$/methanol mixtures to give adamanolol (4a) (145 mg, 67%) as a colorless oil. See FIG. 18.

IR (thin film) data was as follows: 3450, 2907, 1624, 1428, 1245 $cm_{-1}$; $^1H$ NMR data was as follows: ($CDCl_3$, 270 MHz) $\delta_H$ 8.57 (br. s, 1H), 7.11-7.04 (m, 3H), 6.59 (t, J=2.4 Hz, 1H), 6.52 (dd, J=2.7, 5.7 Hz, 1H), 5.29 (br. m, 1H), 4.53 (br. d, J=13.5 Hz, 2H), 4.45-4.25 (m, 2H), 4.12 (br. m, 2H), 3.44 (dd, J=1.4, 13.5 Hz, 1H), 3.35-3.10 (m, 2H), 2.82-2.50 (br. m, 4H), 2.03 (br. s, 3H), 1.99 (br. s, 6H), 1.72 (s, 6H), 1.80-1.44 (br. m, 4H), 1.35 (d, 6.5 Hz, 3H), 1.32 (d, J=6.5 Hz, 3H), 1.45-0.86 (m, 6H); HRMS (ESI) Exact mass calcd for $C_{36}H_{52}N_4O_4$+H requires m/z 605.4067. Found m/z 605.4065.

Example 24

Preparation of N-tosyladamanolol (5a)

A solution of adamanolol (4a) (30.1 mg, 0.05 mmol) in THF (1 mL) was cooled to 0° C., and sodium hydride in mineral oil (60%, 12 mg, 0.50 mmol) and tosyl chloride (9.5 mg, 0.05 mmol) were added. After being stirred at this temperature for 0.5 h, the reaction mixture was allowed to warm to room temperature and stirred for 2 h. The reaction mixture was diluted with brine and extracted with $CH_2Cl_2$ (3.20 mL). The combined organic layers were dried with $Na_2SO_4$ and concentrated. The residue was purified by column chromatography on silica gel with $CHCl_3$/methanol mixtures to give the N-tosyladamanolol (Sa) (21.5 mg, 57%) as a colorless oil. See FIG. 18.

IR (thin film) data was as follows: 3434, 2910, 2852, 1623, 1427, 1188 $cm_{-1}$; $^1H$ NMR data was as follows: ($CDCl_3$, 270 MHz) $\delta_H$ 7.75 (d, J=8.4 Hz, 2H), 7.57 (d, J=8.4 Hz, 1H), 7.45 (d, J=3.5 Hz, 1H), 7.21 (d, J=8.4 Hz, 2H), 7.20 (dd, J=7.8, 8.4 Hz, 1H), 6.75 (d, J=3.5 Hz, 1H), 6.68 (d, J=7.8 Hz, 1H), 5.14 (br. m, 1H), 4.55 (br. d, J=13.0 Hz, 2H), 4.24 (br. d, J=4.6 Hz, 2H), 4.32-3.94 (br. m, 2H), 2.96 (m, 2H), 2.82 (m, 1H), 2.75-2.54 (br. m, 4H), 2.34 (s, 3H), 2.03 (br. s, 3H), 1.99 (br. s, 6H), 1.72 (s, 6H), 1.80-1.44 (hr. m, 4H), 1.45-0.86 (m, 6H), 1.04 (d, J=6.5 Hz, 6H); HRMS (ESI) Exact mass calcd for $C_{43}H_{58}N_4O_6S$+H requires m/z 759.4155. Found m/z 759.4138.

Example 25

Preparation of N-Boc-wrenchnolol with an Aminopropyl Handle (6a)

The reaction of N-[3-(N-tosyl-4-indolyloxy)-2-hydroxypropyl]-N'-Boc-1,3-propanediamine (2e) (460 mg, 0.89 mmol) and mono amide 3 (250 mg, 0.76 mmol) as described for 4a gave the title compound (6a) (353 mg, 53%) as a colorless oil. See FIG. 18.

IR (thin film) data was as follows: 3441, 1633 cm$_{-1}$; $^1$H NMR data was as follows: (CDCl$_3$, 270 MHz) δ$_H$ 7.75 (d, J=8.4 Hz, 2H), 7.59 (d, J=8.4 Hz, 1H), 7.46 (d, J=3.8 Hz, 1H), 7.26-7.17 (m, 3H), 6.74 (d, J=3.8 Hz, 1H), 6.67 (d, J=8.4 Hz, 1H), 5.26 (br. m, 1H), 5.10 (br. s, 1H), 4.55 (br. d, J=13.0 Hz, 2H), 4.29 (br. m, 2H), 4.30-3.85 (br. m, 2H), 3.25-3.05 (br. m, 2H), 2.95-2.78 (br. m, 2H), 2.78-2.55 (br. m, 6H), 2.34 (s, 3H), 2.03 (br. s, 3H), 1.99 (br. s, 6H), 1.90-1.55 (br. m, 6H), 1.72 (s, 6H), 1.40 (s, 9H), 1.30-0.70 (br. m, 6H); HRMS (ESI) Exact mass calcd for C$_{48}$H$_{67}$N$_5$O$_8$S+H requires m/z 874.4789. Found m/z 874.4778.

Example 25

Preparation of N-Boc-wrenchnolol (Compound 6b)

The reaction of N-[3-(N-tosyl-4-indolyloxy)-2-hydroxypropyl]-N'-Boc-1,5-pentanediamine (compound 2f) (500 mg, 0.92 mmol) and mono amide (compound 3) (250 mg, 0.76 mmol) as described for compound 4a gave the title compound (compound 6b) (322 mg, 47%) as a colorless oil. See FIG. 18.

IR (thin film) 3445, 2933, 1684, 1617, 1428 cm$_{-1}$; $^1$H NMR data was as follows: (CDCl$_3$, 270 MHz) δ$_H$ 7.75 (d, J=8.4 Hz, 2H), 7.59 (d, J=7.8 Hz, 1H), 7.46 (d, J=3.8 Hz, 1H), 7.21 (d, J=8.4 Hz, 2H), 7.26-7.19 (t, J=7.8 Hz, 1H), 6.74 (d, J=3.8 Hz, 1H), 6.67 (d, 1H), 5.18 (br. m, 1H), 4.55 (br. m, 1H), 4.55 (br. d, J=12.7 Hz, 2H), 4.24 (br. d, J=4.6 Hz, 2H), 4.32-3.87 (br. m, 2H), 3.17-2.91 (m, 4H), 2.79-2.52 (m, 6H), 2.34 (s, 3H), 2.03 (br. s, 3H), 1.99 (br. s, 6H), 1.72 (s, 6H), 1.44 (s, 9H), 1.80-0.86 (m, 16H); HRMS (ESI) Exact mass calcd for C$_{50}$H$_{71}$N$_5$O$_8$S+H requires m/z 902.5102. Found m/z 902.5100.

Example 26

Wrenchnolol with an Aminopropyl Handle (Compound 7a)

A solution of 6a (350 mg, 0.40 mmol) in CHCl$_3$ (3 mL) was added TFA. This solution was stirred at room temperature for 15 min, then concentrated in vacuum, which was used without further purification to give 7a (360 mg, quant) as a colorless oil. See FIG. 18.

IR (thin film) data was as follows: 3436, 1630 cm$_{-1}$; $^1$H NMR data was as follows: (CDCl$_3$—CD$_3$OD/4:1, 270 MHz) δ$_H$ 7.62 (d, J=8.4 Hz, 2H), 7.47 (d, J=8.1 Hz, 1H), 7.35 (d, J=3.8 Hz, 1H), 7.24 (t, J=8.1 Hz, 1H), 7.11 (d, J=8.4 Hz, 2H), 6.66 (d, J=3.8 Hz, 1H), 6.56 (d, J=8.1 Hz, 1H), 5.24 (br. m, 1H), 4.40 (br. d, J=11.9 Hz, 2H), 4.17 (br. m, 2H), 4.05-3.72 (br. m, 2H), 3.31 (br. m, 2H), 3.04 (br. m, 2H), 2.91 (br. m, 2H), 2.78-2.42 (br. m, 4H), 2.22 (s, 3H), 2.05 (br. m, 2H), 1.91 (br. s, 3H), 1.85 (br. s, 6H), 1.70-1.30 (br. m, 4H), 1.57 (s, 6H), 1.30-0.60 (br. m, 6H); HRMS (ESI) Exact mass calcd for C$_{43}$H$_{59}$N$_5$O$_6$S+H requires m/z 774.4264. Found m/z 774.4286.

Example 27

Preparation of Wrenchnolol (Compound 7b)

The reaction of N-Boc-wrenchnolol (6b) (320 mg, 0.36 mmol) as described for compound 7(a) gave the title compound (7b) (325 mg, quant) as a colorless oil. See FIG. 18.

IR (thin film) data was as follows: 3444, 2910, 1635, 1428 cm$_{-1}$; $^1$H NMR data was as follows: (CDCl$_3$, 270 MHz) δ$_H$ 7.75 (d, J=8.1 Hz, 2H), 7.58 (d, J=8.1 Hz, 1H), 7.46 (d, J=3.8 Hz, 1H), 7.21 (d, J=8.1 Hz, 2H), 7.13-7.02 (dd, J=7.8, 8.1 Hz, 1H), 6.74 (d, J=3.8 Hz, 1H), 6.65 (d, J=7.8 Hz, 1H), 5.30 (br. m, 1H), 4.54 (br. m, 1H), 4.54 (br. d, J=12.7 Hz, 2H), 4.24 (br. d, J=4.3 Hz, 2H), 4.32-3.81 (br. m, 2H), 3.08 (br. d, J=5.4 Hz, 1H), 2.85 (br. t, J=5.4 Hz, 1H), 2.81-2.52 (br. m, 8H), 2.34 (s, 3H), 1.99 (br. s, 9H), 1.72 (br. s, 6H), 1.79-0.70 (m, 16H); HRMS (ESI) Exact mass calculated for C$_{45}$H$_{63}$N$_5$O$_6$S+H requires m/z 802.4577. Found m/z 802.4550.

Example 28

Preparatiom of Conjugated Wrenchnolol (8)

To a solution of wrenchnolol (7b) (5.0 mg, 0.006 mmol) and triethylamine (0.1 mL) in DMSO (0.25 mL) were added 4-(dimethylamino)pyridine (0.1 mg), N,N'-dicyclohexylcarbodiimide (2.5 mg, 0.012 mmol), and a biotin-XX-NHS (6.8 mg, 0.012 mmol). This solution was stirred at room temperature overnight, diluted with brine, and extracted with CHCl$_3$ (3.10 mL). The combined extracts were dried over Na$_2$SO$_4$ and then concentrated in vacuum. The residue was purified by column chromatography on silica gel with CHCl$_3$/methanol mixtures to give the corresponding amide (8) (7.2 mg, 95%) as a colorless oil. See FIG. 18.

IR (thin film) data was as follows: 3284, 2933, 1684, 1653, 1559, 1541 cm$_{-1}$; $^1$H NMR data was as follows: (CD$_3$OD, 270 MHz) δ$_H$ 7.79 (d, J=8.6 Hz, 2H), 7.60 (d, J=8.1 Hz, 1H), 7.56 (d, J=4.0 Hz, 1H), 7.31 (d, J=8.6 Hz, 2H), 7.21 (t, J=8.1 Hz, 1H), 6.79 (d, J=4.0 Hz, 1H), 6.77 (d, J=8.1 Hz, 1H), 5.38 (br. m, 1H), 4.60-4.42 (br. m, 3H), 4.38-4.20 (br. m, 3H), 4.16-3.89 (br. m, 2H), 3.47 (br. m, 2H), 3.24-3.01 (br. m, 9H), 2.91 (dd, J=5.0, 12.8 Hz, 1H), 2.85-2.54 (br. m, 5H), 2.34 (s, 3H), 2.24-2.08 (br. m, 6H), 2.00 (br. s, 9H), 1.77 (br. s, 6H), 1.90-0.40 (m, 34H); HRMS (ESI) Exact mass calcd for C$_{67}$H$_{99}$N$_9$O$_{10}$S$_2$+H requires m/z 1254.7035. Found m/z 1254.7010.

To a solution of wrenchnolol (7b) (10 mg, 0.012 mmol) and triethylamine (0.2 mL) in THF (1 mL) was added fluorescein isothiocyanate (5.6 mg, 0.014 mmol). This solution was stirred at room temperature for 8 h and then concentrated in vacuum. The residue was purified by column chromatography on silica gel (CHCl3/methanol) and ODS silica gel (70% MeOH, 0.1% TFA) to give the fluorescein conjugate (9) (8.3 mg, 58%) as a yellow solid. See FIG. 18.

IR (thin film) data was as follows: 3421, 2910, 1636 cm$_{-1}$; $^1$H NMR data was as follows: (CD$_3$OD, 270 MHz) δ$_H$ 8.31 (br. s, 0.6H), 8.19 (br. s, 0.4H), 7.83 (m, 1H), 7.73 (d, J=8.4 Hz, 2H), 7.53 (d, J=8.4 Hz, 1H), 7.46 (d, J=3.8 Hz, 1H), 7.25 (d, J=8.4 Hz, 2H), 7.38-6.57 (m, 10H), 5.55 (br. m, 1H), 4.45 (br. d, J=12.7 Hz, 2H), 4.40-4.20 (br. m, 2H), 4.20-3.91 (br. m, 4H), 3.91-3.52 (br. m, 2H), 3.40-3.20 (br. m, 2H), 2.81-2.47 (br. m, 4H), 2.29 (s, 3H), 1.95 (br. s, 9H), 1.72 (br. s, 6H), 1.67-0.45 (m, 16H); HRMS (ESI) Exact mass calcd for C$_{66}$H$_{74}$N$_6$O$_{11}$S$_2$+H requires m/z 1191.4935. Found m/z 1191.4939.

Example 29

Cell Viability Assays

SK-BR3 breast cancer cells were plated on 96-well plates at density of $5 \times 10^3$ cells/well and maintained for 24 hrs. The cells were then incubated with varied concentrations of each compound for 48 hrs, followed by addition of Premix WST-1 Solution (Takara). Cell viability was estimated by measuring absorbance at 450 nm after 1 hr with a SPECTRAmax microplatereader.

Example 30

Transcription Reporter Gene Assay mammalian expression vectors, each encoding the activation domain of ESX, VP16, or NF-κB p65 fused with the GAL4 DNA-binding domain (amino acids 1-94), were used. Each expression construct was co-transfected to HEK293Tag human kidney cells together with a reporter plasmid in which the production of secreted alkaline phosphatase (SEAP) is under control of an IL2 promoter carrying five GAL4 binding sites. After 10-hr incubation with wrenchnolol (20 μM), an aliquot of the culture was assayed for SEAP activity.

Example 31

Effects of Wrenchnolol on the Expression Levels of Her2

SK-BR3 cells were treated by 7 μM of wrenchnolol for 24 hrs, and whole cell lysates were analyzed by western blots. The primary antibodies used for the western analysis were a monoclonal antibody against Her2 (c-neu-Ab-3; Oncogene Science) and a monoclonal antibody against á-tublin (Molecular Probes). The blotted membranes were then visualized with ECL chemiluminescence detection reagents (Amersham Bioscience).

Example 32

Sur-2 Interaction of a Biotin Conjugate of Wrenchnolol (8)

HeLa cell nuclear extracts were prepared as described$_{47}$ and incubated with a biotin conjugate of wrenchnolol (8) (100 μM) at 4° C. for 24 hrs. The samples were incubated with Neutravidin affinity resin (Pierce) at 4° C. for 2 hrs and extensively washed with PBS buffer containing 0.5% Nonidet P-40. The bound proteins were then separated by SDS/PAGE and analyzed by western blots with an antibody against human Sur-2 or by silver-staining.

$$A = A_o + 0.5 \cdot e([9]_o + (([9]_o + [P]_o K_d)_2 - 4[9]_o [P]_o)_{0.5})$$

Where A and $A_o$ are the values of fluorescence intensity of 9 in the presence or absence of GST-Sur2$_{352-625}$, respectively, and .e is the differential fluorescence intensity of 1 μM of 9 in the presence of an infinite concentration of protein and in its absence. $[9]_o$ and $[P]_o$ are the total concentrations of 9 and protein added, respectively.

Example 33

NMR Studies

Wrenchnolol (7b) or its aminopropyl analog (7a) (0.5 mg) was dissolved in 0.5 mL of a phosphate buffered saline (PBS) solution (99.99% $D_2O$, pD=6.8). Complete assignments of the proton signals were achieved by a combination of NOESY, DQF-COSY, and HOHAHA experiments (Table S1). A model structure of 7a was acquired using energy minimization with CVFF force field in the Insight 2000 program (Accelrys) and adjusted on the basis of NOE connectivities and J coupling constants. A concentrated PBS solution of GST-Sur2$_{352-625}$ was gradually added to an NMR sample of wrenchnolol (7b), and a 1D $_1H$ spectrum was collected after each addition of the protein. NMR experiments were performed on a Bruker Avance 600 MHz spectrometer. The data were processed using FELIX (Accelrys) and UXNMR (Bruker), and proton chemical shifts were referenced to the HOD resonance (4.70 ppm at 298 K; temperature correction factor: −0.0109 ppm/K). All 1D $_1H$ NMR spectra were recorded with 12 ppm spectral width, 8192 data points, and 298 K temperature. Suppression of the HOD resonance was achieved by an excitation sculpting gradient pulse. Two-dimensional experiments of DQF-COSY, HOHAHA (88-ms mixing time), and NOESY (150 and 300-ms mixing times) were recorded with 4096 data points in the $t_2$ dimension and 512 increments. A 90°-phase shifted sine bell function was used in the $t_2$ and $t_1$ dimensions prior to Fourier transformation of NOESY, while a 30° phase shifted skewed sine bell function was for HOHAHA and DQF-COSY. The final spectral matrices consisted of 1,024. 1,024 of the $_1H$ frequency (F2 and F1) dimensions.

Example 34

Cellular Distribution of Wrenchnolol

SK-BR-3 cells grown on cover slips were treated with 10 μM of FITC-conjugate 9 for 1 h. After washing with ice-cold PBS twice, the cells were fixed with 100% methanol at −20° C. for 20 min. The cells were co-stained with DAPI. Fluorescence images of the cells were captured by a Zeiss Axiovert 200M fluorescence microscope.

Example 35

Structure-Activity Relationship in Cells and In Vitro

Structure-activity relationship of adamanolol derivatives is summarized in Table 1.

TABLE 1

Structure-activity relationship of adamanolol derivatives

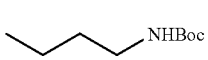

| Compound | R¹ | R² | R³ | $IC_{50}$ (cell) (µM) | $IC_{50}$ (in vitro) (µM) |
|---|---|---|---|---|---|
| 4a (adamanolol) | 1-H-indol-4-yl | isopropyl | adamantyl | 6.4 ± 1.8 | 15.4 ± 0.3 |
| 4b | 1-H-indol-4-yl | isobutyl | adamantyl | 4.1 ± 0.2 | 15.1 ± 0.8 |
| 4c | 1-H-indol-4-yl | tert-butyl | adamantyl | 7.6 ± 1.5 | ND |
| 4d | 1-H-indol-4-yl | H | adamantyl | >100 | >40 |
| 4e | 1-H-indol-4-yl | 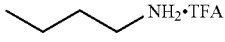 NHBoc | adamantyl | 11.7 ± 0.1 | 11.9 ± 0.7 |
| 5a | 1-tosyl-1-H-indol-4-yl | isopropyl | adamantyl | 2.7 ± 0.3 | 10.0 ± 1.0 |
| 5b | 1-(8-quinolinesulfonyl)-1-H-indol-4-yl | isopropyl | adamantyl | 5.0 ± 0.3 | 12.0 ± 0.9 |
| 5c | 1-(2-thiophenesulfonyl)-1-H-indol-4-yl | isopropyl | adamantyl | 6.4 ± 1.5 | ND |
| 5d | 1-(2-naphthalenesulfonyl)-1-H-indol-4-yl | isopropyl | adamantyl | 9.7 ± 0.4 | ND |
| 5e | 1-(biphenyl-4-sulfonyl)-1-H-indol-4-yl | isopropyl | adamantyl | 5.3 ± 0.2 | ND |
| 5f | 1-(4-isopropyl-benzenesulfonyl)-1-H-indol-4-yl | isopropyl | adamantyl | 4.9 ± 0.4 | ND |
| 7a | 1-tosyl-1-H-indol-4-yl | $\sim\sim\sim$ NH₂·TFA | adamantyl | 4.7 ± 0.1 | 10.2 ± 1.1 |
| 7b (wrenchnolol) | 1-tosyl-1-H-indol-4-yl | $\sim\sim\sim\sim$ NH₂·TFA | adamantyl | 6.9 ± 1.0 | 10.0 ± 1.5 |
| 11a | 1-H-indol-4-yl | isopropyl | methyl | >100 | >40 |
| 11b | 1-H-indol-4-yl | isopropyl | 4-phenylphenyl | 14.8 ± 1.9 | ND |
| 11c | 1-H-indol-4-yl | isopropyl | 2-thenyl | >35 | ND |
| 11d | 1-H-indol-4-yl | isopropyl | p-tolyl | >35 | ND |
| 12a | methyl | isopropyl | adamantyl | >100 | >40 |
| 12b | 1-naphthyl | isopropyl | adamantyl | 10.7 ± 0.6 | ND |

In one group of derivatives (the $R_1$ substituents in Table 1), the indole ring of adamanolol was substituted. Replacement with a methyl group (12a) abolished the ability of adamanolol to kill Her2-positive SK-BR3 breast cancer cells (Table 1) and to block the interaction of ESX with Sur-2 in vitro (FIG. 1), while the derivatives with indole-like pharmacores (5a-f, 12b) retained the biological activity (Table 1). Introduction of an arylsulfonyl group, especially a tosyl group (5a), at the N1 position of the adamanolol indole ring increased the potency in cells and Sur-2-binding activity in vitro, reminiscent of the improved 5-HT receptor-binding activity of N-arylsulfonyl-tryptamines. Although full optimization of the $R_1$ group is still only partly achieved, the observed importance of the indole-mimicking structures is in good agreement with the reported contribution of a tryptophan residue to the specific interaction of ESX with Sur-2.

Figure 19:
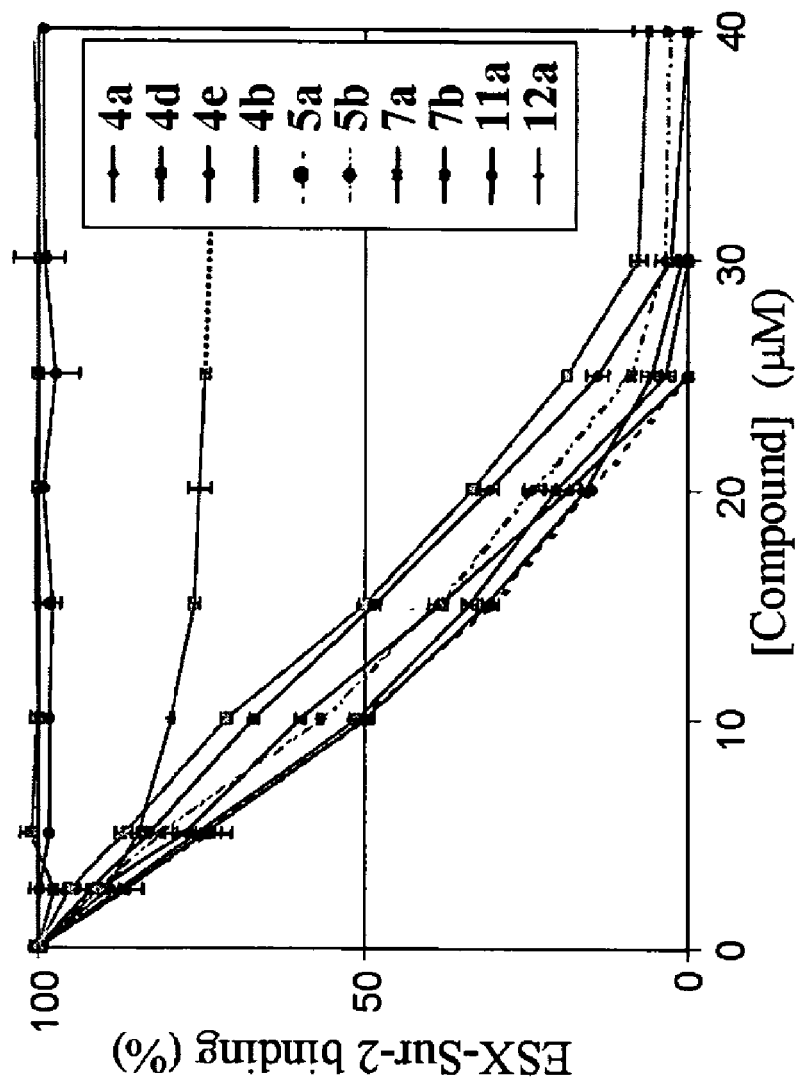
FIG. 19 shows inhibition of the ESX-Sur-2 interaction by adamanolol derivatives.

In another series of derivatives (the $R_3$ substituents in Table 1), the adamantane group of adamanolol was substituted (11a-d). Replacement either with thienyl (11c), tolyl (11d), or methyl (11a) groups resulted in significant loss of the biological activity (Table 1), and the derivative with a methyl group (11a) exhibited almost no ability to block the ESX-Sur-2 interaction in vitro (FIG. 19). The binding fractions were calculated on the basis of fluorescence spectra of FITC-$ESX_{129-145}$ (152 nM) in presence of GST-$Sur2_{352-625}$ (212 nM) and varied concentrations of each adamanolol derivative. The only substituent that retained a comparable level of activity was a biphenyl group (11b), a chemical module often used to mimic nonpolar amino acids.[20-22] The bulky, hydrophobic adamantane group may mimic the cluster of isoleucines and leucines on the face of the ESX helix and perhaps participates in binding to the hydrophobic pocket in Sur-2.

The isopropyl group extended from the urea junction of adamanolol was also replaced by a range of bulky substituents (the $R_2$ substituents in Table 1). These derivatives (4a-c, e) had biological activity comparable to that of adamanolol in cells and inhibited the ESX-Sur-2 interaction in vitro as much as adamanolol. By contrast, simple removal of the isopropyl group (4d) abolished both the biological and Sur-2 binding activity. The analogous consequences of all the bulky substituents and the complete loss of the activity in 4d highlight the importance of the bulkiness of the $R_2$ substituents for activity. A bulky substituent at the $R_2$ position enforces the s-cis configuration around the urea linker, which may bring the indole ring and the adamantane group into close proximity and could form a helix-like nonpolar surface for the interaction with Sur-2.

Example 36

Design of "Wrenchnolol"

Figure 20:
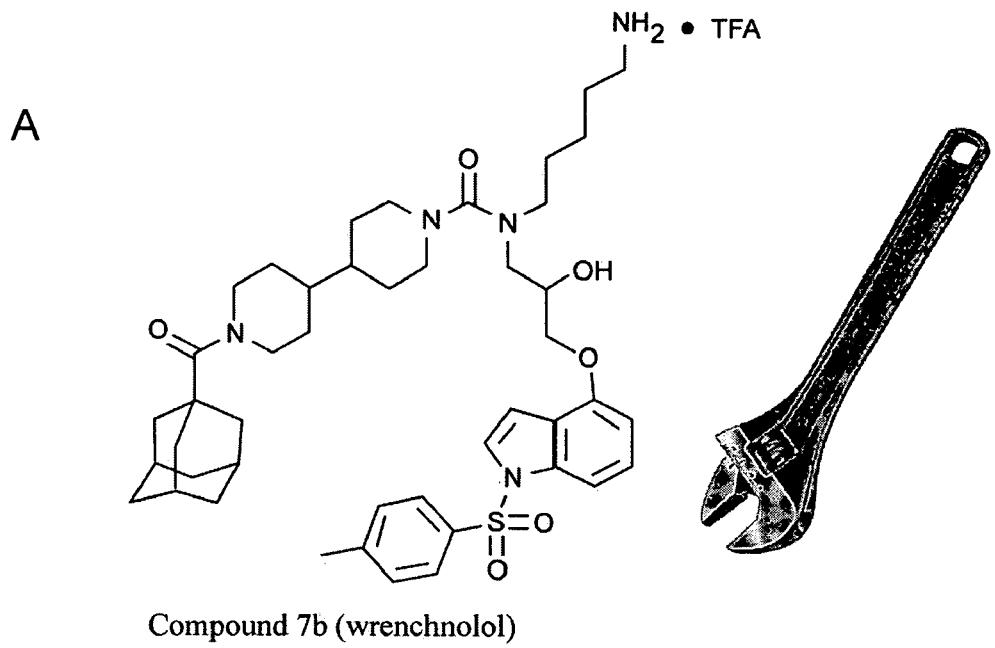
FIG. 20A to FIG. 20C show the design and activity of wrenchnolol.
Figure 20:
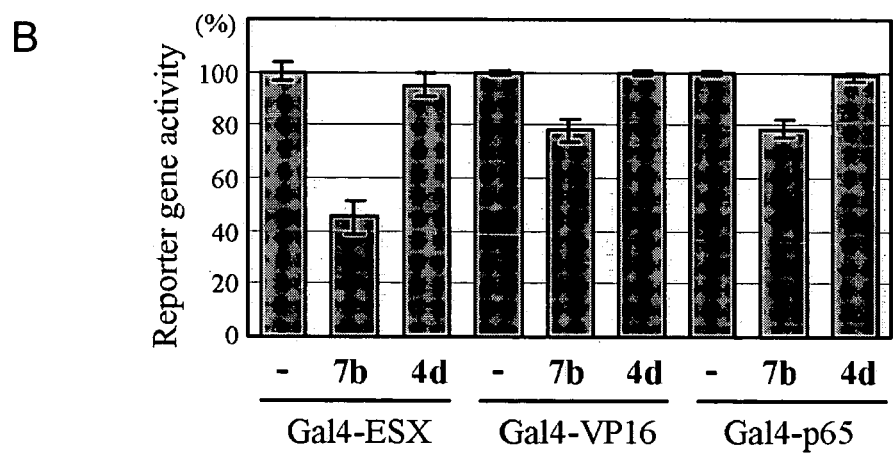
Figure 20:
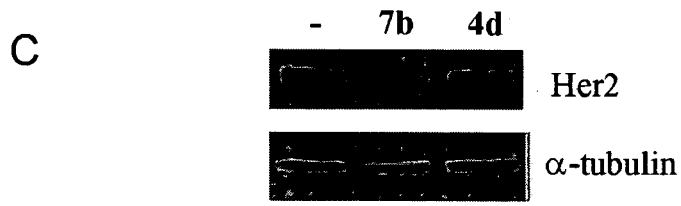
Figure 21:
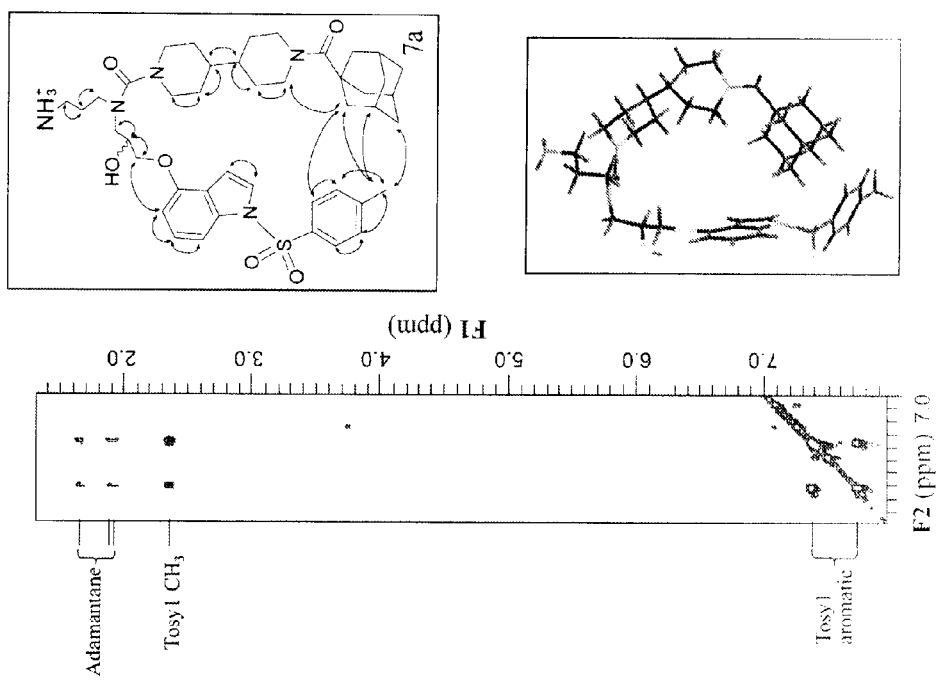

The structure-activity relationship of adamanolol was translated into the design of the second-generation compound that we named wrenchnolol (FIG. 20A). As expected, the wrench-shaped, water-soluble molecule inhibited the ESX-Sur-2 interaction in vitro more strongly than adamanolol, presumably due to the presence of its N-tosyl group (FIG. 19), and was no less active than adamanolol in killing SK-BR3 cells ($IC_{50}$=6.9 μM) despite its increased hydrophilicity (Table 1). Wrenchnolol (20 μM) impaired the ability of the ESX activation domain to stimulate the transcription of a reporter gene in HEK293 cells, whereas it had much milder effects on those of the activation domains of VP16 and NF-KB p65, two functionally irrelevant activation domains structurally similar to the ESX activation domain (FIG. 20B).[18] In contrast, compound 4d (20 μM), which exhibited little activity in killing SK-BR3 cells, had almost no effects on the ESX activation domain (FIG. 20B). SK-BR3 breast cancer cells were treated with wrenchnolol (7 μM) or 4d (15 μM) for 24 h, and cell lysates were analyzed by western blots. Western blot analysis of wrenchnolol-treated SK-BR3 cells showed that wrenchnolol (7b) reduces the expression of the Her2 protein in cells, but not that of alpha-tubulin (FIG. 20C). Although expression of other genes may be influenced by wrenchnolol, these cellular effects are consistent with its inhibition of the ESX-Sur-2 interaction in vitro.

Synthetically, the tosyl group in wrenchnolol protected the labile O-substituted indole from decomposition under acidic conditions and permitted the convenient synthesis of wrenchnolol (7b) (FIG. 18). Glycidyl 4-indolyl ether (1a) was first tosylated to give tosylate 1b, which was then coupled with mono-N-Boc-1,5-pentanediamine to give amine 2f. Carbonyldiimidazole-mediated coupling of amine 2f and amide 3 afforded N-Boc-wrenchnolol (6b), and subsequent acid treatment of 6b furnished wrenchnolol (7b). This stable and water-soluble derivative of adamanolol can readily be synthesized in a large scale and is capable of receiving further modifications through its extended handle. The handle can be protonated when needed or coupled with a fluorescein group or a biotinylated molecule for mechanistic analysis (see below). Wrenchnolol is a chemically tractable bioactive compound that is suited for mechanistic analysis and for further application.

Example 37

NMR Analysis of Wrenchnolol with a Water-Soluble Handle

When the amino group of the handle was protonated, wrenchnolol (7b) and its aminopropyl version (7a) became soluble up to ~1 mM in neutral aqueous solution. The high water solubility enabled NMR analysis of these molecules in a buffered aqueous solution, and their proton signals were completely assigned through a combination of NOESY, DQF-COSY, and HOHAHA data sets (Table S1). NOESY spectra of 7a showed clear long-range NOEs between the adamantane protons and the tosyl protons, demonstrating that these two groups are in close proximity in water (FIGS. 21A, B). DQF-COSY spectra also revealed a highly constrained structure of the arm extended from the indole ring.

Molecular modeling with the NMR constraints supported the s-cis configuration of the urea linker and a wrench-like shape of the molecule (FIG. 21C). In the model, the nonpolar components are clustered on one face of the molecule, and the polar amino handle is located away from the hydrophobic face. Although it remains unclear at this point if wrenchnolol binds Sur-2 in the same conformation, the structural characteristics of free wrenchnolol are analogous to those of an amphiphilic á-helical peptide ligand. Wrenchnolol may be a nonpeptidic organic molecule that presents chemical characteristics of an amphiphilic á-helical peptide without mimicking the á-helical backbone.

The NMR sample of wrenchnolol (7b) was next titrated with a GST fusion of Sur-2 protein. Selective proton signals of wrenchnolol were lost upon the addition of GST-$Sur2_{352-625}$, whereas titration with the corresponding amounts of GST had little effects on those signals (FIG. 22A). The signals arising from adamantane, tosyl, and indole protons were most strongly diminished, while the proton signals of the aminopentyl handle and the bipiperidine linker had little or milder effects upon the addition of GST-$Sur2_{352-625}$ (FIG. 22B). Addition of 30 or 60 μM of GST-$Sur2_{352-625}$ to the NMR sample of wrenchnolol decreased the signal intensities of the methyl protons of the tosyl group and those of the adamantane protons, whereas the signals of the pentylamine protons had little effects. In contrast, addition of the corresponding amounts of GST (top) had no significant effects on those signals. An internal reference signal, 10 μL of dimethyl sulfoxide-δ6 (DMSO), was used. Signal losses are observed when the exchange rate between the free and bound states is intermediate at the NMR time scale and when the chemical shift is perturbed due to the alteration of magnetic environment upon binding. The $K_d$ of wrenchnolol for Sur-2 was estimated to be in a low μM range (see Wrenchnolol with a fluorescein handle) where signal losses are often observed in a similar type of interactions. The lost signals arise from the protons located in the jaws of the molecule, supporting the notion that the hydrophobic jaws of amphiphilic wrenchnolol make direct contacts with Sur-2 protein.

Example 38

Sur-2 Interaction of Wrenchnolol with a Biotinylated Handle

To confirm the interaction of wrenchnolol with Sur-2 in a cellular context, a biotin conjugate of wrenchnolol (8) was synthesized (Scheme 1) and incubated with cell nuclear extracts. The bound proteins were purified through an avidin affinity column, separated on an SDS-PAGE gel, and analyzed by western blots with a Sur-2 antibody. As shown in FIG. 23A, Sur-2 protein was retained on the affinity column in the presence of biotin conjugated wrenchnolol (8), whereas no Sur-2 protein was detected in its absence or in the presence of a control biotin molecule (13). The retention of Sur-2 on the affinity column indicates that wrenchnolol is capable of binding to Sur-2 in the presence of other cellular proteins. Silver-staining detection of all the protein bands on the gel showed a significantly reduced number of protein bands after the affinity purification (compare lanes 2 and 4 in FIG. 23B), demonstrating some degree of binding selectivity of wrenchnolol. One of the silver-stained bands matched the western-blotted band of Sur-2, while the identities of the other bands remained unknown. Sur-2 (also called DRIP130 or CRSP130) is a subunit of the human mediator complexes. The additional bands may include those of the other subunits copurified with Sur-2.

Example 39

Wrenchnolol with a Fluorescein Handle

Figure 24:
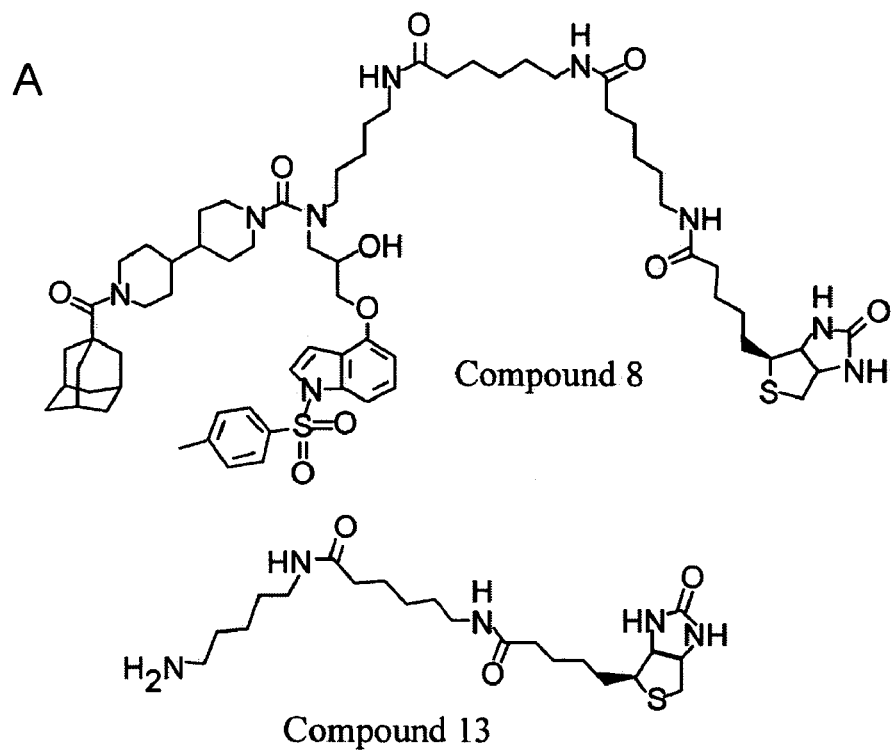
FIG. 24A to FIG. 24C show wrenchnolol with a fluorescein handle (compound 9).
Figure 24:
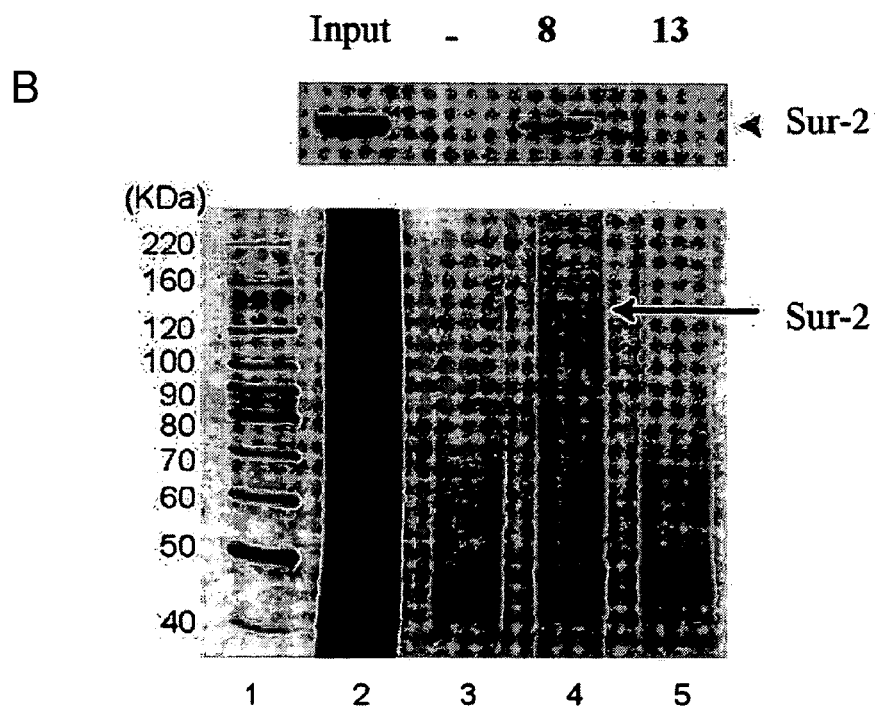

A synthetic compound with a molecular weight higher than 500 is generally less likely to penetrate the cell membrane. To check the cell permeability of wrenchnolol, whose molecular weight is 802, its handle was coupled with a fluorescein molecule through a simple thiourea formation (Scheme 1). Conjugate 9 was incubated with SK-BR3 cells for 1 hr, and fluorescence images were captured by a fluorescence microscope. Fluorescence spectra of conjugate 9 were monitored upon addition of GST-Sur2$_{352-625}$. As shown in FIG. 24A, fluorescein conjugate 9 crossed the cell membrane of breast cancer cells and diffused both in the cytoplasm and the nucleus. However, careful comparison of the fluorescence images of fluorescein conjugate 9 (FIG. 22A) and the nucleus-specific DAPI dye (FIG. 24B) revealed that the compound is located more preferentially in the cytoplasm than in the nucleus, as often observed with large synthetic organic molecules. Although wrenchnolol is capable of penetrating the cell membrane, improvement of its nuclear localization might strengthen the biological activity and selectivity.

Figure 22:
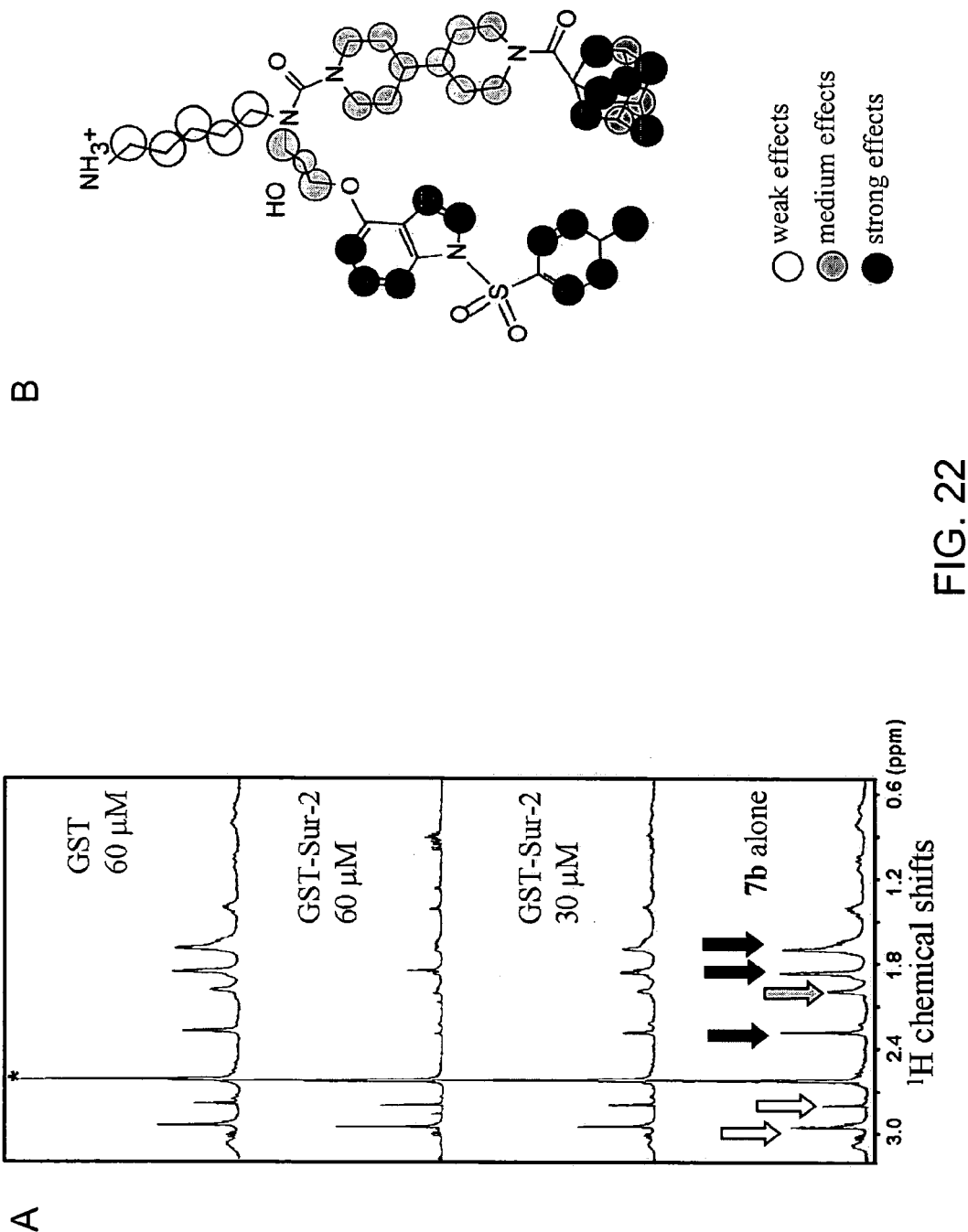
FIG. 22A and FIG. 22B show NMR perturbation study of wrenchnolol (compound 7b).
Figure 23:
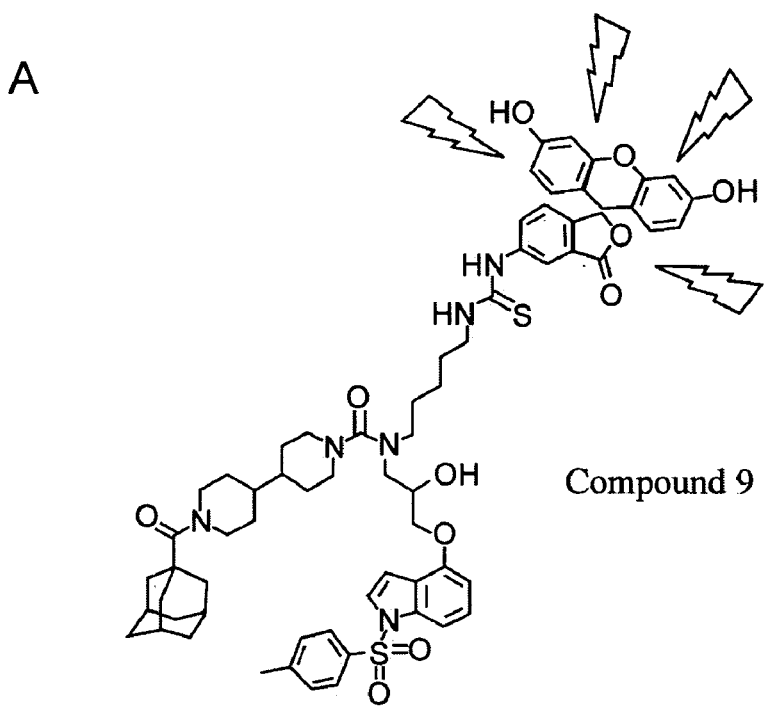
FIG. 23A and FIG. 23B show interaction of biotin-labeled wrenchnolol (compound 8) with Sur-2 in cell extracts.
Figure 23:
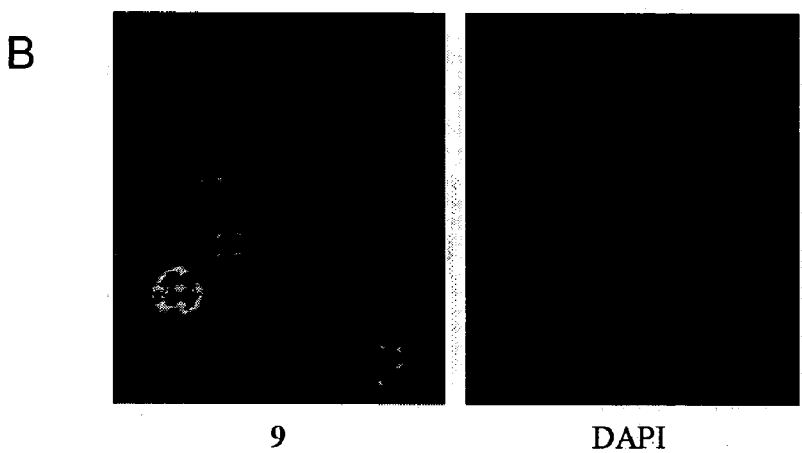
Figure 23:
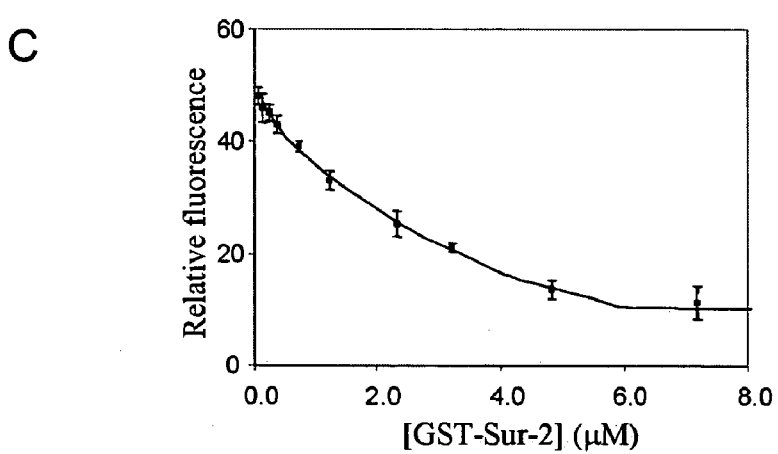

The fluorescein conjugate 9 also enabled evaluation of the $K_d$ value of the interaction between wrenchnolol and Sur-2 in vitro. Shown in FIG. 22C are relative emission intensities of 9 at 522 nm (excitation: 490 nm) in the presence of varied concentrations of GST-Sur2$_{352-625}$. When a GST fusion of Sur-2 protein (GST-Sur2$_{352-625}$) was added to a solution of conjugate 9, the fluorescence intensity of 9 at 522 nm was decreased (FIG. 24C). The clear fluorescence perturbation by the interaction permitted an estimation of the $K_d$ value to be 1.8 μM, which is consistent with the IC$_{50}$ of wrenchnolol in cells.

Example 40

Adamanolol Analogs having Distinct Jaw Widths

Figure 25:
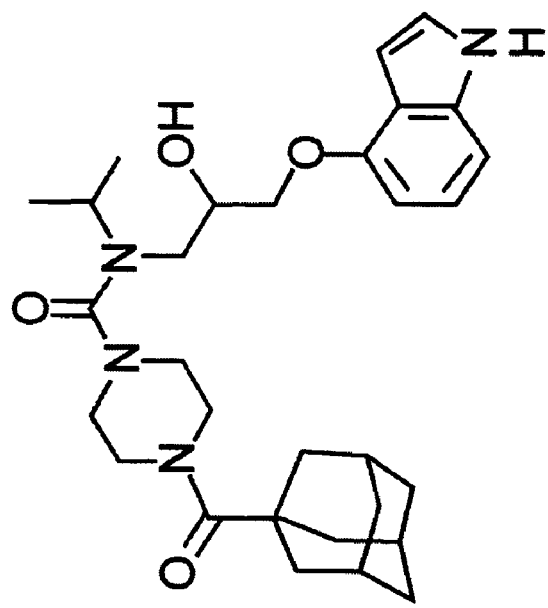
FIG. 25 shows wrenchnolol derivative compounds with different jaw widths.
Figure 25:
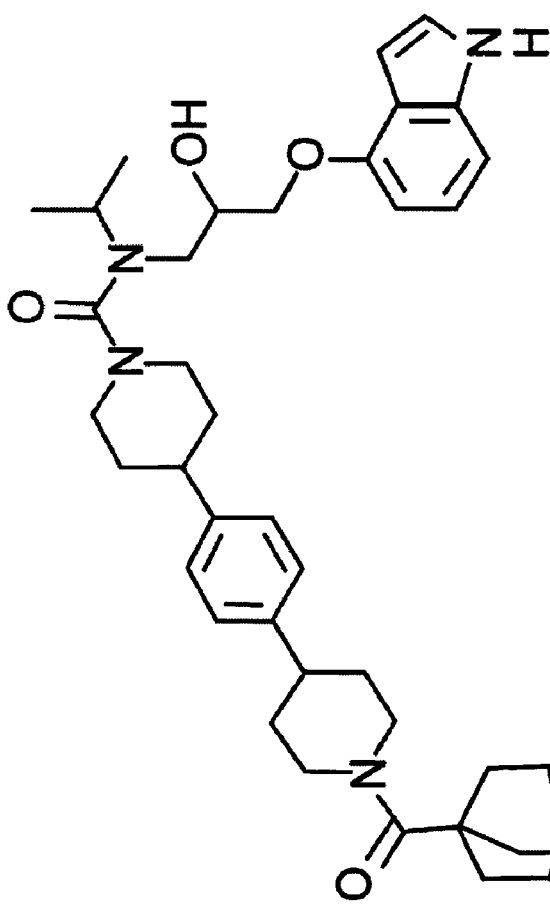

Adamanolol analogs having distinct jaw widths (FIG. 25) were synthesized. In one molecule, the bipiperidine linker was extended by inserting a benzene ring (FIG. compound 14); and in the other, the bipiperidine linker was replaced by a shorter piperadine (FIG. 25, Compound 15). Their evaluation in SK-BR3 cells showed that either the extension or shortening reduced the activity of adamanolol, suggesting that the bipiperidine linker of adamanolol intrinsically has a perfect length for binding to Sur-2. Diversification of the width and shape in the jaws of adamanolol or wrenchnolol may lead to the discovery of inhibitors of distinct á-helix-mediated protein interactions.

REFERENCES

All patents and publications mentioned in the specifications are indicative of the levels of those skilled in the art to which the invention pertains. All patents and publications are herein incorporated by reference to the same extent as if each individual publication was specifically and individually indicated to be incorporated by reference.

U.S. Pat. No. 5,019,660
U.S. Pat. No. 5,053,434

Andreoli, J. M., S. I. Jang, E. Chung, C. M. Coticchia, P. M. Steinert, and N. G. Markova. 1997. The expression of a novel, epithelium-specific ets transcription factor is restricted to the most differentiated layers in the epidermis. Nucleic Acids Res 25, no. 21:4287-95.

Asada, S., Y. Choi, M. Yamada, S. C. Wang, M. C. Hung, J. Qin, and M. Uesugi. 2002. External control of Her2 expression and cancer cell growth by targeting a Ras-linked coactivator. Proc Natl Acad Sci USA 99, 12747-12752.

Bauer, W., U. Briner, W. Doepfnier, R. Haller, R. Huguenin, P. Marbach, T. J. Petcher, and Pless. 1982. SMS 201-995: a very potent and selective octapeptide analogue of somatostatin with prolonged action. Life Sci 31, no. 11: 1133-40.

Boyer, T. G., M. E. Martin, E. Lees, R. P. Ricciardi, and A. J. Berk. 1999. Mammalian Srb/Mediator complex is targeted by adenovirus E1A protein [see comments]. Nature 399, no. 6733:276-9.

Bridges, A. J. 1999. The rationale and strategy used to develop a series of highly potent, irreversible, inhibitors of the epidermal growth factor receptor family of tyrosine kinases. Curr Med Chem 6, no. 9:825-43.

Chang, C. H., G. K. Scott, M. A. Baldwin, and C. C. Benz. 1999. Exon 4-encoded acidic domain in the epithelium-restricted Ets factor, ESX, confers potent transactivating capacity and binds to TATA-binding protein (TBP). Oncogene 18, no. 25:3682-95.

Chang, C. H., G. K. Scott, W. L. Kuo, X. Xiong, Y. Suzdaltseva, J. W. Park, P. Sayre, K. Erny, C. Collins, J. W. Gray, and C. C. Benz. 1997. ESX: a structurally unique Ets overexpressed early during human breast tumorigenesis. Oncogene 14, no. 13:1617-22.

Chiang, S. Y., R. W. Burli, C. C. Benz, L. Gawron, G. K. Scott, P. B. Dervan, and T. A. Beerman. 2000. Targeting the ets binding site of the HER2/neu promoter with pyrrole-imidazole polyamides. J Biol Chem 275, no. 32:24246-54.

Choi, Y., S. Asada, and M. Uesugi. 2000. Divergent hTAFII31-binding motifs hidden in activation domains [In Process Citation]. J Biol Chem 275, no. 21:15912-6.

Collins, J. L., P. J. Dambek, S. W. Goldstein, and W. S. Faraci. 1992. CP-99,711: a non-peptide glucagon receptor antagonist. Bioorg Med Chem Lett 2:915-918.

Dignam J D, Martin P L, Shastry B S, Roeder R 1983; Eukaryotic gene transcription with purified components 101:582-98.

Drebin, J. A., V. C. Link, D. F. Stern, R. A. Weinberg, and M. I. Greene. 1985. Down-modulation of an oncogene protein product and reversion of the transformed phenotype by monoclonal antibodies. Cell 41, no. 3:695-706.

Drebin, J. A., V. C. Link, R. A. Weinberg, and M. I. Greene. 1986. Inhibition of tumor growth by a monoclonal antibody reactive with an oncogene-encoded tumor antigen. Proc Natl Acad Sci USA 83, no. 23:9129-33.

Drews, J. 2000. Drug discovery: a historical perspective [see comments]. Science 287, no. 5460:1960-4.

Ebbinghaus, S. W., J. E. Gee, B. Rodu, C. A. Mayfield, G. Sanders, and D. M. Miller. 1993. Triplex formation inhibits HER-2/neu transcription in vitro. J Clin Invest 92, no. 5:2433-9.

Ebbinghaus, S. W., H. Fortinberry, and H. B. Gamper, Jr. 1999. Inhibition of transcription elongation in the HER-2/neu coding sequence by triplex-directed covalent modification of the template strand. Biochemistry 38, no. 2:619-28.

Foster, B. A., H. A. Coffey, M. J. Morin, and F. Rastinejad. 1999. Pharmacological rescue of mutant p53 conformation and function [see comments]. Science 286, no. 5449:2507-10.

Gusterson, B. A., R. D. Gelber, A. Goldhirsch, K. N. Price, J. Save-Soderborgh, R. Anbazhagan, J. Styles, C. M. Rudenstam, R. Golouh, R. Reed, and et al. 1992. Prognostic importance of c-erbB-2 expression in breast cancer. International (Ludwig) Breast Cancer Study Group. J Clin Oncol 10, no. 7:1049-56.

Guy, C. T., M. A. Webster, M. Schaller, T. J. Parsons, R. D. Cardiff, and W. J. Muller. 1992. Expression of the neu protooncogene in the mammary epithelium of transgenic mice induces metastatic disease. Proc Natl Acad Sci USA 89, no. 22:10578-82.

Hassig, C. A., J. K. Tong, and S. L. Schreiber. 1997. Fiber-derived butyrate and the prevention of colon cancer. Chem Biol 4, no. 11:783-9.

Taunton, J., C. A. Hassig, and S. L. Schreiber. 1996. A mammalian histone deacetylase related to the yeast transcriptional regulator Rpd3p. Science 272, no. 5260:408-11.

Hollywood, D. P., and H. C. Hurst. 1995. Targeting gene transcription: a new strategy to down-regulate c-erbB-2 expression in mammary carcinoma. Br J Cancer 71, no. 4:753-7.

Kwon, H. J., T. Owa, C. A. Hassig, J. Shimada, and S. L. Schreiber. 1998. Depudecin induces morphological reversion of transformed fibroblasts via the inhibition of histone deacetylase. Proc Natl Acad Sci USA 95, no. 7:3356-61.

Lin, R. J., L. Nagy, S. Inoue, W. Shao, W. H. Miller, Jr., and R. M. Evans. 1998. Role of the histone deacetylase complex in acute promyelocytic leukaemia. Nature 391, no. 6669:811-4.

Nagahara, H., A. M. Vocero-Akbani, E. L. Snyder, A. Ho, D. G. Latham, N. A. Lissy, M. Becker-Hapak, S. A. Ezhevsky, and S. F. Dowdy. 1998. Transduction of full-length TAT fusion proteins into mammalian cells: TAT-p27Kip1 induces cell migration. Nat Med 4, no. 12:1449-52.

Naar, A. M., P. A. Beaurang, S. Zhou, S. Abraham, W. Solomon, and R. Tjian. 1999. Composite co-activator ARC mediates chromatin-directed transcriptional activation. Nature 398, no. 6730:828-32.

Nakanishi T, Oka T, Akagi T. 2001. Recent advances in DNA microarrays. Acta Med Okayam, no. 55(6):319-28.

Noonberg, S. B., G. K. Scott, C. A. Hunt, M. E. Hogan, and C. C. Benz. 1994. Inhibition of transcription factor binding to the HER2 promoter by triplex-forming oligodeoxyribonucleotides. Gene 149, no. 1:123-6.

Pasternak, A., Y. Pan, D. Marino, P. E. Sanderson, R. Mosley, S. P. Rohrer, E. T. Birzin, S. E. Huskey, T. Jacks, K. D. Schleim, K. Cheng, J. M. Schaeffer, A. A. Patchett, and L. Yang. 1999. Potent, orally bioavailable somatostatin agonists: good absorption achieved by urea backbone cyclization. Bioorg Med Chem Lett 9, no. 3:491-6.

Patchett A. 1998. Synthesis and biological activities of potent peptidomimetics selective for somatostatin receptor subtype 2. Proc Natl Acad Sci USA 95, no. 18:10836-41.

Perou, C. M., T. Sorlie, M. B. Eisen, M. van de Rijn, S. S. Jeffrey, C. A. Rees, J. R. Pollack, D. T. Ross, H. Johnsen, L. A. Akslen, O. Fluge, A. Pergamenschikov, C. Williams, S. X. Zhu, P. E. Lonning, A. L. Borresen-Dale, P. O. Brown, and D. Botstein. 2000. Molecular portraits of human breast tumours. Nature 406, no. 6797:747-52.

Poitout, L., P. Roubert, M. O. Contour-Galcera, C. Moinet, J. Lannoy, J. Pommier, P. Plas, D. Bigg, and C. Thurieau. 2001. Identification of potent non-peptide somatostatin antagonists with sst(3) selectivity. J Med Chem 44, no. 18:2990-3000.

Porumb, H., H. Gousset, R. Letellier, V. Salle, D. Briane, J. Vassy, M. Amor-Gueret, L. Israel, and E. Taillandier. 1996. Temporary ex vivo inhibition of the expression of the human oncogene HER2 (NEU) by a triple helix-forming oligonucleotide. Cancer Res 56, no. 3:515-22.

Rachez, C., B. D. Lemon, Z. Suldan, V. Bromleigh, M. Gamble, A. M. Naar, H. Erdjument-Bromage, P. Tempst, and L. P. Freedman. 1999. Ligand-dependent transcription activation by nuclear receptors requires the DRIP complex. Nature 398, no. 6730:824-8.

Reichlin, S. 1983. Somatostatin. N Engl J Med 309, no. 24:1495-501.

Roh, H., J. A. Pippin, D. W. Green, C. B. Boswell, C. T. Hirose, N. Mokadam, and J. A. Drebin. 2000. HER2/neu antisense targeting of human breast carcinoma. Oncogene 19, no. 53:6138-43.

Roh, H., J. Pippin, and J. A. Drebin. 2000. Down-regulation of HER2/neu expression induces apoptosis in human cancer cells that overexpress HER2/neu. Cancer Res 60, no. 3:560-5.

Ross, J. S., and J. A. Fletcher. 1999. HER-2/neu (c-erb-B2) gene and protein in breast cancer. Am J Clin Pathol 112, no. 1 Suppl 1:S53-67Ryu, S., S. Zhou, A. G. Ladurner, and R. Tjian. 1999. The transcriptional cofactor complex CRSP is required for activity of the enhancer-binding protein Sp1. Nature 397, no. 6718:446-50.

Schwarze, S. R., A. Ho, A. Vocero-Akbani, and S. F. Dowdy. 1999. In vivo protein transduction: delivery of a biologically active protein into the mouse [see comments]. Science 285, no. 5433:1569-72.

Scott, G. K., J. C. Daniel, X. Xiong, R. A. Maki, D. Kabat, and C. C. Benz. 1994. Binding of an ETS-related protein within the DNase I hypersensitive site of the HER2/neu promoter in human breast cancer cells. J Biol Chem 269, no. 31:19848-58.

Singh, N., and M. Han. 1995. sur-2, a novel gene, functions late in the let-60 ras-mediated signaling pathway during Caenorhabditis elegans vulval induction. Genes Dev 9, no. 18:2251-65.

Slamon, D. J., W. Godolphin, L. A. Jones, J. A. Holt, S. G. Wong, D. E. Keith, W. J. Levin, S. G. Stuart, J. Udove, A. Ullrich, and et al. 1989. Studies of the HER-2/neu proto-oncogene in human breast and ovarian cancer. Science 244, no. 4905:707-12.

Slamon, D. J., G. M. Clark, S. G. Wong, W. J. Levin, A. Ullrich, and W. L. McGuire. 1987. Human breast cancer: correlation of relapse and survival with amplification of the HER-2/neu oncogene. Science 235, no. 4785:177-82.

Stevens, J. L., G. T. Cantin, G. Wang, A. Shevchenko, and A. J. Berk. 2002. Transcription control by E1A and MAP kinase pathway via Sur2 mediator subunit. Science 296, no. 5568:755-8.

Takase, Y., T. Saeki, N. Watanabe, H. Adachi, S. Souda, and I. Saito. 1994. Cyclic GMP phosphodiesterase inhibitors. 2. Requirement of 6-substitution of quinazoline derivatives for potent and selective inhibitory activity. J Med Chem 37, no. 13:2106-11.

Veber, D. F. 1992. Design and discovery in the development of peptide analogs. In Peptides, Chemistry and Biology: Proceedings of the 12th American Peptide Symposium; Smith, J. A., Rivier, J. E., Eds.; ESCOM: Leiden:pp 3-14.

Yang, L., S. C. Berk, S. P. Rohrer, R. T. Mosley, L. Guo, D. J. Underwood, B. H. Arison, E. T. Birzin, E. C. Hayes, S. W. Mitra, R. M. Parmar, K. Cheng, T. J. Wu, B. S. Butler, F. Foor, A. Pasternak, Y. Pan, M. Silva, R. M. Freidinger, R. G. Smith, K. Chapman, J. M. Schaeffer, and Rohrer, S. P., E. T. Birzin, R. T. Mosley, S. C. Berk, S. M. Hutchins, D. M. Shen, Y. Xiong, E. C. Hayes, R. M. Parmar, F. Foor, S. W. Mitra, S. J. Degrado, M. Shu, J. M. Klopp, S. J. Cai, A. Blake, W. W. Chan, A. Pasternak, L. Yang, A. A. Patchett, R. G. Smith, K. T. Chapman, and J. M.

Schaeffer. 1998. Rapid identification of subtype-selective agonists of the somatostatin receptor through combinatorial chemistry. Science 282, no. 5389:737-40.

Yu, D., B. Liu, T. Jing, D. Sun, J. E. Price, S. E. Singletary, N. Ibrahim, G. N. Hortobagyi, and M. C. Hung. 1998. Overexpression of both p185c-erbB2 and p170mdr-1 renders breast cancer cells highly resistant to taxol. Oncogene 16, no. 16:2087-94.

Yu, D. H., and M. C. Hung. 1991. Expression of activated rat neu oncogene is sufficient to induce experimental metastasis in 3T3 cells. Oncogene 6, no. 11:1991-6.

Zhou, B. P., M. C. Hu, S. A. Miller, Z. Yu, W. Xia, S. Y. Lin, and M. C. Hung. 2000. HER-2/neu blocks tumor necrosis factor-induced apoptosis via the Akt/NF-kappaB pathway. J Biol Chem 275, no. 11:8027-31.

The invention claimed is:

1. A compound of the formula:

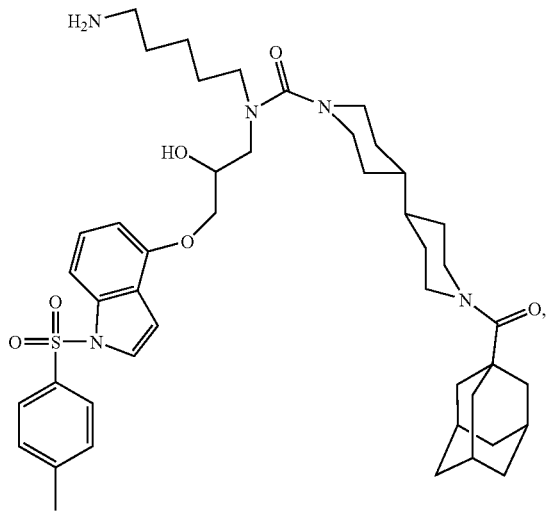

and pharmaceutically acceptable salts thereof.

2. A compound of the formula:

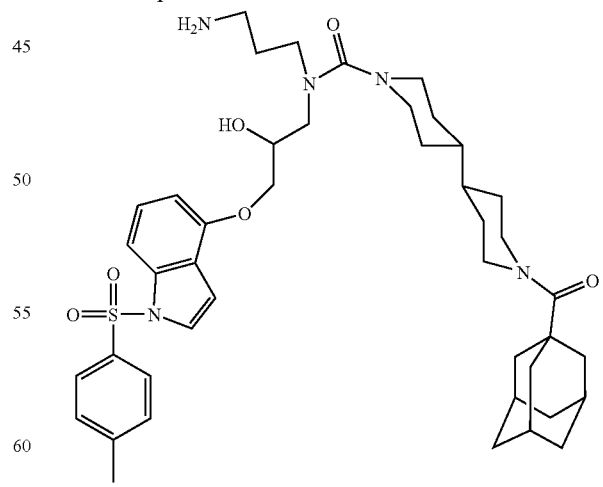

and pharmaceutically acceptable salts thereof.

* * * * *

SEQUENCE LISTING

<160> NUMBER OF SEQ ID NOS: 2

<210> SEQ ID NO 1
<211> LENGTH: 8
<212> TYPE: PRT
<213> ORGANISM: Human

<400> SEQUENCE: 1

Ser Trp Ile Ile Glu Leu Leu Glu
1               5

<210> SEQ ID NO 2
<211> LENGTH: 1368
<212> TYPE: PRT
<213> ORGANISM: Human

<400> SEQUENCE: 2

Met Glu Thr Gln Leu Gln Ser Ile Phe Glu Glu Val Val Lys Thr Glu
1               5                   10                  15

Val Ile Glu Glu Ala Phe Pro Gly Met Phe Met Asp Thr Pro Glu Asp
            20                  25                  30

Glu Lys Thr Lys Leu Ile Ser Cys Leu Gly Ala Phe Arg Gln Phe Trp
        35                  40                  45

Gly Gly Leu Ser Gln Glu Ser His Glu Gln Cys Ile Gln Trp Ile Val
    50                  55                  60

Lys Phe Ile His Gly Gln His Ser Pro Lys Arg Ile Ser Phe Leu Tyr
65                  70                  75                  80

Asp Cys Leu Ala Met Ala Val Glu Thr Gly Leu Leu Pro Pro Arg Leu
                85                  90                  95

Val Cys Glu Ser Leu Ile Asn Ser Asp Thr Leu Glu Trp Glu Arg Thr
            100                 105                 110

Gln Leu Trp Ala Leu Thr Phe Lys Leu Val Arg Lys Ile Ile Gly Gly
        115                 120                 125

Val Asp Tyr Lys Gly Val Arg Asp Leu Leu Lys Val Ile Leu Glu Lys
    130                 135                 140

Ile Leu Thr Ile Pro Asn Thr Val Ser Ser Ala Val Val Gln Gln Leu
145                 150                 155                 160

Leu Ala Ala Arg Glu Val Ile Ala Tyr Ile Leu Glu Arg Asn Ala Cys
                165                 170                 175

Leu Leu Pro Ala Tyr Phe Ala Val Thr Glu Ile Arg Lys Leu Tyr Pro
            180                 185                 190

Glu Gly Lys Leu Pro His Trp Leu Leu Gly Asn Leu Val Ser Asp Phe
        195                 200                 205

Val Asp Thr Phe Arg Pro Thr Ala Arg Ile Asn Ser Ile Cys Gly Arg
    210                 215                 220

Cys Ser Leu Leu Pro Val Asn Asn Ser Gly Ala Ile Cys Asn Ser
225                 230                 235                 240

Trp Lys Leu Asp Pro Ala Thr Leu Arg Phe Pro Leu Lys Gly Leu Leu
                245                 250                 255

Pro Tyr Asp Lys Asp Leu Phe Glu Pro Gln Thr Ala Leu Leu Arg Tyr
            260                 265                 270

Val Leu Glu Gln Pro Tyr Ser Arg Asp Met Val Cys Asn Met Leu Gly
        275                 280                 285

Leu Asn Lys Gln His Lys Gln Arg Cys Pro Val Leu Glu Asp Gln Leu
    290                 295                 300

-continued

```
Val Asp Leu Val Val Tyr Ala Met Glu Arg Ser Glu Thr Glu Lys
305                 310                 315                 320

Phe Asp Asp Gly Gly Thr Ser Gln Leu Leu Trp Gln His Leu Ser Ser
            325                 330                 335

Gln Leu Ile Phe Phe Val Leu Phe Gln Phe Ala Ser Phe Pro His Met
                340                 345                 350

Val Leu Ser Leu His Gln Lys Leu Ala Gly Arg Gly Leu Ile Lys Gly
            355                 360                 365

Arg Asp His Leu Met Trp Val Leu Leu Gln Phe Ile Ser Gly Ser Ile
    370                 375                 380

Gln Lys Asn Ala Leu Ala Asp Phe Leu Pro Val Met Lys Leu Phe Asp
385                 390                 395                 400

Leu Leu Tyr Pro Glu Lys Glu Tyr Ile Pro Val Asp Ile Asn Lys
                405                 410                 415

Pro Gln Ser Thr His Ala Phe Ala Met Thr Cys Ile Trp Ile His Leu
            420                 425                 430

Asn Arg Lys Ala Gln Asn Asp Asn Ser Lys Leu Gln Ile Pro Ile Pro
            435                 440                 445

His Ser Leu Arg Leu His His Glu Phe Leu Gln Gln Ser Leu Arg Asn
            450                 455                 460

Lys Ser Leu Gln Met Asn Asp Tyr Lys Ile Ala Leu Leu Cys Asn Ala
465                 470                 475                 480

Tyr Ser Thr Asn Ser Glu Cys Phe Thr Leu Pro Met Gly Ala Leu Val
                485                 490                 495

Glu Thr Ile Tyr Gly Asn Gly Ile Met Arg Ile Pro Leu Pro Gly Thr
            500                 505                 510

Asn Cys Met Ala Ser Gly Ser Ile Thr Pro Leu Pro Met Asn Leu Leu
            515                 520                 525

Asp Ser Leu Thr Val His Ala Lys Met Ser Leu Ile His Ser Ile Ala
530                 535                 540

Thr Arg Val Ile Lys Leu Ala His Ala Lys Ser Ser Val Ala Leu Ala
545                 550                 555                 560

Pro Ala Leu Val Glu Thr Tyr Ser Arg Leu Leu Val Tyr Met Glu Ile
                565                 570                 575

Glu Ser Leu Gly Ile Lys Gly Phe Ile Ser Gln Leu Leu Pro Thr Val
            580                 585                 590

Phe Lys Ser His Ala Trp Gly Ile Leu His Thr Leu Leu Glu Met Phe
            595                 600                 605

Ser Tyr Arg Met His His Ile Gln Pro His Tyr Arg Val Gln Leu Leu
            610                 615                 620

Ser His Leu His Thr Leu Ala Ala Val Ala Gln Thr Asn Gln Asn Gln
625                 630                 635                 640

Leu His Leu Cys Val Glu Ser Thr Ala Leu Arg Leu Ile Thr Ala Leu
                645                 650                 655

Gly Ser Ser Glu Val Gln Pro Gln Phe Thr Arg Phe Leu Ser Asp Pro
            660                 665                 670

Lys Thr Val Leu Ser Ala Glu Ser Glu Glu Leu Asn Arg Ala Leu Ile
        675                 680                 685

Leu Thr Leu Ala Arg Ala Thr His Val Thr Asp Phe Phe Thr Gly Ser
            690                 695                 700

Asp Ser Ile Gln Gly Thr Trp Cys Lys Asp Ile Leu Gln Thr Ile Met
705                 710                 715                 720
```

-continued

```
Ser Phe Thr Pro His Asn Trp Ala Ser His Thr Leu Ser Cys Phe Pro
                725                 730                 735

Gly Pro Leu Gln Ala Phe Phe Lys Gln Asn Val Pro Gln Glu Ser
            740                 745                 750

Arg Phe Asn Leu Lys Lys Asn Val Glu Glu Tyr Arg Lys Trp Lys
        755                 760                 765

Ser Met Ser Asn Glu Asn Asp Ile Ile Thr His Phe Ser Met Gln Gly
    770                 775                 780

Ser Pro Pro Leu Phe Leu Cys Leu Leu Trp Lys Met Leu Leu Glu Thr
785                 790                 795                 800

Asp His Ile Asn Gln Ile Gly Tyr Arg Val Leu Glu Arg Ile Gly Ala
                805                 810                 815

Arg Ala Leu Val Ala His Val Arg Thr Phe Ala Asp Phe Leu Val Tyr
            820                 825                 830

Glu Phe Ser Thr Ser Ala Gly Gly Gln Gln Leu Asn Lys Cys Ile Glu
        835                 840                 845

Ile Leu Asn Asp Met Val Trp Lys Tyr Asn Ile Val Thr Leu Asp Arg
    850                 855                 860

Leu Ile Leu Cys Leu Ala Met Arg Ser His Glu Gly Asn Glu Ala Gln
865                 870                 875                 880

Val Cys Tyr Phe Ile Ile Gln Leu Leu Leu Lys Pro Asn Asp Phe
                885                 890                 895

Arg Asn Arg Val Ser Asp Phe Val Lys Glu Asn Ser Pro Glu His Trp
            900                 905                 910

Leu Gln Asn Asp Trp His Thr Lys His Met Asn Tyr His Lys Lys Tyr
        915                 920                 925

Pro Glu Lys Leu Tyr Phe Glu Gly Leu Ala Glu Gln Val Asp Pro Pro
    930                 935                 940

Val Gln Ile Gln Ser Pro Tyr Leu Pro Ile Tyr Phe Gly Asn Val Cys
945                 950                 955                 960

Leu Arg Phe Leu Pro Val Phe Asp Ile Val Ile His Arg Phe Leu Glu
                965                 970                 975

Leu Leu Pro Val Ser Lys Ser Leu Glu Thr Leu Leu Asp His Leu Gly
            980                 985                 990

Gly Leu Tyr Lys Phe His Asp Arg Pro Val Thr Tyr Leu Tyr Asn Thr
        995                 1000                1005

Leu His Tyr Tyr Glu Met His Leu Arg Asp Arg Ala Phe Leu Lys
    1010                1015                1020

Arg Lys Leu Val His Ala Ile Ile Gly Ser Leu Lys Asp Asn Arg
    1025                1030                1035

Pro Gln Gly Trp Cys Leu Ser Asp Thr Tyr Leu Lys Cys Ala Met
    1040                1045                1050

Asn Ala Arg Glu Glu Asn Pro Trp Val Pro Asp Thr Tyr Tyr
    1055                1060                1065

Cys Arg Leu Ile Gly Arg Leu Val Asp Thr Met Ala Gly Lys Ser
    1070                1075                1080

Pro Gly Pro Phe Pro Asn Cys Asp Trp Arg Phe Asn Glu Phe Pro
    1085                1090                1095

Asn Pro Ala Ala His Ala Leu His Val Thr Cys Val Glu Leu Met
    1100                1105                1110

Ala Leu Ala Val Ser Gly Lys Glu Val Gly Asn Ala Leu Leu Asn
    1115                1120                1125

Val Val Leu Lys Ser Gln Pro Leu Val Pro Arg Glu Asn Ile Thr
```

```
                1130                1135                1140
Ala Trp Met Asn Ala Ile Gly Leu Ile Ile Thr Ala Leu Pro Glu
                1145                1150                1155
Pro Tyr Trp Ile Val Leu His Asp Arg Ile Val Ser Val Ile Ser
                1160                1165                1170
Ser Pro Ser Leu Thr Ser Glu Thr Glu Trp Val Gly Tyr Pro Phe
                1175                1180                1185
Arg Leu Phe Asp Phe Thr Ala Cys His Gln Ser Tyr Ser Glu Met
                1190                1195                1200
Ser Cys Ser Tyr Thr Leu Ala Leu Ala His Ala Val Trp His His
                1205                1210                1215
Ser Ser Ile Gly Gln Leu Ser Leu Ile Pro Lys Phe Leu Thr Glu
                1220                1225                1230
Val Leu Leu Pro Ile Val Lys Thr Glu Phe Gln Leu Leu Tyr Val
                1235                1240                1245
Tyr His Leu Val Gly Pro Phe Leu Gln Arg Phe Gln Gln Glu Arg
                1250                1255                1260
Thr Arg Cys Met Ile Glu Ile Gly Val Ala Phe Tyr Asp Met Leu
                1265                1270                1275
Leu Asn Val Asp Gln Cys Ser Thr His Leu Asn Tyr Met Asp Pro
                1280                1285                1290
Ile Cys Asp Phe Leu Tyr His Met Lys Tyr Met Phe Thr Gly Asp
                1295                1300                1305
Ser Val Lys Glu Gln Val Glu Lys Ile Ile Cys Asn Leu Lys Pro
                1310                1315                1320
Ala Leu Lys Leu Arg Leu Arg Phe Ile Thr His Ile Ser Lys Met
                1325                1330                1335
Glu Pro Ala Ala Val Pro Pro Gln Ala Met Asn Ser Gly Ser Pro
                1340                1345                1350
Ala Pro Gln Ser Asn Gln Val Pro Val Ser Leu Pro Val Thr Gln
                1355                1360                1365
```